United States Patent [19]

Natsugari et al.

[11] Patent Number: 5,527,811
[45] Date of Patent: Jun. 18, 1996

[54] ISOQUINOLINYL COMPOUNDS WHICH ARE USEFUL IN TREATING CEREBRAL VASCULAR DISORDERS

[75] Inventors: Hideaki Natsugari, Ashiya; Tetsuji Imamoto, Kitakatsuragi-gun; Yuzo Ichimori, Sakai, all of Japan

[73] Assignee: Takeda Chemical Industries, Ltd., Osaka, Japan

[21] Appl. No.: 274,263

[22] Filed: Jul. 13, 1994

[30] Foreign Application Priority Data

Jul. 14, 1993 [JP] Japan .................................. 5-173918

[51] Int. Cl.$^6$ ..................... C07D 217/24; C07D 405/06; A61K 31/47
[52] U.S. Cl. ..................... 514/309; 514/231.5; 514/252; 514/308; 544/128; 544/238; 546/140; 546/141; 546/142
[58] Field of Search .................... 544/128, 238; 546/140, 141, 142; 514/231.5, 252, 308, 309, 310

[56] References Cited

FOREIGN PATENT DOCUMENTS

| 0326386 | 8/1989 | European Pat. Off. ............... 546/140 |
| 0333174 | 9/1989 | European Pat. Off. ............... 514/310 |
| 0112967 | 5/1991 | Japan ................................... 546/140 |

OTHER PUBLICATIONS

Unver ferth et al, Arch. Pharm., vol. 324. No. 10, Oct. 1991, pp. 809–814.

*Primary Examiner*—Zinna Northington Davis
*Attorney, Agent, or Firm*—Foley & Lardner

[57] ABSTRACT

Compounds represented by the formula:

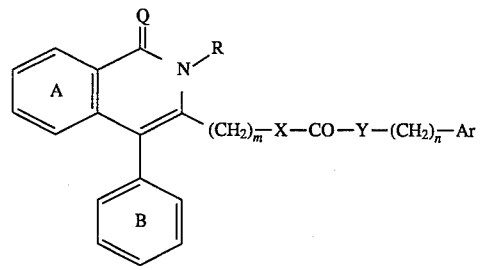

wherein the ring A and the ring B each stand for an optionally substituted benzene ring; Ar stands for an optionally substituted aryl group or an optionally substituted heterocyclic group; Q stands for an oxygen atom or a sulfur atom; R stands for a hydrogen atom, an optionally substituted hydrocarbon group, an optionally substituted hydroxyl group or an optionally substituted amino group; X stands for —O— or —NR$^1$— wherein R$^1$ stands for a hydrogen atom or an optionally substituted hydrocarbon group; Y stands for —O—, —NR$^2$— wherein R$^2$ stands for a hydrogen atom or an optionally substituted hydrocarbon group, or a bond; m denotes 1, 2 or 3, and n denotes 0, 1 or 2, and salts thereof which have excellent calcium- or substance P receptor-antagonistic activity, being useful for treating a cerebralvascular disorder in mammals such as cerebralischemia, cerebral edema and neuronal damage, their production and use.

40 Claims, No Drawings

ISOQUINOLINYL COMPOUNDS WHICH ARE USEFUL IN TREATING CEREBRAL VASCULAR DISORDERS

This invention relates to a novel isoquinolone compound having medicinal activities including an excellent calcium-antagonistic activity, protective effect of cerebralischemia, anti-cerebral edema activity, protective effect of neuronal damage and tachykinin receptor antagonizing activity.

Recently, in living bodies, the role of calcium in various cells as a neuro transmitter has attracted attention, and its importance has been cleared up. Disruption of calcium homeostasis is considered to be a factor of causing, morbidly or physically, cell damage or cell death. In neuronal cells also, disruption of calcium homeostasis, in other words, neuronal damage or cell death in the cerebralvascular disorders such as cerebralischemia is caused by the release from cellular calcium ion ($Ca^{2+}$) stores or influx of extracellular calucium ion. "Stuart A. Lipton, Advances in Pharmacology, 22, pp. 271–297 (1991); Trends in Pharmacological Sciences, 10, pp 397–400 (1989)".

Under the above circumstances, development of new compounds having excellent calcium-antagonistic activity directly acting on neural cells as therapeutic and prophylactic drugs for neuronal damage such as cerebralischemic damage and cerebral edema in cerebralvascular disorders and also having excellent properties in respect to safety and durability or the like has been desired.

Tachykinin is a generic term denoting a group of neuropeptides. In mammalian animals, substance P, neurokinin-A and neurokinin-B are known. It is also known that by binding respective receptors (neurokinin-1, neurokinin-2, neurokinin-3) present in the living body, these peptides exhibit a diversity of biological activities. Among them, substance P is a neuropeptide which was known for the longest time of all and studied in the greatest detail. Substance P is known to play a critical role as a neuro transmitter in both the peripheral and central nervous systems. This substance is also suspected to be involved in a variety of morbid states (e.g. pain, inflammation, allergy, mental diseases, etc.). Such being the case, for use as drugs for the treatment of the above-mentioned disease states, the development of compounds having potent tachykinin receptor antagonizing activity, particularly antagonistic activity against substance P receptor, as well as other favorable properties such as safety and a long duration of action after administration has been looked after in earnest.

As the compounds known as having activity toward the substance P receptor, there are disclosed:

(1) in EP-A-333,174, a compound represented by the formula; $R^1$-A-D-Trp($R^2$)-Phe-$R^3$ wherein $R^1$ stands for a hydrogen or an amino-protecting group, $R^2$ stands for a hydrogen, an amino-protecting group, a carbamoyl(lower)alkyl group, a carboxy(lower)alkyl group or a protected carboxy(lower)alkyl group, $R^3$ stands for an ar(lower)alkyl group, a group represented by the formula:

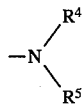

wherein $R^4$ and $R^5$ respectively stand for a hydrogen, an aryl group or a lower alkyl group optionally having a suitable substituent, or they are bonded to each other to form a benzene-condensed lower alkylene group, or a group represented by the formula:

$OR^6$ wherein $R^6$ stands for a hydrogen, an aryl group or a lower alkyl group optionally having a suitable substituent, A stands for a single bond or one or two amino acid residues, provided that, when A is an amino acid residue of —D-Trp—, $R^4$ is not hydrogen and a salt thereof, (2) in EP-A-436,334, a compound represented by the formula:

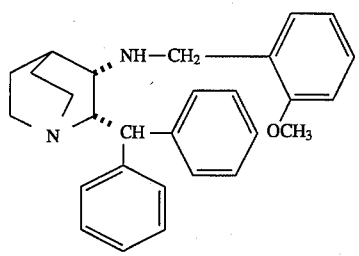

(3) in EP-A-429,366, a compound represented by the formula:

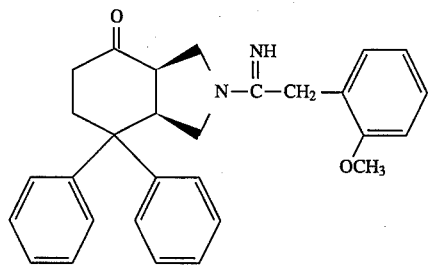

and, (4) in the Journal of Medicinal Chemistry, vol. 34, p. 1751(1991), a compound represented by the formula:

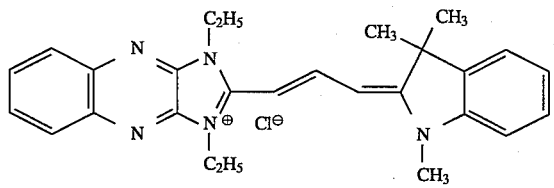

among others.

And, as compounds having ACAT-inhibiting activity, heterocyclic compounds [A] as set forth in the following Table 1 have been known.

TABLE 1

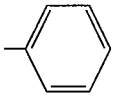

[A]

| Appln. | X | Y | R |
|---|---|---|---|
| WO 91/9017 | $R^1$<br>\|<br>—N=C—<br>\|<br>$R^2$<br>\|<br>—N—CO—<br>$R^1, R^2$ = H, lower alkyl | —(CH$_2$)$_m$—<br>m = 0~2<br>—CH=CH— | 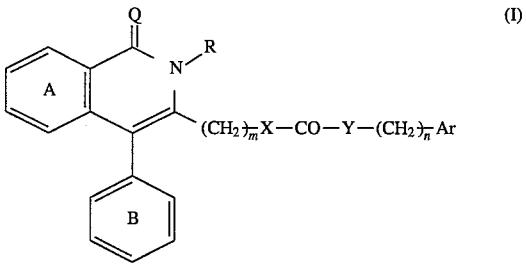<br>$R^3, R^4$ = H, etc.<br>$R^5$ = halogen, etc. |
| WO 91/12249 | —O—CO—<br>—O—CH$_2$—<br>—S—CO—<br>etc. | bond<br>—NH—<br>alkylene | hydrocarbon |
| EP 421456 | $R^1$<br>\|<br>—N—CO—<br>$R^2$<br>\|<br>—N=C—<br>$R^1$ = H, etc., $R^2$ = lower alkyl | —NH(CH$_2$)$_n$—<br>n = 0, 1 | ⟨phenyl⟩ |
| EP 481383 | —CO—O—<br>—CO—NR$^1$—<br>etc.<br>$R^1$ = H, etc. | —NH—<br>—O—<br>—(CH$_2$)$_n$—<br>n = 0~2 | hydrocarbon |

The novel compound having an excellent calcium-antagonizing activity directly acting on neuronal cells which are useful as therapeutic and prophylactic drugs for neuronal damage, such as cerebralischemic damage and cerebral edema in cerebralvascular disorders, and also having excellent properties in respect to safety and durability, and also the development of a novel compound having excellent tachykinin receptor antagonist, especially having substance P receptor antagonizing activity, and also having excellent properties in respects of safety and durability, among others is desired.

The present inventors, taking the above circumstances into consideration, have made diligent research work, and synthesized, for the first time, a novel heterocyclic compound whose structural characteristic feature lies in that the side chain is substituted through the alkylene group at the 3-position of the isoquinolone skeleton, and found that this novel compound has, unexpectedly, due to its specific chemical structure of the side chain, excellent action in inhibiting of the release from cellular calcium ion stores, protecting against cerebralischemic disorders, an cerebral edema, and neuronal damage. On the basis of these findings, the present invention has been accomplished.

More specifically, the present invention relates to:

(1) a compound represented by the formula:

$$\text{(I)}$$

wherein the ring A and the ring B each stand for an optionally substituted benzene ring; Ar stands for an optionally substituted aryl group or an optionally substituted heterocyclic group; Q stands for an oxygen atom or a sulfur atom; R stands for a hydrogen atom, an optionally substituted hydrocarbon group, an optionally substituted hydroxyl group or an optionally substituted amino group; X stands for —O— or —NR$^2$— wherein R$^1$ stands for a hydrogen atom or an optionally substituted hydrocarbon group; Y stands for —O—, —NR$^2$— wherein R$^2$ stands for a hydrogen atom or an optionally substituted hydrocarbon group, or a bond; m denotes 1, 2 or 3, and n denotes 0, 1 or 2, or a salt thereof, (2) a compound as described in the above (1), wherein the ring A and the ring B each are a benzene ring which may be substituted with 1 to 4 substituents selected from the group consisting of a halogen atom, optionally halogenated C$_{1-6}$ alkyl group, optionally halogenated C$_{1-6}$ alkoxy group, optionally halogenated C$_{1-6}$ alkylthio group, C$_{1-7}$ acylamino group, $C_{1-7}$ acyloxy group, hydroxyl group, nitro group, cyano group, amino group, mono- or di-$C_{1-4}$ alkylamino group, pyrrolidino group, piperidino group, morpholino group, $C_{1-4}$ alkyl-carbonyl group, $C_{1-4}$ alkylsulfonylamino group, carboxyl group, $C_{1-6}$ alkyl-carbonyl group, $C_{1-4}$ alkoxy-carbonyl group, carbamoyl group, mono- or di-$C_{1-4}$ alkylcarbamoyl group and $C_{1-4}$ alkylsulfonyl group, (3) a compound as described in the above (1), wherein the ring A and the ring B each are a benzene ring which may be substituted with 1 to 3 substituents selected from the group consisting of a halogen atom, optionally halogenated $C_{1-4}$ alkyl group, optionally halogenated $C_{1-4}$ alkoxy group, optionally halogenated $C_{1-4}$ alkylthio group, hydroxyl group, amino group, mono- or di-$C_{1-4}$ alkylamino group, carboxyl group and $C_{1-4}$ alkoxy-carbonyl group, (4) a compound as described in the above (1), wherein the ring A and the ring B each are a benzene ring which may be substituted with 1 or 2 substituents selected from the group consisting of a halogen atom, optionally halogenated $C_{1-4}$ alkyl group and optionally halogenated $C_{1-4}$ alkoxy group, (5) a compound as described in the above (1), wherein the ring B is an unsubstituted benzene ring, (6) a compound as described in the above (1), wherein the ring A is a benzene ring which may be substituted with 1 or 2 substituents selected from the group consisting of a halogen atom and optionally halogenated $C_{1-4}$ alkyl group; and the ring B is an unsubstituted benzene ring, (7) a compound as described in the above (1), wherein R is a hydrogen atom, (8) a compound as described in the above (1), wherein R is a $C_{1-6}$ alkyl group, (9) a compound as described in the above (1), wherein Q is an oxygen atom,

(10) a compound as described in the above (1), wherein X is —O—,

(11) a compound as described in the above (1), wherein X is —NH—,

(12) a compound as described in the above (1), wherein $R^2$ is (i) a hydrogen atom or (ii) a $C_{1-4}$ alkyl group which may be substituted with a $C_{1-4}$ alkoxy-carbonyl group or a carboxyl group,

(13) a compound as described in the above (1), wherein $R^2$ is a hydrogen atom or a $C_{1-4}$ alkyl group,

(14) a compound as described in the above (1), wherein Y is —NH—,

(15) a compound as described in the above (1), wherein Y is a bond,

(16) a compound as described in the above (1), wherein m is 1,

(17) a compound as described in the above (1), wherein m is 2,

(18) a compound as described in the above (1), wherein n is 0,

(19) a compound as described in the above (1), wherein n is 1,

(20) a compound as described in the above (1), wherein Ar is a phenyl group which may be substituted with 1 or 2 substituents selected from the group consisting of (i) an optionally halogenated $C_{1-4}$ alkyl group, (ii) a mono- or di-$C_{1-4}$ alkylamino-$C_{1-4}$ alkyl group, (iii) a carboxy- $C_{1-4}$ alkyl group, (iv) a $C_{1-4}$ alkoxy-carbonyl-$C_{1-4}$ alkyl group, (v) an optionally halogenated $C_{1-4}$ alkoxy group, (vi) a carboxy-$C_{1-4}$ alkoxy group, (vii) a $C_{1-4}$ alkoxy-carbonyl-$C_{1-4}$ alkoxy group, (viii) a halogen atom, (ix) a mono- or di-$C_{1-4}$ alkylamino group, (x) a $C_{1-4}$ alkoxy-carbonyl group and (xi) a carboxyl group,

(21) a compound as described in the above (1), wherein Ar is a phenyl group which may be substituted with (i) an optionally halogenated $C_{1-4}$ alkoxy group, (ii) a carboxyl group, (iii) a carboxyl-$C_{1-4}$ alkyl group, (iv) a mono- or di-$C_{1-4}$ alkylamino-$C_{1-4}$ alkyl group, (v) a mono- or di-$C_{1-4}$ alkylamino group and (vi) a carboxy-$C_{1-4}$ alkoxy group,

(22) a compound as described in the above (1), wherein Ar is a phenyl group which may be substituted with one or two of a $C_{1-6}$ alkyl group optionally substituted with (i) an amino, (ii) a mono- or di-$C_{1-4}$ alkylamino or (iii) 5- to 9-membered cyclic amino optionally substituted with a $C_{1-4}$ alkyl,

(23) a compound as described in the above (1), wherein Ar is a phenyl group which may be substituted with (i) an optionally halogenated $C_{1-4}$ alkoxy group or (ii) a mono- or di-$C_{1-4}$ alkylamino-$C_{1-4}$ alkyl group,

(24) a compound as described in the above (1), wherein Ar is a phenyl group which may be substituted with an optionally halogenated $C_{1-4}$ alkoxy group,

(25) a compound as described in the above (1), wherein Ar is a furyl, thienyl, pyrrolyl, oxazolyl, isoxazolyl, imidazolyl, pyrazolyl, pyridyl, pyridazinyl, quinolyl, isoquinolyl, indolyl, thiazolyl or thiadiazolyl group,

(26) a compound as described in the above (1), wherein Ar is an indolyl group,

(27) a compound as described in the above (1), wherein Q is an oxygen atom; R is a $C_{1-4}$ alkyl group; X is —NH—; and Y is —NH— or a bond,

(28) a compound represented by the formula:

$$\text{(I')}$$

[Structure: a bicyclic system with ring A' bearing a C(=Q)—N(R') group, connected to a central ring with ring B' substituent, and a =CH—CH$_2$—$X^a$—CO—$Y^a$—(CH$_2$)$_n$—Ar' chain]

wherein the ring A' and the ring B' each are a benzene ring which may be substituted with 1 or 2 substituents selected from the group consisting of a halogen atom, optionally halogenated $C_{1-4}$ alkyl and optionally halogenated $C_{1-4}$ alkoxy; Ar' is a phenyl group which may be substituted with 1 or 2 substituents selected from the group consisting of (i) an optionally halogenated $C_{1-4}$ alkyl, (ii) a mono- or di-$C_{1-4}$ alkylamino-$C_{1-4}$ alkyl, (iii) a carboxy-$C_{1-4}$ alkyl, (iv) a $C_{1-4}$ alkoxy-carbonyl-$C_{1-4}$ alkyl, (v) an optionally halogenated $C_{1-4}$ alkoxy, (vi) a carboxy-$C_{1-4}$ alkoxy, (vii) a $C_{1-4}$ alkoxy-carbonyl-$C_{1-4}$ alkoxy, (viii) a halogen atom, (ix) a mono- or di-$C_{1-4}$ alkylamino, (x) a $C_{1-4}$ alkoxy-carbonyl and (xi) a carboxyl; R' is a $C_{1-4}$ alkyl group; $X^a$ is —O— or —NR$^{1a}$—, wherein $R^{1a}$ is a hydrogen atom or a $C_{1-4}$ alkyl group; $Y^a$ is —O—, —NR$^{2b}$ wherein $R^{2b}$ is a hydrogen atom or a $C_{1-4}$ alkyl group, or a bond; and n is of the same meaning as defined above, or a pharmaceutically acceptable salt,

(29) a compound as described in the above (28), wherein $X^a$ and $Y^a$ are —NH—; and n is 0,

(30) a compound as described in the above (28), wherein $X^a$ is —NH—, $Y^a$ is a bond; and n is 1,

(31) a method for producing a compound represented by the formula:

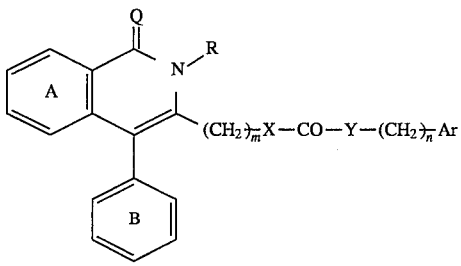

wherein the symbols are of the same meanings as defined in the above (1) or a salt thereof, which comprises reacting a compound represented by the formula:

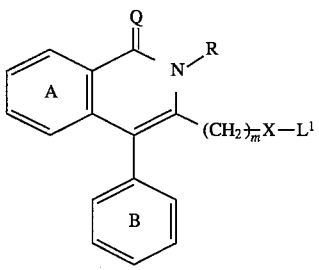

or a salt thereof, with a compound represented by the formula:

$$Ar\text{-}(CH_2)_n\text{-}Y\text{-}CO\text{-}L^2 \qquad (III)$$

wherein $L^1$ and $L^2$ each are a leaving group reacting each other, and other symbols are of the same meanings as defined in the above (1),

(32) a method for producing a compound represented by the formula:

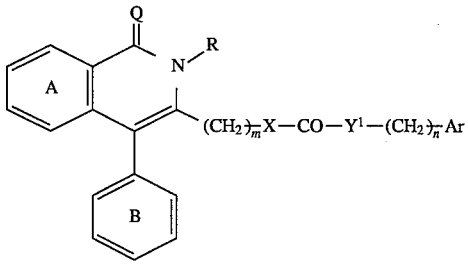

or a salt thereof, which comprises reacting a compound represented by the formula:

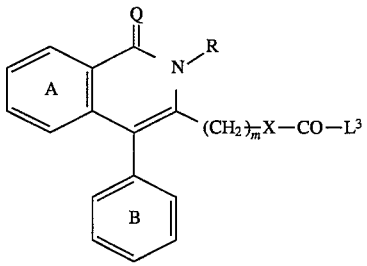

or a salt thereof, with a compound represented by the formula:

$$Ar\text{-}(CH_2)_n\text{-}Y^1\text{-}L^4 \qquad (V)$$

or a salt thereof, wherein $L^3$ and $L^4$ each are a leaving group reacting each other; $Y^1$ stands for —O— or —$NR^2$— and other symbols are of the same meanings as defined in the above (1),

(33) a pharmaceutical composition, especially suitable for calcium antagonist or substance P receptor antagonist activity, comprising a compound (I) or a pharmaceutically acceptable salt thereof with a pharmaceutically acceptable carrier or diluent.

Referring to the above formulae, ring A and ring B each stands for an optionally substituted benzene ring. Examples of substituents of the benzene ring include, among others, a halogen atom, optionally halogenated alkyl group, optionally halogenated alkoxy group, optionally halogenated alkylthio group, $C_{1-7}$ acylamino group (e.g. formylamino, acetylamino, propionylamino, butyrylamino, benzoylamino, etc.), $C_{1-3}$ acyloxy group (e.g. formyloxy, acetoxy, propionyloxy, etc.), hydroxyl group, nitro group, amino group, mono- or di-$C_{1-4}$ alkylamino group (e.g. methylamino, ethylamino, propylamino, dimethylamino, diethylamino, etc.), cyclic amino group (e.g. 5- to 9-membered cyclic amino group which may contain 1 to 3 hetero-atoms selected from the group consisting of oxygen atom and sulfur atom in addition to nitrogen atom, such as pyrrolidino, piperidino, morpholino, etc.), $C_{1-4}$ alkyl-carbonylamino group (e.g. acetylamino, propionylamino, butyrylamino, etc.), $C_{1-4}$ alkylsulfonylamino group (e.g. methylsulfonylamino, ethylsulfonylamino, etc.), $C_{1-4}$ alkoxy-carbonyl group (e.g. methoxycarbonyl, ethoxycarbonyl, propoxycarbonyl, etc.), carboxyl group, $C_{1-6}$ alkyl-carbonyl group (e.g. methylcarbonyl, ethylcarbonyl, propylcarbonyl, etc.), carbamoyl group, mono- or di-$C_{1-4}$ alkylcarbamoyl group (e.g. methylcarbamoyl, ethylcarbamoyl, etc.) and $C_{1-6}$ alkylsulfonyl group (e.g. methyl sulfonyl, ethylsulfonyl, propylsulfonyl, etc.).

Examples of the term "halogen atom" used in this specification include fluorine, chlorine and iodine, preferably chlorine and fluorine.

As the term "optionally halogenated alkyl group" used in this specification, use is often made of, for example, $C_{1-6}$ alkyl group or $C_{1-6}$ alkyl group which is substituted with 1 to 5 halogen atoms as mentioned hereinbefore, more specifically, for example, methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, 2-trifluoromethylethyl, butyl, 4,4,4-trifluorobutyl, isobutyl, sec-butyl, tertbutyl, pentyl, isopentyl, neopentyl, 5,5,5-trifluoropentyl, 4-trifluoromethylbutyl, hexyl, 6,6,6-trifluorohexyl, 5-trifluoromethylpentyl, and, use is preferably made of, for example, $C_{1-4}$ alkyl group or $C_{1-4}$ alkyl group which is substituted with 1 to 3 halogen atoms as mentioned hereinbefore such as methyl, chloromethyl, difluoromethyl, trichloromethyl, trifluoromethyl, ethyl, 2-bromoethyl, 2,2,2-trifluoroethyl, propyl, 3,3,3-trifluoropropyl, isopropyl, 2-trifluoromethylethyl, butyl, 4,4,4-trifluorobutyl, isobutyl, sec-butyl, tert-butyl. etc.

As the term "optionally halogenated alkoxy group" used in this specification, use is made of, for example, $C_{1-6}$ alkoxy group or $C_{1-6}$ alkoxy which is substituted with 1 to 5 halogen atoms as mentioned hereinbefore, for example, methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentoxy, hexyloxy, etc. are often used, and preferable examples include $C_{1-4}$ alkoxy group or $C_{1-4}$ alkoxy group which is substituted with 1 to 3 halogen atoms as mentioned hereinbefore such as methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, etc.

As the term "optionally halogenated alkylthio group" used in this specification, use is made of, for example, $C_{1-6}$ alkylthio group or $C_{1-6}$ alkylthio which is substituted with 1 to 5 of such halogen atoms as mentioned hereinbefore, and, for example, methylthio, difluoromethylthio, trifluoromethylthio, ethylthio, propylthio, isopropylthio, butylthio, 4,4,4-trifluorobutylthio, pentylthio, hexylthio, etc. are often employed, and, use is preferably made of, for example, $C_{1-4}$ alkylthio group or $C_{1-4}$ alkylthio group which is substituted with 1 to 3 halogen atoms as mentioned hereinbefore such as methylthio, difluoromethylthio, trifluoromethylthio, ethylthio, propylthio, isopropylthio, butylthio, 4,4,4-trifluorobutylthio, etc.

As examples of preferable substituents which the ring A and the ring B each may have include a halogen atom, optionally halogenated $C_{1-4}$ alkyl group (e.g. methyl, chloromethyl, difluoromethyl, trichloromethyl, trifluoromethyl, ethyl, 2-bromoethyl, 2,2,2-trifluoroethyl, propyl, isopropyl, etc.), hydroxyl group, optionally halogenated $C_{1-4}$ alkoxy group (e.g. methoxy, difluoromethoxy, trifluoromethoxy, ethoxy, 2,2,2-trifluoroethoxy, propoxy, isopropoxy, etc.), optionally halogenated $C_{1-4}$ alkylthio group (e.g. methylthio, difluoromethylthio, trifluoromethylthio, ethylthio, propylthio, etc.), amino group, mono- or di- $C_{1-4}$ alkylamino group (e.g. methylamino, ethylamino, propylamino, dimethylamino, diethylamino, etc.), carboxyl group, $C_{1-4}$ alkoxy-carbonyl group (e.g. methoxycarbonyl, ethoxycarbonyl, propoxycarbonyl, etc.), and, especially, a halogen atom (e.g. fluorine, chlorine, bromine, etc.), optionally halogenated $C_{1-4}$ alkyl group (e.g. methyl, chloromethyl, difluoromethyl, trichloromethyl, trifluoromethyl, ethyl, 2-bromoethyl, 2,2,2-trifluoromethyl, propyl, isopropyl, etc.), optionally halogenated $C_{1-4}$ alkoxy group (e.g. methoxy, difluoromethoxy, trifluoromethoxy, ethoxy, 2,2,2-trifluoroethoxy, propoxy, isopropoxy, etc.), etc. are employed.

The substituents on ring A and ring B may be substituted on any possible position of the ring, and two or more of such substituents may be the same or different, and the number of such substituents ranges from 1 to 4, preferably 1 to 3, and, especially those having 1 or 2 substituents are often used.

Referring to ring A, preferable examples of the partial moiety:

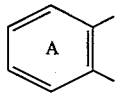

include a group of the formulae:

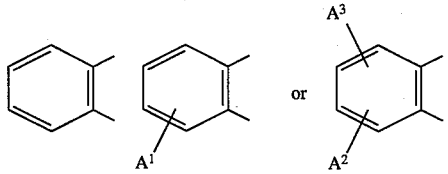

wherein $A^1$, $A^2$ and $A^3$ independently stand for a halogen atom such as chlorine, fluorine etc., an optionally halogenated $C_{1-4}$ alkyl group such as methyl, ethyl, isopropyl, trifluoromethyl, etc., or an optionally halogenated $C_{1-4}$ alkoxy group such as methoxy, trifluoromethoxy, ethoxy, etc.. Preferable examples of $A^1$, $A^2$ and $A^3$ include a halogen atom (e.g. fluorine, chlorine, bromine, etc.), an optionally halogenated $C_{1-4}$ alkyl group (e.g. methyl, trifluoromethyl, ethyl, etc.).

Referring to ring B, preferable examples of the partial moiety:

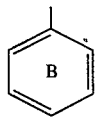

include a group of the formulae:

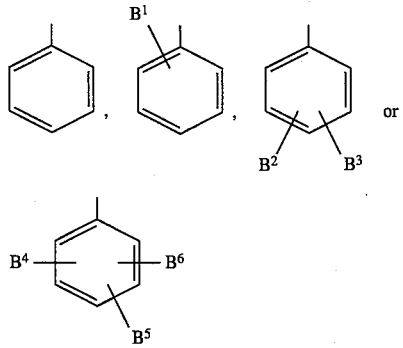

wherein $B^1$, $B^2$, $B^3$, $B^4$, $B^5$, and $B^6$ independently stand for a halogen atom such as chlorine, fluorine, etc., an optionally halogenated $C_{1-4}$ alkyl group such as methyl, trifluoromethyl, ethyl, etc. or an optionally halogenated $C_{1-4}$ alkoxy group such as methoxy, trifluoro methoxy, ethoxy, etc.

Referring to ring B, more preferable examples include a group of formulae:

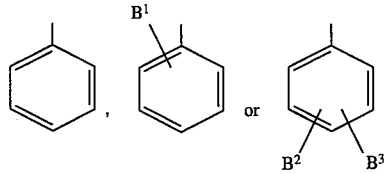

wherein $B^1$, $B^2$ and $B^3$ are of the same meaning as defined above. And, among them, preferable examples of $B^1$, $B^2$ and $B^3$ include a halogen atom such as fluorine, chlorine, bromine, etc., an optionally halogenated $C_{1-4}$ alkyl group such as methyl, trifluoromethyl, ethyl, etc.

More preferable example of ring B is unsubstituted benzene ring.

In the above-mentioned formulae, R stands for a hydrogen atom, an optionally substituted hydrocarbon group, an optionally substituted hydroxyl group or an optionally substituted amino group. As the "hydrocarbon group" of "optionally substituted hydrocarbon group" represented by R, use is made of, for example, a $C_{1-6}$ alkyl group, a $C_{3-6}$ cycloalkyl group or a $C_{3-6}$ cycloalkyl-$C_{1-4}$ alkyl group, etc. As the $C_{1-8}$ alkyl group, use is made of, for example, methyl, ethyl, propyl, isopropyl, butyl, isobutyl, sec-butyl, tert-butyl, pentyl, neopentyl, hexyl, etc., preferably, a $C_{1-4}$ alkyl group such as methyl, ethyl, propyl, isopropyl, butyl, isobutyl, sec-butyl, tert-butyl, etc. As the $C_{3-6}$ cycloalkyl group, use is made of, for example, cyclopropyl, cyclopentyl or cyclohexyl, etc.. As the $C_{3-6}$ cycloalkyl-$C_{1-6}$ alkyl group, use is made of, for example, cyclopropylmethyl, cyclopropylethyl, etc.. Preferable examples of such hydrocarbon groups include a $C_{1-6}$ alkyl group such as methyl, ethyl, propyl, isopropyl, butyl, etc.

As the substituents which the hydrocarbon group may have, use is made of 1 to 5, preferably 1 to 3 substituents selected from the group consisting of, for example, (a) a halogen atom (e.g. fluorine, chlorine, bromine, iodine, etc.), (b) nitro group, (c) cyano group, (d) hydroxyl group, (e) a $C_{1-4}$ alkoxy group (e.g. methoxy, ethoxy, propoxy, butoxy, isopropoxy, etc.), (f) a $C_{1-4}$ alkylthio group (e.g. methylthio, ethylthio, propylthio, etc.), (g) amino group, (h) a mono- or di- $C_{1-4}$ alkylamino group (e.g. methylamino, ethylamino, propylamino, dimethylamino, diethylamino, etc.), (i) a cyclic amino group which may be substituted with a $C_{1-4}$ alkyl group (e.g. The cyclic amino group stands for a 5- to 9-membered cyclic amino which may include 1 to 3 heteroatoms such as oxygen atom, sulfur atom, etc. other than nitrogen atom and carbon atom, specifically, for example, pyrrolidino, piperidino, piperazino, 4-methylpiperazino, morpholino, etc., The $C_{1-4}$ alkyl includes e.g. methyl, ethyl), (j) a $C_{1-4}$ alkylcarbonylamino group (e.g. acetylamino, propionylamino, butyrylamino, etc.), (k) a $C_{1-4}$ alkylsulfonylamino group (e.g. methylsulfonylamino, ethylsulfonylamino, etc.), (l) a $C_{1-4}$ alkoxy-carbonyl group (e.g. methoxycarbonyl, ethoxycarbonyl, propoxycarbonyl, etc.), (m) carboxyl group, (n) a $C_{1-6}$ alkyl-carbonyl group (e.g. methylcarbonyl, ethylcarbonyl, propylcarbonyl, etc.), (o) carbamoyl group, (p) a mono- or di- $C_{1-4}$ alkylcarbamoyl group (e.g. methylcarbamoyl, ethylcarbamoyl, etc.), (q) a $C_{1-6}$ alkylsulfonyl group (e.g. methylsulfonyl, ethylsulfonyl, propylsulfonyl, etc.) and (r) a phenyl group which may be substituted with a $C_{1-3}$ alkoxy group (e.g. o-, m- or p-methoxyphenyl, etc.).

Preferable examples of substituents which the hydrocarbon group represented by R may have include a halogen atom (e.g. fluorine, chlorine, bromine, etc.), a hydroxyl group, a $C_{1-4}$ alkoxy group (e.g. methoxy, ethoxy, propoxy, etc.), an amino group, a mono- or di- $C_{1-4}$ alkylamino group (e.g. methylamino, ethylamino, dimethylamino, diethylamino, etc.), a $C_{1-4}$ alkoxy-carbonyl group (e.g. methoxycarbonyl, ethoxycarbonyl, propoxycarbonyl, etc.), a carboxyl group, a carbamoyl group, a phenyl group, among others, especially a halogen atom (e.g. fluorine, chlorine, bromine, etc.), a carboxyl group, a carbamoyl group, etc. are often used. The number of these substituents is preferably 1 or 2.

As the "optionally substituted hydroxyl group" represented by R, mention is made of, for example, a hydroxyl group, a $C_{1-4}$ alkoxy group (e.g. methoxy, ethoxy, propoxy, isopropoxy, butoxy, t-butoxy, etc.), a $C_{6-10}$ aryloxy group (e.g. phenoxy, naphthyloxy, etc.), a $C_{1-4}$ alkyl-carbonyloxy group (e.g. formyloxy, acetoxy, propionyloxy, etc.), a $C_{6-10}$ aryl-carbonyloxy group (e.g. benzoyloxy, naphthoyloxy, etc.), etc. These groups may have some substituents. As such substituents, mention is made of the same kinds and numbers of the substituents which the "optionally substituted hydrocarbon group" represented by the above-mentioned R may have. As the "optionally substituted hydroxyl group", use is often made of a hydroxyl group or a $C_{1-4}$ alkoxy group (e.g. methoxy, ethoxy, propoxy, etc.).

As substituents of the "optionally substituted amino group" represented by R, use is made of (i) a $C_{1-4}$ alkyl group (e.g. methyl, ethyl, propyl, isopropyl, etc.), (ii) a $C_{1-4}$ alkyl—carbonyl group (e.g. acetyl, propionyl, butyryl, etc.), (iii) a $C_{1-4}$ alkoxy-carbonyl group (e.g. methoxycarbonyl, ethoxycarbonyl, propoxycarbonyl, etc.) or (iv) a phenyl group which may be substituted with halogen, $C_{1-4}$ alkyl group or $C_{1-4}$ alkoxy group (e.g. phenyl, 4-chlorophenyl, 3-chlorophenyl, 2-chlorophenyl, 4-methylphenyl, 3-methylphenyl, 2-methylphenyl, 4-methoxyphenyl, 3-methoxyphenyl, 2-methoxyphenyl, etc.). The amino group may have one or two of the above-mentioned substituents.

Preferable examples of R include a hydrogen atom, a $C_{1-4}$ alkyl group (e.g. methyl, ethyl, n-propyl, n-butyl, etc.), a hydroxyl group, a $C_{1-4}$ alkoxy group (e.g. methoxy, ethoxy, propoxy, etc.), an amino group, etc., especially preferably $C_{1-4}$ alkyl group (e.g. methyl, ethyl, n-propyl, etc.).

Q stands for oxygen atom or sulfur atom, with an oxygen atom being preferred.

In the above-mentioned formulae, X stands for —O— or —NR$^1$—, wherein R$^1$ stands for hydrogen atom or an optionally substituted hydrocarbon group.

Preferable examples of the hydrocarbon group represented by R$^1$ include a $C_{1-6}$ alkyl group, a $C_{3-6}$ cycloalkyl group or a $C_{3-6}$ cycloalkyl—$C_{1-4}$ alkyl group. As the $C_{1-6}$ alkyl group, use is made of, for example, methyl, ethyl, propyl, isopropyl, butyl, isobutyl, sec-butyl, tert-butyl, pentyl, neopentyl, hexyl etc., preferably $C_{1-4}$ alkyl group such as methyl, ethyl, propyl, isopropyl, butyl, isobutyl, sec-butyl, tert-butyl, etc. As the $C_{3-6}$ cycloalkyl group, use is made of, for example, cyclopropyl, cyclopentyl or cyclohexyl, etc.. As the $C_{3-6}$ cycloalkyl—$C_{1-4}$ alkyl group, use is made of, for example, cyclopropylmethyl, cyclopropylethyl, etc.

As the hydrocarbon group represented by R$^1$, $C_{1-4}$ alkyl groups (e.g. methyl, ethyl, propyl, isopropyl, butyl, etc.) is preferable.

As the substituents which the hydrocarbon group represented by R$^1$ may have, use is made of, for example, the same groups as "substituents" referred to in the "optionally substituted hydrocarbon groups" represented by R. Preferable examples of substituents of the hydrocarbon group represented by R$^1$ include a hydroxyl group, a $C_{1-4}$ alkoxy group (e.g. methoxy, ethoxy, propoxy, etc.), an amino group, a mono- or di- $C_{1-4}$ alkylamino group (e.g. methylamino, ethylamino, dimethylamino, diethylamino, etc.), a $C_{1-4}$ alkoxy-carbonyl group (e.g. methoxycarbonyl, ethoxycarbonyl, propoxycarbonyl, etc.), a carboxyl group, a carbamoyl group, a phenyl group, etc., especially, a $C_{1-4}$ alkoxy group (e.g. methoxy, ethoxy, etc.), a mono- or di- $C_{1-4}$ alkylamino group (e.g. dimethylamino), a carbamoyl group, a carboxyl group, a $C_{1-4}$ alkoxy-carbonyl group (e.g. methoxycarbonyl, ethoxycarbonyl). The number of the substituents is preferably 1 or 2. R is preferably a hydrogen atom. X is preferably —NH—.

In the above-mentioned formulae, Ar stands for an optionally substituted aryl group or an optionally substituted heterocyclic group. As "aryl group" of "optionally substituted aryl group" represented by Ar, a $C_{6-10}$ aryl group such as phenyl, naphthyl is preferable, especially a phenyl group is more preferable. The aryl group group represented by Ar may have the same or different 1 to 5 substituents (preferably 1 to 3 substituents), and at any position of those rings. Examples of such substituents include (a) a halogen atom (e.g. fluorine, chlorine, bromine, iodine, etc.), (b) a nitro group, (c) a cyano group, (d) a hydroxyl group, (e) an optionally halogenated $C_{1-4}$ alkoxy group, (f) a $C_{1-4}$ alkoxy group which may be substituted with a carboxyl group (e.g. carboxymethoxy, 2-(carboxy)ethoxy, etc.), (g) a $C_{1-4}$ alkoxy group which may be substituted with a $C_{1-4}$ alkoxy-carbonyl group (e.g. methoxycarbonylmethoxy, ethoxycarbonylmethoxy, 2-(methoxycarbonyl)ethoxy, 2-(ethoxycarbonyl)ethoxy, etc.), (h) an optionally halogenated $C_{1-4}$ alkylthio group, (i) an amino group, (j) a mono- or di- $C_{1-4}$ alkylamino group (e.g. methylamino, ethylamino, propylamino, dimethylamino, diethylamino, etc.), (k) a cyclic amino group which may be substituted with $C_{1-4}$ alkyl groups (e.g. The cyclic amino group is a 5- to 9- membered cyclic amino group optionally containing 1 to 3 hetero-atoms such as oxygen atom, sulfur atom, other than nitrogen atom, specifically, for example, pyrrolidino, piperidino, piperazino, 4-methylpiperazino, morpholino, etc. The $C_{1-4}$ alkyl includes methyl, ethyl propyl.), (l) a $C_{1-4}$ alkylcarbonylamino group (e.g. acetylamino, propionylamino, butyrylamino, etc.), (m) an aminocarbonyloxy group, (n) a mono- or di- $C_{1-4}$ alkylaminocarbonyloxy group (e.g. methylaminocarbonyloxy, ethylaminocarbonyloxy, dimethylaminocarbonyloxy, diethylaminocarbonyloxy, etc.), (o) a $C_{1-4}$ alkylsulfonylamino group (e.g. methylsulfonylamino, ethylsulfonylamino, propylsulfonylamino, etc.), (p) a $C_{1-4}$ alkoxy-carbonyl group (e.g. methoxycarbonyl, ethoxycarbonyl, propoxycarbonyl, isobutoxycarbonyl, etc.), (q) a benzyloxycarbonyl group, (r) a carboxyl group, (s) a $C_{1-4}$ alkyl -carbonyl group (e.g. methylcarbonyl, ethylcarbonyl, butylcarbonyl, etc.), (t) a $C_{3-6}$ cycloalkyl—carbonyl group (e.g. cyclohexylcarbonyl, etc.), (u) a carbamoyl group, (v) a mono- or di- $C_{1-4}$ alkylcarbamoyl group (e.g. methylcarbamoyl, ethylcarbamoyl, propylcarbamoyl, butylcarbamoyl, diethylcarbamoyl, dibutylcarbamoyl, etc.), (w) a $C_{1-6}$ alkylsulfonyl group (e.g. methylsulfonyl, ethylsulfonyl, propylsulfonyl, etc.) or (x) an optionally substituted hydrocarbon group, among others. As the optionally substituted hydrocarbon group, use is made of, for example, "optionally substituted hydrocarbon group" represented by R. Further, the "optionally substituted heterocyclic group" represented by Ar described later, can be used also for the substituents of the aryl group. Preferable examples of these optionally substituted heterocyclic group include a 5- or 6-membered aromatic monocyclic heterocyclic group which may be substituted with 1 to 3 substituents selected from the group consisting of an optionally halogenated $C_{1-4}$ alkyl group (e.g. methyl, chloromethyl, difluoromethyl, trichloromethyl, trifluoromethyl, ethyl, 2-bromoethyl, 2,2,2-trifluoroethyl, propyl, 3,3,3-trifluoropropyl, butyl, etc.), a $C_{3-6}$ cyclaalkyl group (e.g. cyclopropyl, cyclobutyl, cyclopentyl, cyclohexyl, etc.), a halogen atom (e.g. fluorine, chlorine, bromine, iodine, etc,), a hydroxyl group, an optionally halogenated $C_{1-4}$ alkoxy groups (e.g. methoxy, difluoromethoxy, trifluoromethoxy, ethoxy, 2,2,2-trifluoroethoxy, propyloxy, butyloxy, isopropyloxy, etc.), an optionally halogenated $C_{1-4}$ alkylthio group (e.g. methylthio, difluromethylthio, trifluoromethylthio, ethylthio, propylthio, isopropylthio, butylthio, etc.), an amino group, a mono- or di- $C_{1-4}$ alkylamino group (e.g. methylamino, ethylamino, propylamino, dimethylamino, diethylamino, etc.), a $C_{1-4}$ alkoxy-carbonyl group (e.g. methoxycarbonyl, ethoxycarbonyl, propoxycarbonyl, isobutoxycarbonyl, etc.), a carboxyl group and a $C_{1-6}$ alkyl—carbonyl group (e.g. methylcarbonyl, ethylcarbonyl, butylcarbonyl, etc.). The 5- or 6-membered aromatic monocyclic heterocyclic group include furyl, thienyl, oxazolyl, isoxazolyl, thiazolyl, isothiazolyl, imidazolyl, pyrazolyl, 1,2,3-oxadiazolyl, 1,2,4-oxadiazolyl, 1,3,4-oxazolyl, furazanyl, 1,2,3-thiadiazolyl, 1,2,4-thiazolyl, 1,3,4-thiadiazolyl, 1,2,3-triazolyl, 1,2,4-triazolyl, pyridyl, pyridazinyl, pyrimidinyl, pyrazinyl, triazinyl, etc.

preferable examples of substituents on the "aryl group" represented by Ar include (i) an optionally halogenated $C_{1-4}$ alkyl group (e.g. methyl, chloromethyl, bromomethyl, difluoromethyl, trichloromethyl, trifluoromethyl, ethyl, 2-bromoethyl, 2,2,2-trifluoroethyl, propyl, isopropyl, 3,3,3-trifluoropropyl, etc.), (ii) a halogen atom (e.g. fluorine, chlorine, bromine, etc.), (iii) a $C_{1-4}$ alkyl group which may be substituted with an amino or a mono- or di- $C_{1-4}$ alkylamino (e.g. aminomethyl, methylaminomethyl, ethylaminomethyl, dimethylaminomethyl, diethylaminomethyl, 2-aminoethyl, 2-(methylamino)ethyl, 2-(dimethylamino)ethyl, 2-(diethylamino)ethyl, etc.), (iv) a $C_{1-4}$ alkyl group which may be substituted with a cyclic amino group optionally substituted a $C_{1-4}$ alkyl (e.g. pyrrolidinomethyl, 2-pyrrolidinoethyl, piperidinomethyl, 2-piperidinoethyl, piperazinomethyl, 2-piperazinoethyl, 4-methylpiperadinomethyl, 2-(4-methylpiperazino)ethyl, morpholinomethyl, 2-morpholinoethyl, etc. The cyclic amino group is a 5 to 7-membered cyclic amino group optionally containing 1 or 2 hetero atoms such as oxygen atom or sulfur atom other than nitrogen atom such as pyrrolidino, piperidino, piperazino, morphorino. The $C_{1-4}$ alkyl includes methyl, ethyl, propyl.), (v) a $C_{1-4}$ alkyl group which may be substituted with a carboxyl group (e.g. carboxylmethyl, 2-carboxylethyl, etc.), (vi) a $C_{1-4}$ alkyl group which may be substituted with a $C_{1-4}$ alkoxy-carbonyl group (e.g. methoxycarbonylethyl, 2-ethoxycarbonylethyl, etc.), (vii) a $C_{1-4}$ alkyl group which may be substituted with a hydroxyl group (e.g. hydroxymethyl, 2-hydroxyethyl, etc.), (viii) a hydroxyl group, (ix) an optionally halogenated $C_{1-4}$ alkoxy group (e.g. methoxy, difluoromethoxy, trifluoromethoxy, ethoxy, propoxy, isopropoxy, n-butoxy, t-butoxy, 2,2,2-trifluoroethoxy, etc.), (x) a $C_{1-4}$ alkoxy group which may be substituted with a carboxyl group (e.g. carboxymethoxy, 2-carboxyethoxy, etc.), (xi) a $C_{1-4}$ alkoxy group which may be substituted with a $C_{1-4}$ alkoxy-carbonyl group (e.g. methoxycarbonylmethoxy, ethoxycarbonylmethoxy, 2-(methoxycarbonyl)ethoxy, 2-(ethoxycarbonyl)ethoxy, etc.), (xii) a $C_{1-4}$ alkylthio groups (e.g. methylthio, ethylthio, etc.), (xiii) an amino group, (xiv) a mono- or di- $C_{1-4}$ alkylamino group (e.g. methylamino, ethylamino, dimethylamino, diethylamino, etc.), (xv) a $C_{1-4}$ alkoxy-carboxyl group (e.g. methoxycarbonyl, ethoxycarbonyl, etc.), (xvi) a carboxyl group, (xvii) carbamoyl group, etc. The number of the substituents is 1 to 3.

Preferable examples of the substituents of the "aryl group" represented by Ar is (i) to (xi) described hereinabove, more preferably, (iii), (iv), (vi), (vii), (ix), (xi) described hereinabove.

As the "heterocyclic group" of the "optionally substituted heterocyclic group represented by Ar, use is made of, for example, 5- to 9-membered, preferably 5- or 6-membered aromatic heterocyclic group optionally containing 1 to 4, preferably 1 or 2 hetero-atoms such as nitrogen, oxygen and sulfur, atoms, etc. other than carbon atom. Examples of these aromatic heterocyclic groups include aromatic monocyclic heterocyclic groups such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, etc., preferably, for example, furyl, thienyl, pyrrolyl, oxazolyl, isoxazolyl, imidazolyl, pyrazolyl, pyridyl, pyridazinyl, quinolyl, isoquinolyl, thiazolyl, thiazolyl, thiophenyl, etc., especially furyl, thienyl, pyridyl, etc. are often used. And, the aromatic condensed heterocyclic groups such as benzofuranyl, isobenzofuranyl, benzo[b]thienyl, indolyl, isoindolyl, 1H-indazolyl, benzoimidazolyl, benzoxazolyl, 1,2-benzoisoxazolyl, benzothiazolyl, 1,2-benzoisothiazolyl, 1H-benzotriazolyl, quinolyl, isoquinolyl, cinnolinyl, quinazolinyl, quinoxalinyl, phthalazinyl, naphthylidinyl, purinyl, pteridinyl, carbazolyl, α-carbonyl, β-carbolinyl, γ-carbolinyl, acrydinyl, phenoxazinyl, phenothiazinyl, phenazinyl, phenoxathiinyl, thiantrenyl, phenathrolinyl, indolidinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl are often used, too. Preferable examples are benzyofuranyl, indolyl, benzoimidazolyl, benzoxazolyl, quinolyl, etc., more preferably indolyl.

As the substituents of "optionally substituted heterocyclic group" represented by Ar, mention is made of the same kinds of the substituents mentioned hereinabove for aryl group represented by Ar, and a number of the substituents is 1 to 3.

Preferable examples of the substituents of heterocyclic group represented by Ar include (i) a halogen atom (e.g. fluorine, chlorine, bromine, etc.), (ii) an optionally halogenated $C_{1-4}$ alkyl group (e.g. methyl, chloromethyl, difluoromethyl, trifluoromethyl, ethyl, etc.), (iii) a $C_{3-6}$ cycloalkyl group (e.g. cyclopropyl, cyclobutyl, etc.), (iv) a $C_{1-4}$ alkyl group which is substituted with an amino or a mono- or di- $C_{1-4}$ alkylamino (e.g. aminomethyl, methylaminomethyl, ethylaminomethyl, dimethylaminomethyl, diethylaminomethyl, 2-aminoethyl, 2-(methylamino)ethyl, 2-(ethylamino)ethyl, 2-(dimethylamino)ethyl, 2-(diethylamino)ethyl, etc.), (v) a $C_{1-4}$ alkyl group which is substituted with a cycliamino which may be substituted with a $C_{1-4}$ alkyl (e.g. pyrrolidinomethyl, 2-pyrrolidinoethyl, piperidinomethyl, 2-piperidinoethyl, piperazinomethyl, 2-piperazinoethyl, 4-methylpiperazinomethyl, 2-(4-methylpiperazino)ethyl, morphorinomethyl, 2-morphorinoethyl, etc. The cyclic amino group is a 5- to 7- membered cyclic amino group optionally containing 1 or 2 hetero atoms such as oxygen atom or sulfur atom other than nitrogen atom such as pyrrolidino, piperidino, piperazino, morphorino. The $C_{1-4}$ alkyl includes methyl, ethyl, propyl.), (vi) a $C_{1-4}$ alkyl group which substituted with a carboxyl (e.g. carboxymethyl, carboxyethyl, etc.), (vii) a $C_{1-4}$ alkyl group which is substituted with a $C_{1-4}$ alkoxycarbonyl (e.g. methoxycarbonylethyl, ethoxycarbonylethyl, etc.), (viii) a $C_{1-4}$ alkyl group which is substituted with a hydroxyl (e.g. hydroxymethyl, 2-hydroxyethyl, etc.), (ix) a hydroxyl group, (x) an optionally halogenated $C_{1-4}$ alkoxy group (e.g. methoxy, difluoromethoxy, trifluoromethoxy, ethoxy, propoxy, isopropoxy, etc.), (xi) an amino group, (xii) a mono- or di- $C_{1-4}$ alkylamino group (e.g. methylamino, ethylamino, dimethylamino, diethylamino, etc.), (xiii) a $C_{1-4}$ alkoxy-carbonyl group (e.g. methoxycarbonyl, ethoxycarbonyl, etc.), (xiv) a carboxyl group.

Preferable examples of Ar are a phenyl group which may be substituted with 1 or 2 substituents selected from the group consisting of (a) an optionally halogenated $C_{1-4}$ alkyl group (e.g. methyl, chloromethyl, bromomethyl, difluoromethyl, trifluoromethyl, ethyl, 2,2,2-trifluoroethyl, propyl, isopropyl, etc.), (b) an optionally halogenated $C_{1-4}$ alkoxy group (e.g. methoxy, difluoromethoxy, trifluoromethoxy, ethoxy, 2,2,2-trifluoroethoxy, propoxy, isopropoxy, etc.), (c) a $C_{1-4}$ alkoxy group which is substituted with a carboxyl (e.g. carboxymethoxy, 2-carboxyethoxy, etc.), (d) a $C_{1-4}$ alkoxy group which is substituted with a $C_{1-4}$ alkoxycarbonyl (e.g. methoxycarbonylmethoxy, ethoxycarbonylmethoxy, 2-(methoxycarbonyl)ethoxy, 2-(ethoxycarbonyl)ethoxy, etc.), (e) a $C_{1-4}$ alkyl group which is substituted with an amino or a mono- or di- $C_{1-4}$ alkylamino (e.g. aminomethyl, methylaminomethyl, ethylaminomethyl, dimethylaminomethyl, diethylaminomethyl, 2-aminoethyl, 2-(methylamino)ethyl, 2-(ethylamino)ethyl, 2-(dimethylamino)ethyl, 2-(diethylamino)ethyl, etc.), (f) a $C_{1-4}$ alkyl group which is substituted with a cyclic amino group which may be substituted with a $C_{1-4}$ alkyl (e.g. pyrrolidinomethyl, 2-pyrrolidinoethyl, piperidinomethyl, 2-piperidinoethyl, piperazinomethyl, 2-piperazinoethyl, 4-methylpiperazinomethyl, 2-(4-methylpiperazino)ethyl, morphorinomethyl, 2-morphorinoethyl, etc. The cyclic amino group is a 5- to 7- membered cyclic amino group optionally containing 1 or 2 hetero atoms such as oxygen atom or sulfur atom other than nitrogen atom such as pyrrolidino, piperidino, piperazino, morphorino. The $C_{1-4}$ alkyl includes methyl, ethyl, propyl.), (g) a $C_{1-4}$ alkyl group which is substituted with a carboxyl (e.g. carboxymethyl, 2-carboxyethyl, etc.), (h) a $C_{1-4}$ alkyl group which is substituted with a $C_{1-4}$ alkoxy-carbonyl (e.g. methoxycarbonylethyl, 2-ethoxycarbonylethyl, etc.), (i) a $C_{1-4}$ alkyl group which is substituted with a hydroxyl (e.g. hydroxymethyl, 2-hydroxyethyl, etc.), (j) an amino group, (k) a mono- or di- $C_{1-4}$ alkylamino group (e.g. methylamino, ethylamino, dimethylamino, diethylamino, etc.), (l) a $C_{1-4}$ alkoxycarbonyl group (e.g. methoxycarbonyl, ethoxycarbonyl, etc.) and (m) a carboxyl group.

In the above-mentioned formulae, Y stands for —O—, —$NR^2$—, wherein $R^2$ stands for hydrogen atom or an optionally substituted hydrocarbon group, or a bond. As the "optionally substituted hydrocarbon group" represented by $R^2$, use is made of, for example, those described for $R^1$ of the group —$NR^1$— in the above-mentioned X. Preferable examples of the hydrocarbon group represented $R^2$ are a $C_{1-4}$ alkyl group (e.g. methyl, ethyl, propyl, etc.) and so on. As preferable examples of substituents which the hydrocarbon group represented by $R^2$ may have, mention is made of, for example, a hydroxyl group, a $C_{1-4}$ alkoxy group (e.g. methoxy, ethoxy, propoxy, isopropoxy, etc.), an amino group, a mono- or di-$C_{1-4}$ alkylamino group (e.g. methylamino, ethylamino, dimethylamino, diethylamino, etc.), a $C_{1-4}$ alkoxy-carbonyl group (e.g. methoxycarbonyl, ethoxycarbonyl, propoxycarbonyl, etc.), a carboxyl group, a carbamoyl group, a phenyl group, etc., especially a $C_{1-4}$ alkoxy groups (e.g. methoxy, ethoxy, propoxy, isopropoxy, etc.), a mono- or di- $C_{1-4}$ alkylamino group (e.g. methylamino, dimethylamino, etc.), a carbamoyl group, a $C_{1-4}$ -alkoxycarbonyl group (e.g. methoxycarbonyl, ethoxycarbonyl etc.), etc. are often employed. Preferable examples of $R^2$ are a hydrogen atom and a $C_{1-4}$ alkyl group (e.g. methyl, ethyl, propyl, etc.).

In the above-mentioned formulae, m denotes 1, 2 or 3, and n denotes 0, 1 or 2.

Hereinafter, preferable examples of each moiety of the compound [I] or a salt thereof are set forth.

1) Ring A:

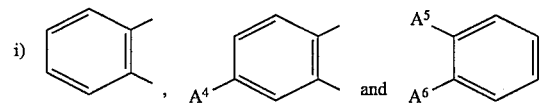

wherein $A^4$, $A^5$ and $A^6$ respectively stand for a halogen atom (e.g. fluorine, chlorine, etc.), an optionally halogenated $C_{1-4}$ alkyl group (e.g. methyl, chloromethyl, difluoromethyl, trifluoromethyl, ethyl, propyl, isopropyl, etc.) or an optionally halogenated $C_{1-4}$ alkoxy groups (e.g. methoxy, trifluoromethoxy, ethoxy, propoxy, isopropoxy, etc.), or

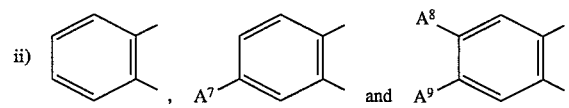

wherein $A^7$ stands for a halogen atom (e.g. chlorine, fluorine, etc.), $A^8$ and $A^9$ respectively stand for an optionally halogenated $C_{1-4}$ alkyl group (e.g. methyl, trifluoromethyl, ethyl, propyl, etc.).

2) Ring B:

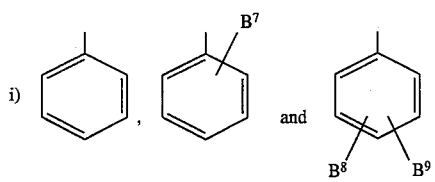

wherein $R^7$, $R^8$ and $R^9$ respectively stand for a halogen atom (e.g. fluorine, chlorine, etc.), an optionally halogenated $C_{1-4}$ alkyl group (e.g. methyl, chloromethyl, difluoromethyl, trifluoromethyl, ethyl, propyl, isopropyl, etc.) or an optionally halogenated $C_{1-4}$ alkoxy group (e.g. methoxy, trifluoromethoxy, ethoxy, propoxy, isopropoxy, etc.),

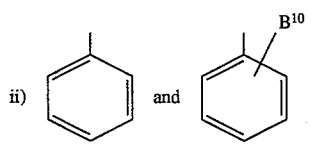

wherein $B^1$ stands for a halogen atom (e.g. fluorine, chlorine, etc.) or an optionally halogenated $C_{1-4}$ alkyl group (e.g. methyl, chloromethyl, trifluoromethyl, ethyl, propyl, etc.) or
iii) unsubstituted benzene ring 3) R:
  i) a hydrogen atom or
  ii) a $C_{1-4}$ alkyl group (e.g. methyl, ethyl, propyl, etc.)
4) Q: oxygen atom
5) x:
  i) $-NR^{1a}-$
  wherein $R^{1a}$ stands for a hydrogen atom or a $C_{1-4}$ alkyl group (e.g. methyl, ethyl, propyl, etc.),
  ii) $-O-$ or
  iii) $-NH-$
6) Y:
  i) $-NR^{2a}-$
  wherein $R^{2a}$ stands for a hydrogen atom or a $C_{1-4}$ alkyl group which may be substituted with a $C_{1-4}$ alkoxy —carbonyl group (e.g. methoxycarbonyl, ethoxycarbonyl, etc.) or a carboxyl group
  ii) $-NR^{2b}-$
  wherein $R^{2b}$ stands for a hydrogen atom or a $C_{1-4}$ alkyl group (e.g. methyl, ethyl, etc.)
  iii) $-NH-$
  iv) a bond or
  v) $-O-$:
7) m:
  i) 1 or
  ii) 2
8) n:
  i) 0 or
  ii) 1
9) Ar:
  i) a phenyl group which may be substituted with 1 or 2 substituents selected from the group consisting of (a) an optionally halogenated $C_{1-4}$ alkyl group (e.g. methyl, chloromethyl, bromomethyl, difluoromethyl, trifluoromethyl, ethyl, 2,2,2-trifluoroethyl, propyl, isopropyl, etc.), (b) a $C_{1-4}$ alkyl group which is substituted with an amino or a mono- or di- $C_{1-4}$ alkylamino group (e.g. aminomethyl, methylaminomethyl, ethylaminomethyl, dimethylaminomethyl, diethylaminomethyl, 2-aminoethyl, 2-(methylamino)ethyl, 2-(ethylamino)ethyl, 2-(dimethylamino)ethyl, 2 -diethylamino)ethyl, etc.), (c) a $C_{1-4}$ alkyl group which is substituted with a cyclic amino group which may be substituted with a $C_{1-4}$ alkyl (e.g. pyrrolidinomethyl, 2-pyrrolidinoethyl, piperidinomethyl, 2-piperidinoethyl, piperazinomethyl, 2-piperazinoethyl, 4-methylpiperazinomethyl, 2-(4-methylpiperazino)ethyl, morphorinomethyl, 2-morphorinoethyl, etc. The cyclic amino group is a 5- to 7-membered cyclic amino group optionally containing 1 or 2 hetero atoms such as oxygen atom or sulfur atom other than nitrogen atom such as pyrrolidino, piperidino, piperazino, morphorino. The $C_{1-4}$ alkyl includes methyl, ethyl, propyl.), (d) a $C_{1-4}$ alkyl group which is substituted with a carboxyl (e.g. carboxymethyl, carboxyethyl, etc.), (e) a $C_{1-4}$ alkyl group which is substituted with a $C_{1-4}$ alkoxy-carbonyl group (e.g. methoxycarbonylethyl, ethoxycarbonylethyl, etc.), (f) an optionally halogenated a $C_{1-4}$ alkoxy group (e.g. methoxy, difluoromethoxy, trifluoromethoxy, ethoxy, 2,2,2-trifluoroethoxy, propoxy, isopropoxy, etc.), (g) a $C_{1-4}$ alkoxy group which is substituted with a carboxyl group (e.g. carboxymethoxy, 2-carboxyethoxy, etc.), (h) a $C_{1-4}$ alkoxy group which is substituted with a $C_{1-4}$ alkoxy-carbonyl group (e.g. methoxycarbonylmethoxy, ethoxycarbonylmethoxy, 2-(methoxycarbonyl)ethoxy, etc.), (i) a halogen atom (e.g. fluorine, chlorine, bromine, etc.), (j) a mono- or di- $C_{1-4}$ alkylamino group (e.g. methylamino, ethylamino, dimethylamino, diethylamino, etc.), (k) a $C_{1-4}$ alkoxy-carbonyl group (e.g. methoxycarbonyl, ethoxycarbonyl, etc.) and (1) carboxyl group, ii) a phenyl group which may be substituted a substituent selected from the group consisting of (a) a $C_{1-4}$ alkoxy group (e.g. methoxy, ethoxy, propoxy, isopropoxy, etc.), (b) a carboxyl group, (c) a $C_{1-4}$ alkyl group which is substituted with a carboxyl group (e.g. carboxymethyl, carboxyethyl, etc.), (d) a $C_{1-4}$ alkyl group which is substituted with an amino or a mono- or di- a $C_{1-4}$ alkylamino groups (e.g. aminomethyl, methylaminomethyl, ethylaminomethyl, dimethylaminomethyl, diethylaminomethyl, 2-aminoethyl, 2-(methylamino)ethyl), 2-(dimethylamino)ethyl, 2-(diethylamino)ethyl, etc.), (r) a mono- or di- a $C_{1-4}$ alkylamino group (e.g. methylamino, ethylamino, dimethylamino, diethylamino, etc.) and (f) a $C_{1-4}$ alkoxy group which is substituted with a carboxyl group (e.g. carboxymethoxy, 2-carboxyethoxy, etc.), iii) a phenyl group which may be substituted with a substituent selected from the group consisting of (a) a $C_{1-4}$ alkoxy groups (e.g. methoxy, ethoxy, propoxy, isopropoxy, etc.) and (b) a $C_{1-4}$ alkyl group which is substituted with an amino or a mono- or di- $C_{1-4}$ alkylamino group (e.g. aminomethyl, methylaminomethyl, ethylaminomethyl, dimethylaminomethyl, diethylaminomethyl, 2-aminoethyl, 2-(methylamino)ethyl, 2-(dimethylamino)ethyl, 2-(dimethylamino)ethyl, etc.), iv) a phenyl groups which may be substituted with a $C_{1-4}$ alkoxy group (e.g. methoxy, ethoxy, propoxy, isopropoxy, etc.), v) a furyl, thienyl, pyrrolyl, oxazolyl, isoxazolyl, imidazolyl, pyrazolyl, pyridyl, pyridazinyl, quinolyl, isoquinolyl, indolyl, thiazolyl, thiadiazolyl or thiophenyl group, vi) an indolyl group.

And, preferable examples of the compound (I) or salts thereof include those having preferable ones of ring A, ring B, Ar, m and n as described above, and Q, R, X and Y stand for those set forth below;

1) Q stands for an oxygen atom, R stands for an optionally halogenated $C_{1-4}$ alkyl group (e.g. methyl, ethyl, propyl, etc.), X stands for —NH— and Y stands for —NH— or a bond, 2) Q stands for an oxygen atom, R stands for an optionally halogenated $C_{1-4}$ alkyl group (e.g. methyl, ethyl, propyl, etc.), X stands for —$NR^{1a}$—, wherein $R^{1a}$— is of the same meaning as defined above, and Y stands for —$NR^{2b}$—, wherein $R^{2b}$ is of the same meaning as defined above, 3) Q stands for an oxygen atom, R stands for an optionally halogenated $C_{1-4}$ alkyl group (e.g. methyl, ethyl, propyl, etc.), X stands for —NH— and Y stands for a bond, 4) Q stands for an oxygen atom, R stands for an optionally halogenated $C_{1-4}$ alkyl group (e.g. methyl, ethyl, propyl, etc.), X stands for —$NR^{1a}$—, wherein $R^{1a}$ is of the same meaning as defined above, 5) Q stands for an oxygen atom, R stands for an optionally halogenated $C_{1-4}$ alkyl group (e.g. methyl, ethyl, propyl, etc.), X stands for —O—, and Y stands for —NH—, and (6) Q stands for an oxygen atom, R stands for an optionally halogenated $C_{1-4}$ alkyl group (e.g. methyl, ethyl, propyl, etc.), X stands for —O— and Y stands for a bond.

In the above-mentioned formulae, $L^1$ and $L^2$, and $L^3$ and $L^4$ respectively stand for a leaving group by reacting together. More specifically, $L^1$ and $L^3$ stand for, for example a hydrogen atom, while $L^2$ and $L^4$ stand for, for example a hydroxyl, a halogen atom (e.g. chlorine, bromine, iodine, etc.), an acyloxy group (e.g. acetoxy, benzoyloxy, etc.), an oxy group which is substituted with a hetero-ring or an aryl group (e.g. succinimidoxy, benzotriazolyloxy, 1-ethoxycarbonyl-1,2 -dihydroquinoline-2-oxy, 4-nitrophenoxy, etc.).

When a compound (I) and (I-1) of this invention have a basic group such as an amino group or a substituted amino group, a compound (I) and (I-1) may form a physiologically acceptable acid addition salt. As such a salt, use is made of, for example, a salt with an inorganic acid (e.g. hydrochloric acid, phosphoric acid, hydrobromic acid, sulfuric acid) or a salt with an organic acid (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid). Further, when a compound (I) and (I-1) have an acid group such as —COOH, a compound (I) and (I'-1) may form a salt with an inorganic base (e.g. an alkali metal or alkaline earth metal such as sodium potassium, magnesium, etc., ammonia) or an organic base (e.g. tri- $C_{1-3}$ alkylamine such as triethylamine, etc.).

The following is a description of the method of producing a compound (I) or a salt thereof of this invention.

A compound (I) or (I-1) of this invention or a salt thereof can be produced by, for example, reacting: Method (1): an isoquinoline derivative (II) or a salt thereof with a compound (III) or a salt thereof or Method (2): an isoquinoline derivative (IV) or a salt thereof with a compound (V) or a salt thereof.

The above Method (1) and (2) are now described in detail. Method (1): This method is an acylation reaction which comprises reacting the compound (II) or a salt thereof, wherein X stands for —O—, i.e. an alcohol derivative, and X stands for —$NR^1$—, i.e. amine derivative, with the compound (III) or a salt thereof.

In this acylation reaction, when the leaving group $L^2$ of compound (III) or a salt thereof is a hydroxyl group, it is preferable to use an appropriate condensing agent or to convert the leaving hydroxyl group to another leaving group as appropriate (e.g. an acyloxy group as described above, or an oxy group substituted by a heterocyclic group or aryl group) and then react it with compound (II) or a salt thereof. Such condensing agents include dicylohexylcarbodiimide (DCC), diethyl cyanophosphate (DEPC) and diphenylphosphorylazide (DPPA). When these condensing agents are used, the reaction is preferably carried out in a solvent (e.g. ethers, esters, hydrocarbons, amides, sulfoxides such as tetrahydrofuran, dioxane, dimethoxyethane, ethyl acetate, benzene, toluene, N,N-dimethylformamide and dimethylfulfoxide). This reaction may be accelerated in the presence of a base, and is carried out at about −10° to 100° C., preferably about 0° to 60° C. Reaction time is normally 5 minutes to 96 hours, preferably 0.5 to 72 hours. The amount of compound (III) or a salt thereof or condensing agent used is 1 to 5 mol equivalents, preferably 1 to 3 mol equivalents per mol of compound (II) or a salt thereof. Examples of bases which can be used include alkylamines such as triethylamine and cyclic amines such as N-methylmorpholine and pyridine, their amount being 1 to 5 equivalents, preferably 1 to 3 mol equivalents per mol of compound (II) or a salt thereof.

The compound (III) may also be employed as a reactive derivative at the carboxyl group of the carboxylic acid in which $L^2$ stands for hydroxyl group. As these reactive derivatives, use is made of, for example, an acid halide (e.g. chloride, bromide, etc.), an acid anhydride, a mixed acid anhydride, (e.g. an anhydride with methyl carbonate, an anhydride with ethyl carbonate, an anhydride with isobutyl carbonate, etc.),an active ester (e.g. a ester with hydroxysuccinic imide, an ester with 1 -hydroxybenzotriazole, an ester with N-hydroxy-5 -norbornene-2,3-dicarboxyimide, an ester with p-nitrophenol, an ester with 8-oxyquinoline, etc.), among others, especially an acid halide ($L^2$ is halogen atom) is preferable. In the compound (III), when Y is —NH—, it is preferable to use the compound (III) as an isocyanate derivative formed by eliminating H-$L^2$ from the compound (III). The reaction between the compound (II) and the compound (III) is conventionally conducted in a solvent (e.g. a halogenated hydrocarbon an ether, an ester, a hydrocarbon, an amide, etc.). such as chloroform, dichloromethane, ethyl ether, tetrahydrofuran, dioxane, dimethoxyethane, ethyl acetate, benzene, toluene, pyridine, N,N-dimethylformamide, etc., This reaction may be accelerated in the presence of a base. The reaction temperatures ranges usually from about −10° C. to 120° C., preferably from about 0° C. to 100° C. The reaction time usually ranges from 1 to 48 hours, preferably from 1 to 24 hours. The amount of the compound (III) to be employed ranges from 1 to 5 molar equivalents, preferably from 1 to 3 molar equivalents per one mole of the compound (II). As the base, use is made of, for example, an alkylamine such as triethylamine, etc., a cyclic amine such as N-methylmorpholine, pyridine, etc., an aromatic amine such as N,N-dimethyl aniline, etc., an alkali metal carbonate such as sodium carbonate, potassium carbonate etc., an alkali metal hydrogencarbonate such as sodium hydrogencarbonate, potassium hydrogencarbonate, etc. The amount of the base to be employed ranges from 1 to 5 molar equivalents, preferably 1 to 3 molar equivalents per one mole of the compound (II). And, in the case of using a solvent which is immiscible with water, the reaction may be allowed to proceed by adding water to the reaction system, i.e. as a two-layer reaction system.

Method (2): This method is also an acylation reaction similar to that in Method (1). In this method, an alcohol derivative, which is the compound (V) or a salt thereof whose $Y^1$ is —O—, and an amine derivative, which is the compound (V) whose $Y^1$ is —$NR^2$—, are allowed to react with the compound (IV) or a salt thereof to produce the compound (I-1). The reaction is conducted in substantially the same procedure as described in Method (1), using the compound (V) in place of the compound (II) in Method (1). In this method also, in the case where X of the compound (IV) is —NH—, it is preferable to use the compound (IV) as an isocyanate derivative formed by removing H-$L^4$ from the compound (iv).

Among the compounds (I) of this invention, a compound in which Q is sulfur atom, can be produced by allowing a compound whose Q is oxygen to react with a suitable compound containing sulfur. As the reagent containing sulfur employed in this reaction, use is made of, for example, phosphorus pentasulfate, Lowesson reagent, etc. This reaction is conducted usually under anhydrous conditions, in a solvent such as dichloromethane, chloroform dioxane, tetrahydrofuran, benzene, toluene, etc. The amount of the reagent is equimole or more, preferably 2 to 5 moles, and the reaction temperatures ranges from 20° C. to 120° C., while the reaction time varies with a starting compound or a kind of a compound of reagent, and the reaction temperatures, it usually ranges from 1 to 8 hours.

In the case where the compound (I), (I-1) or a salt thereof produced by the above-mentioned Methods (1) or (2) contain a lower ($C_{1-4}$) alkoxy group in the benzene ring in the groups represented by ring A, ring B or Ar, the alkoxy group can be converted into hydroxyl group by, upon necessity, converting into hydroxyl group by allowing the alkoxy group to react with, for example, boron tribromide. This reaction is conducted usually in a solvent (e.g. a halogenated hydrocarbon or a hydrocarbon such as dichloromethane, chloroform, carbon tetrachloride, benzene, toluene, etc.) at temperatures ranging from about –20° C. to 80° C., preferably from about 0° C. to 30° C., and, the amount of the boron tribromide ranges from about 1 to 10 molar equivalents, preferably from about 1 to 5 molar equivalents per one lower alkoxy group. The reaction time ranges usually from 15 minutes to 24 hours, preferably from 30 minutes to 12 hours. And, in the case where the compound (I), (I-1) or a salt thereof produced by the above-mentioned Methods (1) or (2) contain hydroxyl group in the benzene ring in the groups represented by ring A, ring B or Ar, the hydroxyl group is, upon necessity, subjected to alkylation or acylation reaction to convert into alkoxy or acyloxy group, respectively.

The alkylation reaction of the hydroxyl group on the benzene ring is conducted by allowing an alkylating agent such as halide of an optionally substituted alkane (e.g. chloride, bromide, iodide, etc.), a sulfuric acid ester or a sulfonic acid ester (e.g. methansulfonate, p-toluenesulfonate, benznensulfonate, etc.) to react with the hydroxyl group in a solvent (e.g. a alcohol such as methanol, ethanol, propanol, etc., an ether such as dimethoxyethane, dioxane, tetrahydrofuran, etc., a ketone such as acetone, etc., an amide such as N,N-dimethylformamide, etc.), in the presence of a base (e.g. an organic base such as trimethylamine, triethylamine, N-methylmorpholine, pyridine, picoline, N,N-dimethylaniline, etc., an inorganic base such as potassium carbonate, sodium carbonate, potassium hydroxide, sodium hydroxide, etc.). The reaction temperatures ranges usually from –10° C. to 100° C., preferably from about 0° C. to 80° C. The amount of these alkylating agents to be employed ranges from about 1 to 5 molar equivalents per one mole of the starting phenolic derivative, preferably from 1 to 3 molar equivalents. The reaction time ranges usually from 15 minutes to 24 hours, preferably from 30 minutes to 12 hours.

Acylation is carried out by using the appropriate carboxylic acid or a reactive derivative thereof. Although varying depending on type of acylating agent and type of starting material phenolic derivative, this reaction is normally carried out in a solvent (e.g. hydrocarbons, ethers, esters, halogenated hydrocarbons, amides, aromatic amines such as benzene, toluene, ethyl ether, ethyl acetate, chloroform, dichloromethane, dioxane, tetrahydrofuran, N,N-dimethylformamide and pyridine, etc.); appropriate bases (e.g. hydrogen carbonates such as sodium hydrogen carbonate and potassium hydrogen carbonate, carbonates such as sodium carbonate and potassium carbonate, acetates such as sodium acetate, tertiary amines such as triethylamine, aromatic amines such as pyridine) may be added to accelerate the reaction. Such reactive derivatives of carboxylic acid include acid anhydrides, mixed acid anhydrides and acid halides (e.g. chloride, bromide). The amount of these acylating agents used is 1 to 5 mol equivalents, preferably 1 to 3 mol equivalents per mol of starting material phenolic derivative. Reaction temperature is normally about 0° to 150° C., preferably about 10° to 100° C. Reaction time is normally 15 minutes to 12 hours, preferably 30 minutes to 6 hours.

When compound (I) is obtained in a free form by one of the above methods, it may be prepared for a salt as mentioned hereinabove in accordance with a conventional method or the like. When compound (I) is obtained in the form of a salt, it can be converted to the free form or another salt, in accordance with a conventional method or the like.

The thus-obtained desired compound (I) or salt thereof can be purified and separated by a known means of separation and purification (e.g. concentration, solvent extraction, column chromatography or recrystallization, etc.).

Starting material (II) and (IV) or a salt thereof, used to produce the inventive compound (I) or a salt thereof include compounds shown in the following formula: (S-1)~(S-7) and so on, these compounds can produce by the starting materials shown in the following formula (S-a)~(S-d).

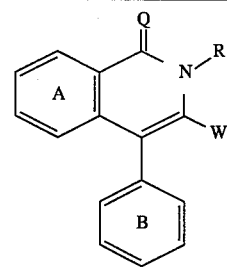

(S-1) W = —$CH_2OH$
(S-2) W = —$CH_2NHRR^1$
(S-3) W = —$CH_2CO_2H$
(S-4) W = —$CH_2CH_2OH$
(S-5) W = —$CH_2CH_2NHR^1$
(S-6) W = —$CH_2NCO$
(S-7) W = —$CH_2CH_2NCO$
(S-a) W = —$CO_2H$
(S-b) W = —$CH_2$—L
(S-c) W = —$CH_2CH_2$—L
(S-d) W = —$CH_2CH_2CO_2H$ wherein L stands for a leaving group which is the same as $L^2$ and $L^4$, and other symbols are of the same meaning as defined above.

When starting materials (II)–(V) of this invention have a basic group such as an amino group or a substituted amino group, these starting materials may form a physiologically acceptable acid addition salt. As such a salt, use is made of, for example, a salt with an inorganic acid (e.g. hydrochloric acid, phosphoric acid, hydrobromic acid, sulfuric acid) or a salt with an organic acid (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid). Further, when these starting materials have an acid group such as —COOH, these starting materials may form a salt with an inorganic base (e.g. an alkali metal or alkaline earth metal such as sodium potassium, magnesium, etc., ammonia) or an organic base (e.g. tri-$C_{1-3}$ alkylamine such as triethylamine, etc.).

While these starting materials or salts thereof, a part of which are known compounds, can be produced by the methods described in the following literature references or those analogous thereto, concrete examples of the production are shown below.

As a starting materials of producing the Compounds (S-1)–(S-7), use is made of, for example, the compound (S-a).

Referring to the compound (S-a) or salts thereof or esters thereof, methods of synthesizing the respective object compounds or intermediates for the synthesis are described in the literature, for example, "N. A. Santagati et al., Bolletino Chimico Farmaceutico, 125, pp. 437–440 (1986)" or "H. Natsugari, et al., EP-A-481383 (Date of publication: 22 April, 1992)", and these compounds can be produced by those methods or methods analogous thereto. And, these compounds can also be produced by way of an amide-derivative of (S-a). The amide derivative of (S-a) (W=—$CONH_2$) can be produced by the method described in literature "K. Umverferth et al., Archiv der Pharmazie), 324, pp. 809–814 (1991)" or a method analogous thereto. By allowing this amide compound to react under diazotization reaction conditions (for example, with sodium nitrite in, e.g. an acid solvent such as acetic acid or hydrochloric acid at temperatures ranging from about 0° C. to 50° C.) to produce the compound (S-a).

The compound (S-1) or a salt thereof can be produced by subjecting the carboxyl group of the compound (S-a) to reduction.

The reduction can be conducted by converting the carboxyl group into the corresponding reactive derivative (e.g. acid halide, a mixed acid anhydride, active ester, ester, etc.), using a reducing agent (e.g. sodium borohydride, lithium aluminum hydride, etc.) in a solvent (e.g. ethers such as teterahydrofuran, dimethoxyethane, etc.) at temperatures ranging from about 0° C. to 100° C.

The compound (S-2) can be produced from the compound (S-1) via the compound (S-b). The compound (S-b) can be produced by converting the hydroxyl group of the compound (S-1) into the leaving group L. As the leaving group L, use is preferably made of a halogen (e.g. chlorine, bromine, iodine, etc.), a $C_{1-4}$ alkanesulfonyloxy group (e.g. methanesulfonyloxy group, ethanesulfonyloxy group, etc.), $C_{6-10}$ arylsulfonyloxy group (benzene sulfonyloxy group, p-toluenesulfonyloxy group, etc.). Said conversion reaction is usually carried out in a solvent (e.g. benzene, toluene, dichloromethane, 1,2-dichloroethane, chloroform, tetrahydrofuran, ethyl acetate, etc.), processing with, for example thionyl chloride, thionyl bromide, methansulfonyl chloride, benzene sulfonyl chloride, etc. at temperatures ranging from about 0° C. to 100° C.

The compound (S-2) or a salt thereof is produced by allowing the leaving group of the compound (S-b) to react with an amine compound represented by the formula $R^1$-$NH_2$, wherein symbols are of the same meaning as defined above. In this reaction, while an amine compound may be used in the free state as it is, it can be subjected to reaction as an alkali metal salt, for example, lithium, sodium, potassium, etc. Relative to one mole of the compound (S-b), 1 to 10 moles, preferably 1 to 5 moles, of the amine compound or a salt thereof is subjected to reaction. Usually, the reaction is conducted in a solvent. As the solvent, use is preferably made of, for example, halogenated hydrocarbons such as dichloromethane, chloroform, etc., nitriles such as acetonitrile, etc., dimethylformamide, dimethyl sulfoxide, hexamethylphosphoramide, or the like. Addition of a base serves to accelerate to allow the reaction to proceed advantageously. Preferable examples of such bases include sodium hydrogencarbonate, potassium hydrogencarbonate, sodium carbonate, potassium carbonate, sodium hydride, potassium hydride, sodium amide, sodium methoxide, triethylamine, diisopropylethylamine, pyridine, etc. Instead of using bases as mentioned above, amine compounds themselves may be used as the bases. The amount of bases varies with kinds of the compound (S-b), amine compound and solvent to be then employed and other reaction conditions, it usually ranges from 1 to 10 moles, preferably 1 to 5 moles relative to 1 mole of the compound (S-b). The reaction temperature ranges from about –50° C. to 200° C., preferably from –20° C. to 150° C. While the reaction time varies with the kinds of the compound (S-b), kinds of amine compounds or salts thereof, reaction temperature, it ranges from 1 to 72 hours, preferably 1 to 24 hours. Among the compounds (S-2), the compound whose $R^1$ is hydrogen can be produced also by the method described in the aforementioned "Archiv der Pharmazie, 324, pp. 809–814, Unverferth, et al. (1991)".

The compound (S-3) or a salt thereof can be produced by, for example, the method (a), (b) or a one analogous thereto. The method (a) is to increase the number of the carbon atoms of the carboxyl group of (S-a) by one using diazomethane by means of the reaction generally known as "Arndt-Eistert" reaction "F. Arndt et al., Chemische Berichte, 68, p. 200 (1935)". In this method, while,in some instances, respective (S-3) compounds are isolated as esters of carboxylic acids (e.g. methyl ester, ethyl ester, etc.), these esters are subjected to hydrolysis to convert into carboxylic acid. This hydrolysis is conducted usually in a solvent (e.g. alcohols such as methanol, ethanol, propanol, etc., organic acids such as acetic acid, etc.), in the presence of an aqueous solution of a mineral acid (e.g. hydrochloric acid, hydrobromic acid, sulfuric acid, etc.) or a metal hydroxide (e.g. sodium hydroxide, potassium hydroxide, etc.) at temperatures ranging from about 15° C. to 130° C. The process (b) is to give the compound (S-3) having one carbon increased by converting the leaving group L of the compound (S-b) into cyano group followed by hydrolysis. The conversion into cyano group is conducted by processing with a compound containing cyano group such as sodium cyanide, potassium cyanide, copper cyanide, etc. at temperatures ranging from 0° C. to 100° C. This nitrile compound is subjected to hydrolysis to give carboxylic acid of (S-3). This hydrolysis is conducted usually in a solvent (e.g. alcohol such as methanol, ethanol, propanol, acetic acid, etc.) in the presence of an aqueous solution of a mineral acid (e.g. hydrochloric acid, hydrobromic acid, sulfuric acid, etc.) or a metal hydroxide (e.g. sodium hydroxide, potassium hydroxide, etc.) at temperatures ranging from about 15° C. to 130° C.

The compound (S-4) can be produced by using (S-3) in substantially the same manner as in the case of converting from (S-a) to (S-1), and the compound (S-5) can be produced by using (S-4), by way of (S-c), in substantially the same manner as in the case of converting from (S-1) to (S-2) via (S-b).

The compounds (S-6) and (S-7) are compounds, among the compounds (IV), corresponding to those wherein X stands for —NH— (m=1, 2). These isocyanate derivatives are produced usually via acid azide compound from carboxylic acid (S-3) and (S-d). This process are disclosed in various literature references, which can be applied to (S-3) and (S-d).

For example, by allowing azidating agent (e.g. diphenylphosphoryl azide, hereinafter abbreviated as DPPA, etc.) to react with the compound (S-3) or (S-d), these acid azides can be produced. This reaction can be conducted usually in a solvent inert to the reaction (e.g. an ether such as ethyl ether, isopropyl ether, dimethoxyethane, tetrahydrofuran, dioxane, etc., an aromatic hydrocarbon such as benzene, toluene, xylene, etc., a ketone such as acetone, 2-butanone, etc., an aromatic amine such as pyridine, amides such as N,N-dimethylformamide, etc.). And, the reaction may be allowed to proceed in the presence of a base (e.g. trimethylamine, triethylamine, N-methylmorpholine, etc.). The reaction time ranges usually from about 5 minutes to 12 hours, preferably from about $-5°$ C. to 120° C. The amount of the azidating agent (e.g. DPPA, etc.) to be employed ranges from 1 to 3 molar equivalents, preferably 1 to 2 molar equivalents, relative to the compound (S-3) or (S-d).

While the acid azide thus produced can be isolated and purified by per se known means, usually it is converted to isocyanate derivatives (S-6) and (S-7) by heating the reaction mixture without isolating the acid azide. For this conversion reaction, use of the same solvents used for the azidation is preferable, and the reaction is conducted by heating usually at temperatures ranging from about 20° C. to 200° C., preferably from about 30° C. to 150° C. The reaction temperature ranges usually from about 5 minutes to 10 hours, preferably from about 5 minutes to 6 hours.

The compound (S-d) to be employed for the production of the compound (S-7) can be produced by the method (a), (b) in the production of the above-mentioned compound (S-3), from the compound (S-3) or (S-c).

While, by the processes described in the forgoing, compounds (S-1)-(S-7) having various substituents as R can be produced, in the case where functional groups are further contained in the substituents of R of these compounds, they can be converted into any other desirable functional groups. For example, when R is a group containing carboxyl group or an ester thereof, it is allowed to react with, for example, amine to convert into amide group or subjected to reduction to convert into hydroxymethyl group to give a material for the synthesis of the compound (I).

By allowing the above-mentioned compound (S-1)–(S-7) to react with a suitable suffur containing regent to convert the oxo group at 1-position into thioxo group, and thus-modified compounds can be used as starting compounds for producing the compound (I). This process can be carried out in substantially the same manner as in the process for converting the above-mentioned compound, which is the compound (I) wherein Q stands for oxygen atom, into the compound which is the compound (I) wherein Q stands for sulfur atom.

As another starting compound (III) or (V) to be employed for producing the compound (I) or salts thereof of this invention, use is made of compounds which can be produced by per se known methods or methods analogous thereto.

The above-mentioned starting compounds may be in the form of salts. As these salts, use is made of, for example, salts with an inorganic acid (e.g. hydrochloric acid, phosphoric acid, hydrobromic acid, sulfuric acid, or salts with an organic acid (e.g. acetic acid, formic acid, propionic acid, fumaric acid, maleic acid, succinic acid, tartaric acid, citric acid, malic acid, oxalic acid, benzoic acid, mathanesulfonic acid, benzenesulfonic acid). Further, in the case where these compounds have an acidic group such as —COOH, they may form salts with an inorganic base (e.g. an alkali metal or alkaline earth metal such as sodium, potassium, calcium, magnesium, or ammonia, etc.) or salts with an organic base (e.g. tri- $C_{-3}$ alkylamine such as triethylamine.

Compound (II), (IV) and other starting compounds obtained by the above-mentioned processes may be purified or recovered by a per se known procedure, for example, concentration, pH adjustment, phasic transfer, solvent extraction, column chromatography, crystallization, recrystallization, etc., or the reaction mixture can be directly used in the subsequent reactions.

In connection with each of the above reactions for producing the above-mentioned object compound and the starting compounds, the starting compound to be employed, where it has an amino group, carboxyl group or hydroxyl group as the substituent, it can be used as previously protected with an appropriate protective group which is commonly used in peptide and other chemistry and, if necessary, the deprotected compound can be obtained by removing such protective group after the reaction.

As the protective group for such amino group, use is made of, for example, an optionally substituted $C_{1-6}$ alkyl carbonyl group (e.g. formyl, methylcarbonyl, ethylcarbonyl, etc.), a phenylcarbonyl group, a $C_{1-6}$ alkyloxycarbonyl group (e.g. methoxycarbonyl, ethoxycarbonyl, etc.), a phenyloxycarbonyl group (e.g. benzoxycarbonyl, etc.), a $C_{7-10}$ aralkylcarbonyl group (e.g. benzyloxycarbonyl, etc.), a trityl group, a phthaloyl group and so on. As these substituents, use is made of halogen atom (e.g. fluoro, chloro, bromo, iodo, etc.), a $C_{1-6}$ alkyl—carbonyl group (e.g. metylcarbonyl, ethylcarbonyl, butylcarbonyl, etc.), a nitro group or the like., and the number of substituent groups ranges from about 1 to about 3.

Examples of the protective group for said hydroxyl group include an optionally substituted $C_{1-6}$ alkyl group (e.g. methyl, ethyl, n-propyl, i-propyl, n-butyl, tert-butyl, etc.), a phenyl group, a $C_{7-6}$ aralkyl group (e.g. benzyl, etc.), a $C_{1-4}$ alkylcarbonyl group (e.g. formyl, methylcarbonyl, ethylcarbonyl, etc.), a phenyloxycarbonyl group (e.g. benzoxycarbonyl etc.), a $C_{7-10}$ aralkylcarbonyl group (e.g. benzyloxycarbonyl, etc.), pyranyl, furanyl, silyl, etc.). As these substituents, use is made of a halogen atom (e.g. fluoro, chloro, bromo, iodo, etc.), a $C_{1-6}$ alkyl group, a phenyl group, a $C_{7-10}$ aralkyl group, a nitro group and so on. The number of substituent groups ranges from about 1 to about 4.

These protective groups can be removed by the per se known procedures or any procedures analogous thereto. For example, treatment with an acid, or a base, reduction, irradiation with ultraviolet light, and treatment with a hydrazine, a phenylhydrazine, a sodium N-methyldithiocarbamate, a tetrabutylammonium fluoride, a palladium acetate, etc.

The compound (I) or a salt thereof produced by the above methods can be isolated and purified by conventional procedures including recrystallization, distillation and chromatography. When the compound (I) thus obtained is the free compound, it can be converted to a salt by per se known procedures (e.g. neutralization, etc.) or any procedure analogous thereto. Conversely, when the product is a salt, it can be converted to the free compound or any other salt by a per se known procedure or any procedure analogous thereto.

The compound (I) of this invention or salts thereof have a potent protective effect of cerebralischemia, activity of anti-cerebral edema, activity of inhibiting release of calcium from endoplasmic reticulum of neural cells, and the toxicity is relatively low [acute toxicity of the compounds of the following Examples (mouse, p.o): $LD_{50}$>1,000 mg/kg], thus the safety as medicines being relatively high.

Accordingly, the compound (I) of this invention or salts thereof are useful as safe therapeutic and prophylactic agents of cerebralvascular disorders due to acute or chronic cerebrovascular damage, for example, cerebral infarction, subarachnoid hemorrhage, cerebral edema, etc. in mammals (e.g. mouse, rat, hamster, gerbil, rabbit, cat, dog, bovine, sheep, monkey, man, etc.). Further, the present compound (I) or salts thereof are also useful as therapeutic and prophylactic agents of various diseases due to neuronal damage, for example, mental disorders (e.g. dementia, hallucination, depression, etc.), dyscinesia (e.g. paralysis, parkinsonism, etc.), disturbance of consciousness (e.g. coma, clouding of consciousness, etc.), dysethesia (e.g. pain, numbness, etc.).

The compound (I) or salts thereof of this invention have excellent tachykinin receptor antagonizing activity, especially potent antagonistic activity against substance P (SP). Substance p (SP) is a neuropeptide discovered in an equine intestinal canal extract in 1931 and its structure, consisting of 11 amino acids, was established in 1971. SP is broadly distributed in the central and peripheral nervous system and, in addition to being a primary sensory neurotransmitter, has various physiological activities such as vasodilating activity, smooth muscle contracting activity, neuronal excitatory activity, sialogogue activity and diuretic activity. It is known especially that SP released by a pain impulse at the terminal of the cornu posterius of the spinal cord transmits pain information to secondary neurons and that SP released from peripheral nerve terminal induces an inflammatory response in the nociceptive field. Moreover, SP is suspected to be involved in Alzheimer type dementia. Therefore, the compound (I) or salts thereof having potent SP receptor antagonizing activity are of value as a safe prophylactic and therapeutic drug for pain, inflammation, allergy and dementia in mammalian animals (e.g. mouse, rat, hamster, rabbit, cat, dog, bovine, sheep, monkey, man, etc.).

For medicinal use, the compound (I) or salts thereof of this invention can be formulated with suitable pharmaceutically acceptable carriers or excipients (e.g. starch, lactose, sucrose, calcium carbonate, calcium phosphate, etc.), binders (e.g. starch, gum, arabic, carboxymethylcellulose, hydroxypropylcellulose, crystalline cellulose, alginic acid, gelatin, polyvinylpyrrolidone, etc.), lubricants (e.g. stearic acid, magnesium stearate, calcium stearate, talc. etc.), disintegrators (e.g. carboxymethylcellulose calcium, talc., etc.), and diluents (e.g. physiological saline solution) and administered orally or non-orally in such dosage forms as powders, fine granules, granules, tablets, capsules, injections and so on. While the dosage is dependent on the species of compound (I) or salts thereof, route of administration, symptoms of diseases, patients age and so on, for oral administration to an adult patient suffering from cerebral edema, for instance, a daily dose of about 0.01 to 200 mg, preferably about 0.1 to 20 mg, per kg body weight. This range of dose is preferably divided into 1 to 3 daily.

The following are experimental data showing the pharmacological effects of the compound (I) or salts thereof of the present invention.

Test Example 1 Protective effect of cerebralischemia

Male mongolian gerbils (Seiwa/8–10 wks) (n=8–10) were used. Bilateral common carotid arteries were occluded after the incision of the center of the neck under ether anesthesia. Global cerebral ischemia was induced by the occlusion of bilateral common carotid arteries (15 minutes), and after that these arteries were reperfused. Test sample was administered intraperiatonelly 30 minutes before occlusion and 90 minutes after reperfusion. In the control group, vehicle (distilled water, saline or 5% gum arabic) was administered in the same fashion. Survival ratio was estimated at 8 hr after reperfusion (Table 2).

TABLE 2

| Example (compound) no. | Dose (mg/kg, ip) | Survival ratio (%) |
| --- | --- | --- |
| 1 | 5 | 88*** |
| 14 (HCl) | 5 | 63* |
| 15 (HCl) | 5 | 88*** |
| " | 0.3 | 80** |
| 16 | 5 | 88*** |
| 17 (Na) | 5 | 67* |
| 22 (Ma) | 5 | 63* |
| 24 | 5 | 75** |
| 27 | 5 | 88*** |
| 28 (Na) | 5 | 75** |
| 29 | 5 | 75** |
| 32 | 5 | 63* |
| 39 (HCl) | 5 | 63* |
| 40 (HCl) | 5 | 75** |
| 41 (HCl) | 5 | 88*** |
| " | 0.3 | 75* |
| 43 (HCl) | 5 | 63* |
| 44 (HCl) | 5 | 63* |
| 45 (HCl) | 5 | 82*** |
| 47 (HCl) | 5 | 75** |
| 48 (HCl) | 5 | 88*** |
| 49 (HCl) | 5 | 88*** |
| 50 (HCl) | 5 | 75** |
| 51 (HCl) | 5 | 100*** |
| 53 (HCl) | 5 | 75** |
| control | — | 0 |

*$p < 0.05$, $p < 0.01$, *$p < 0.001$ vs vehicle

From Table 2, it is seen that the chemical compound (I) or salts thereof in this invention ameliorate the survival ratio after transient cerebral ischemia in mongolian gerbils and it is suggested that these compounds are useful as the drugs for the therapy or the protection of cerebral ischemic disease.

Test Example 2 Anti-brain edema effect (middle cerebral arterial occlusion and reperfusion model)

Male wistar rats (Jcl:9wks) were anesthetized with inhalation of halothane (2-bromo-2-chloro-1,1,1-trifluoroethane). After the incision of neck, bilateral common carotid arteries were removed an embolized needle (diameter 0.3 mm, length 26 mm nylon thread) was inserted into the left internal carotid artery through external carotid artery and, simultaneously, the bilateral common carotid arteries were occluded by the Sugita's aneurysm clips. The embolized needle and the clips were removed out 30 minutes after occlusion. Test sample was administered immediately and 5 hr after reperfusion on the operated day, twice a day on the 1st and 2nd day, and 1 hr before removing the brain on the 3rd day (total 7 times), intraperiatonelly. In the control group, vehicle (distilled water, saline or 5% gum arabic) was administered in the same fasion. Brain edema on the 3rd day after reperfusion was estimated from the content of water, potassium and sodium in cerebral cortex and striatum. Water content was calculated from the ratio of dried brain weight and wet brain weight [(1-dried weight/wet weight)×100%]. The contents of pottasium and sodium were measured using the solution extracted from dried brain tissue with 14% nitric acid by the method of the framephotometer (Table 3).

TABLE 3

| | $H_2O$ (%) | Na (mEq/kg) | K (mEq/kg) |
|---|---|---|---|
| Example 1 | | | |
| sham | 78.86 ± 0.04 | 235 ± 1 | 526 ± 1 |
| control | 81.27 ± 0.38 | 405 ± 29 | 430 ± 13 |
| treatment, 10 mg/kg(ip) × 7 | 80.12 ± 0.32* | 322 ± 24* | 471 ± 13* |
| Example 15(HCl) | | | |
| sham | 78.95 ± 0.03 | 233 ± 14 | 520 ± 2 |
| control | 80.94 ± 0.18 | 371 ± 13 | 440 ± 7 |
| treatment, 10 mg/kg(ip) × 7 | 80.24 ± 0.23* | 325 ± 17* | 466 ± 9* |

*p < 0.05

From Table 3, it is seen that the compounds (I) or salts thereof in this invention decreased the contents of water and sodium and increased that of potassium. It is suggested that these compounds are useful as the therapeutic drug of brain edema.

Test Example 3

Effect on cytosolic free $Ca^{2+}$ concentration in neurons

Neurons were harvested from hippocampi of 18-day-old rat embryos and cultured based on the method of Hatanaka and Tsukui (Developmental Brain Research, 30, 47–56, 1986). Hippocampal neurons suspended in Dulbecco's modified Eagle's medium were seeded on cover glass slides (10×20 mm, Matunami No. 1, Osaka, Japan) coated with poly-L-lysin at a density of $2.5×10^5$ cells/slide and cultured for 7 days in humidified $CO_2$ incubator (95% air/5% $CO_2$) at 37° C. The neurons were washed 3 times with HEPES [N-(2-hydroxyethyl)piperazine-N'-2-ethanesulfonic acid]-buffered physiological salt solution (PSS) (140 mM NaCl, 5 mM KCl, 1 mM $MgSO_4$, 1 mM $Na_2HPO_4$, 1 mM $CaCl_2$, 25 mM glucose, 25 mM HEPES, pH7.4), and then loaded with fura-2 acetoxymethyl ester (4 µM) in HEPES-buffered PSS for 60 min at 37° C. The cover glass slide coated with neurons, which were loaded with fura-2, was inserted into a cuvette that contained 2.5 ml HEPES-buffered PSS supplemented with 0.05% bovine serum albumin. $Ca_{2+}$-fura-2 fluorescence was measured with Hitachi F-2000 spectrofluorimeter by 340 nm and 380 nm for excitation and 505 nm for emission. Cytosolic free $Ca^{2+}$ concentration ($[Ca^{2+}]i$) values were calculated according to the method of Grynkiewicz et. al, (Journal of Biological Chemistry, 260, 3440–3450, 1985). Neurons were treated with example-compounds 5 min before the addition of L-glutamic acid (L-Glu.).

L-Glu. leads to two phases-increase of $[Ca^{2+}]_i$ in neurons. The first increase of $[Ca^{2+}]_i$ is caused by the release from cellular $Ca^{2+}$ stores and the influx of extracellular $Ca^{2+}$. The second one is caused by the influx of extracellular $Ca^{2+}$. The effect of the drug on these two phases-increase of $[Ca^{2+}]_i$ was examined and the 50% inhibitory dose ($IC_{50}$) was calculated. $ICs_{50}$ obtained by addition of EGTA [ethylene glycol-O,O'-bis (2-aminoethyl)-N,N,N',N'-tetraacetic acid], which inhibits the extracellular $Ca^{2+}$ influx and the $Ca^{2+}$ peak in the first phase is only caused by the release from cellular $Ca^+$ stores under this condition, is also shown (Table 4).

TABLE 4

| Example (compd.) No. | $IC_{50}$ without EGTA 1st Phase | $IC_{50}$ without EGTA 2nd Phase | $IC_{50}$ with EGTA 1st Phase |
|---|---|---|---|
| 1 | $3.0 × 10^{-6}$M | $>10^{-5}$M | $6.9 × 10^{-8}$M |

From the Table 4, it is shown that the compound or salt thereof in this invention strongly inhibits the $Ca^{2+}$ release from cellular $Ca^{2+}$ stores in neurons and it is suggested that these compounds are useful as drugs for calcium antagonism.

Test Example 4

Radioligand receptor binding inhibitory assay using receptor from human lymphoblast cells (IM-9)

The method of "A. Margaret et al. Molecular Pharmacology 42, 458 (1992)" was modified and used. The receptor was prepared from human lymphoblast cells (IM-9). IM-9 cells were grown in 175 $cm^2$ tissue culture flasks (100 ml z 10) at a density approximately $2×10^5$/ml of RPMI 1640 with L-glutamine, 10% (V/V) heat inactivated fetal calf serum, penicillin (100 u/ml), and streptomycin (100 µg/ml) at 37° C. in 5%$CO_2$/95% air for 3 days. IM-9 cells were obtained by centrifugation at 500 Xg for 5 minutes at 5° C. The pellet obtained was washed once with phosphate buffer (Flow Laboratories, CAT No. 28-103-05), homogenized using Polytron homogenizer (Kinematika, Germany) in 30 ml of 50 mM Tris-HCl buffer containing 120 mM NaCl, 5 mM KCl, 2 µg/ml phenylmethyl sufonyl fluoride, and 1 mM ethylenediamine tetra-acetic acid and then centrifuged at 40,000 Xg for 20 minutes. The residue was washed twice with 30 ml of buffer described above, and preserved frozen (-80° C.).

The above specimen was suspended in a reaction buffer (50 mM Tris-HCl buffer (pH 7.4), 0.02% bovine serum albumin, 1 mM phenylmethylsufonyl fluoride, 2 µg/ml chymostatin, 40 µg/ml bacitracin, 3 mM manganese chloride) at a protein concentration of 1.5 mg/ml and a 100 µl portion of the suspension was used in the reaction. After addition of the sample and 125I-BHSP (0.46 KBq), the reaction was conducted in 0.2 ml of reaction buffer at 25° C. for 30 minutes. The amount of nonspecific binding was determined by adding substance P at a final concentration of 2×101-6 M. After the reaction, using a cell harvester (290PHD, Cambridge Technology, Inc., England), rapid filtration was carried out through a glass filter (GF/B, Whatman, U.S.A.) to stop the reaction. After washing three times with 250 µl of 50 mM Tris-HCl buffer (pH 7.4) containing 0.02% bovine serum albumin, the radioactivity remaining on the filter was measured with a gamma counter. Before use, the filter was immersed in 0.1% polyethyleneimine for 24 hours and air-dried.

The antagonistic activity of each test substance, in terms of the concentration necessary to cause 50% inhibition "$IC_{50}$" under the above conditions, was expressed in µM (Table 5).

TABLE 5

| Example No. | IC$_{50}$ (μM) |
|---|---|
| 36 | 0.047 |
| 37 | 0.001 |
| 38 | 0.072 |

From Table 5, it is seen that the compound (I) or salts thereof in this invention have excellent substance P receptor antagonizing activity.

EXAMPLES

The present invention is hereinafter described in more detail by means of the following reference examples and working examples. The following Reference Examples and Examples are further descriptive of the present invention. It should be understood that these are merely illustrative and by no means definitive of the invention and that many changes and modifications can be made within the scope of the invention.

"Room temperature" means usually temperatures ranging from 10° C. to 35° C.

In the description of NMR spectrum data, the following abbreviations are employed. s, singlet; d, doublet; t, triplet; q, quartet; m, multiplet; b, broad; Hz, Herz; like, approximate; DMF, dimethylformamide; THF, tetrahydrofuran; DMSO, dimethyl sulfoxide

Reference Example 1

1,2-Dihydro-3-hydroxymethyl-2,6,7-trimethyl-1-oxo-4-phenylisoquinoline

Step 1

A mixture of 2-benzoyl-4,5-dimethylbenzoic acid (11.4 g), acetone (300 ml), DMF (10 ml), potassium carbonate (6.83 g) and diethyl bromomalonate (12.84 g) was stirred for 60 hours at room temperature. The solvent was distilled off. To the residue was added ethyl acetate. This mixture was washed with water and dried (Na$_2$SO$_4$), then the solvent was distilled off. To the residue were added acetic acid (180 ml) and hydrochloric acid (180 ml), and the mixture was heated for 5 hours at 110° C. The reaction mixture was concentrated, to which was added water, followed by extraction with ethyl acetate. The extract was washed with water, and dried (Na$_2$SO$_4$), then the solvent was distilled off to leave colorless crystals. Recrystallization from ethyl acetate-isopropyl ether to give 6,7-dimethyl-4-phenylisocumarin-3-carboxylic acid, m.p.265°–268° C.

Step 2

To a solution of the compound (3.75 g) obtained in Step 1 in methanol (50 ml) was added a 40% methylamine-methanol solution (25 ml), and the mixture was stirred for 2 hours at room temperature. The solvent was distilled off. To the residue was added 4N-HCl-ethyl acetate (50 ml), and the mixture was stirred for 2 hours at room temperature. The solvent was distilled off. To the residue was added water, then the resulting crystalline precipitate was collected by filtration, which was washed with water, acetone and ethyl ether to give 2,6,7-trimethyl-4-phenyl-1 (2 H)-isoquinolinone-3-carboxylic acid as colorless crystals (3.51 g) m.p. >300° C. (recrystallization from ethanol).

NMR (200 MHz,CDCl$_3$+DMSO-d$_6$) ppm: 2.25(3H,s), 2.39(3H,s), 3.67(3H,s), 6.91(1H,s), 7.39–7.42(5H,m), 8.24(1H,s)

Elemental Analysis for C$_{19}$H$_{17}$NO$_3$:
Calcd.: C, 74.25; H, 5.58; N, 4.56
Found: C, 74.40; H, 5.50; N, 4.41

Step 3

To a solution of the compound (9.27 g) obtained in Step 2 in THF (100 ml) were added oxalyl chloride (3.7 ml) and DMF (10 drops) at room temperature. The mixture was stirred for 30 minutes. The solvent was distilled off, and the residue was dissolved in THF (50 ml). This solution was gradually added at 0° C. to a suspension of sodium borohydride (5.0 g) in dimethoxyethane (100 ml). The mixture was stirred for 30 minutes at 0° C. The reaction mixture was added at 0° C. to 2N HCl, followed by extraction with ethyl acetate. The extract was washed with an aqueous solution of sodium hydrogencarbonate and water, which is then dried (MgSO$_4$). The solvent was distilled off to give the title compound as colorless crystals (7.18 g), m.p.209°–210° C. (recrystallization from ethyl acetate-isopropyl ether).

NMR (200 MHz,CDCl$_3$) ppm: 2.09(1H,bt,J=5.8Hz), 2.20(3H,s), 2.34(3H,s), 3.81(3H,s), 4.43(2H,d,J=5.8Hz), 6.73(1H,s), 7.25–7.35(2H,m), 7.45–7.55(3H,m), 8.19(1H,s)

By substantially the same procedure as in Step 3 of Reference Example 1, 1 (2H)-isoquinolinone-3-carboxylic acid having corresponding substituents was subjected to reduction to give the compounds of Reference Examples 2 and 3 as colorless crystals.

Reference Example 2

1,2-Dihydro-3-hydroxymethyl-2-methyl-1-oxo-4-phenylisoquinoline m.p.158°–159° C. (recrystallized from ethyl acetateisopropyl ether)

NMR (200 MHz,CDCl$_3$) ppm: 1.88(1H,bt), 3.83(3H,s), 4.48(2H,d,J=5.6Hz), 7.0–7.5(8H,m), 8.43–8.50(1H,m)

Reference Example 3

6-Chloro-1,2-dihydro-3-hydroxymethyl-2-methyl-1-oxo-4-phenylisoquinoline m.p.193°–195° C. (recrystallized from ethyl acetate ethyl ether)

NMR (200 MHz,CDCl$_3$) ppm: 2.04(1H,bt), 3.81(3H,s), 4.45(2H,d,J=5.4Hz), 6.98(1H,d,J=2Hz), 7.28(6H,m), 8.36(1H,d,J=8.6Hz)

Reference Example 4

3-Aminomethyl-1,2-dihydro-2,6,7-trimethyl-1-oxo-4-phenylisoquinoline

Step 1

To a solution of the compound (3.0 g) obtained in Reference Example 1 in dichloromethane (100 ml) were added, while stirring at 0° C., triethylamine (3.8 ml) and methanesulfonyl chloride (1.3 ml). The mixture was stirred for 30 minutes, to which was added dichloromethane. The mixture was washed with a 5% aqueous solution of phosphoric acid and water, which was then dried (MgSO$_4$), followed by distilling off the solvent to leave 1,2-dihydro-3 -methanesulfonyloxymethyl-2,6,7-trimethyl-1-oxo-4 -phenylisoquinoline as colorless crystals (2.98 g).

m.p.150°–151° C. (recrystallized from ethyl acetate-isopropyl ether)
NMR (200 MHz,CDCl$_3$) ppm: 2.25(3H,s), 2.40(3H,s), 2.86(3H,s), 3.77(3H,s), 5.01(2H,s), 6.82(1H,s), 7.25–7.35(2H,m), 7.45–7.60(3H,m), 8.27(1H,s)
Elemental Analysis for C$_{20}$H$_{21}$NO$_4$S:
  Calcd.: C, 64.67; H, 5.70; N, 3.77
  Found: C, 64.59; H, 5.69; N, 3.67

Step 2

A mixture of the compound (0.68 g) obtained in Step 1, THF (20 ml) and 15% ammonia/methanol (20 ml) was heated for 20 hours at 140° C. in a sealed tube. The solvent was distilled off. To the residue was added ethyl acetate, and the mixture was washed with an aqueous solution of potassium carbonate and water, successively, then dried (MgSO$_4$). The solvent was distilled off to leave the title compound as colorless crystals (0.37 g),
m.p.163°–165° C. (recrystallization from ethyl acetate).
NMR (200 MHz,CDCl$_3$) ppm: 2.22(3H,s), 2.37(3H,s), 3.65(2H,s), 3.84(3H,s), 6.70(1H,s), 7.24–7.50(5H,m), 8.24(1H,s)
Elemental Analysis for C$_{19}$H$_{20}$N$_2$O:
  Calcd.: C, 78.05; H, 6.89; N, 9.58
  Found: C, 77.86; H, 7.00; N, 9.41

By substantially the same procedures as in Step 1 and 2 of Reference Example 4, 1,2-dihydro-3-hydroxymethyl-1-oxoisoquinolines having corresponding substituents were allowed to react with methanesulfonyl chloride (Step 1), which was then allowed to react with an amine having corresponding substituents (Step 2) to give compounds of Reference Examples 5 to 7.

Reference Example 5

Step 1

1,2-dihydro-3-methanesulfonyloxymethyl-2-methyl-1-oxo-4-phenylisoquinoline
m.p.149°–150° C. (recrystallized from ethyl acetate isopropyl ether)
NMR (200 MHz,CDCl$_3$) ppm:2.88(3H,s), 3.80(3H,s), 5.05(2H,s), 7.05–7.13(1H,m), 7.29–7.58(7H,m), 8.51–8.55(1H,m)

Step 2

3-Aminomethyl-1,2-dihydro-2-methyl-1-oxo-4-phenylisoquinoline
m.p.186°–188° C. (recrystallized from ethyl acetate methanol)
NMR (200 MHz,CDCl$_3$) ppm: 3.68(2H,s), 3.86(3H,s), 6.95–7.0(1H,m), 7.26–7.52(7H,m), 8.45–8.52(1H,m)

Reference Example 6

Step 1

6-Chloro-1,2-dihydro-3-methanesulfonyloxymethyl-2-methyl-1-oxo-4-phenylisoquinoline
mp.163°–165° C. (recrystallized from ethyl acetate isopropyl ether)
NMR (200 MHz,CDCl$_3$) ppm: 2.88(3H,s), 3.78(3H,s), 5.01(2H,s), 7.05(1H,d,J=2.2 Hz), 7.27–7.56(6H,m), 8.46(1H,d,J=8.6 Hz)

Step 2

3-Aminomethyl-6-chloro-1,2-dihydro-2-methyl-1-oxo-4-phenylisoquinoline
m.p.175°–177° C. (recrystallized from ethyl acetate methanol)
NMR (200 MHz,CDCl$_3$) ppm: 3.66(2H,s), 3.85(3H,s), 6.92(1H,d,J=1.8 Hz), 7.23–7.52(6H,m), 8.41(1H,d,J=8.4 Hz)

Reference Example 6A

6-Chloro-1,2,dihydro-2-methyl-3-(N-methylamino)methyl-1-oxo-4-phenylisoquinoline
NMR (200 MHz,CDCl$_3$ ppm:2.30(3H,s), 3.46(2H,s), 3.84(3H,s), 6.94(1H,d,J=1.8 Hz), 7.22–7.51(6H,m), 8.42(1H,d,J=8.8 Hz) [used for the subsequent reaction without purification].

Reference Example 7

1,2-Dihydro-2,6,7-trimethyl-1-oxo-4-phenyl-3-isoquinoline acetic acid

Step 1

The compound (6.4 g) obtained in Step 1 of Reference Example 4 was dissolved in DMSO (80 ml). To the solution was added sodium cyanide (5.0 g), and the mixture was stirred for 30 minutes at room temperature. To this reaction mixture was added ethyl acetate, which was washed with water and dried (MgSO$_4$), followed by distilling off the solvent to leave 3-cyanomethyl-1,2-dihydro-2,6,7-trimethyl-1-oxo-4-phenylisoquinoline as colorless crystals (4.7 g).
m.p.186°–188° C. (recrystallized from ethyl acetate isopropyl ether)

Step 2

A mixture of the compound (4.7 g) obtained in Step 1, acetic acid (150 ml) and hydrochloric acid (150 ml) was heated for 7 hours at 110° C. The solvent was distilled off. To the residue was added ethyl acetate, which was washed with water and dried (MgSO$_4$), then the solvent was distilled off to leave the title compound as colorless crystals (3.7 g).
m.p.217°–220° C. (recrystallized from ethyl acetate isopropyl ether)
NMR (200 MHz,CDCl$_3$) ppm: 2.22(3H,s), 2.37(3H,s), 3.63(2H,s), 3.67(3H,s), 5.90(1H,bs), 6.75(1H,s), 7.20–7.35(2H,m), 7.40–7.55(3H,m), 8.24(1H,s)
Elemental Analysis for C$_{20}$H$_{19}$NO$_3$:
  Calcd.: C, 74.75; H, 5.96; N, 4.36
  Found: C, 74.69; H, 6.08; N, 4.23

By substantially the same procedure as in Step 1 and 2 of Reference Example 7, 1,2-dihydro-3-methanesulfonyloxymethyl-1-oxoisoquinolines having the corresponding substituents were allowed to react with sodium cyanide (Step 1), then the reaction mixture was subjected to acid hydrolysis (Step 2) to give compounds of Reference Examples 8 and 9. Physico-chemical data of the compounds obtained in each step were set forth as follows.

Reference Example 8

Step 1

3-Cyanomethyl-1,2-dihydro-2-methyl-1-oxo-4-phenylisoquinoline m.p.253°–255° C. (recrystallized from ethyl acetate methanol)
NMR (200 MHz,CDCl$_3$) ppm: 3.60(2H,s), 3.85(3H,s), 7.02–7.07(1H,m), 7.28–7.59(7H,m), 8.49–8.54(1H,m)

Step 2

1,2-Dihydro-2-methyl-1-oxo-4-phenyl-3-isoquinoline acetic acid
m.p.200°–201° C. (recrystallized from ethyl acetate acetone)
NMR (200 MHz,CDCl$_3$) ppm: 3.67(2H,s), 3.69(3H,s), 6.99–7.04(1H,m), 7.26–7.53(7H,m), 8.47–8.52(1H,m)

Reference Example 9

Step 1

6-Chloro-3-cyanomethyl-1,2-dihydro-2-methyl-1-oxo-4-phenylisoquinoline
m.p.229°–231° C. (recrystallized from ethyl acetate)
NMR (200 MHz,CDCl$_3$) ppm: 3.58(2H,s), 3.83(3H,s), 6.99(1H,d,J=0.8 Hz), 7.26–7.58(6H,m), 8.44(1H,d,J=8.8 Hz)

Step 2

6-Chloro-1,2-dihydro-2-methyl-1-oxo-4-phenyl-3-isoquinoline acetic acid
m.p.216°–217° C. (recrystallized from ethyl acetate-acetone)
NMR (200 MHz,CDCl$_3$) ppm: 3.65(2H,s), 3.66(3H,s), 6.96(1H,d,J=0.9 Hz), 7.23–7.51(6H,m), 8.41(1H,d,J=8.6 Hz)

Reference Example 10

3-(1,2,Dihydro-2,6,7-trimethyl-1-oxo-4-phenylisoqinolin-3-yl)propionic acid

Step 1

To a solution 1,2-dihydro-3-hydroxymethyl-2,6,7-trimethyl-1-oxo-4-phenylisoquinoline(Reference Example 1) (1.44 g) in DMSO (30 ml) were added triethylamine (2.25 ml) and sulfur trioxide pyridine complex (2.5 g). The mixture was stirred for 15 minutes at room temperature. To the reaction mixture was added chloroform, which was washed with 2N-HCl and water, followed by drying (MgSO$_4$). The solvent was distilled off to leave 1,2-dihydro-2,6,7-trimethyl-1-oxo-4 -phenyl-3-isoquinolinecarboaldehyde as colorless crystals (1.03 g).
m.p.178°–179° C. (recrystallized from ether-hexane)
NMR (200 MHz,CDCl$_3$) ppm:2,27(3H,s), 2.43(3H,s), 3.90(3H,s), 6.96(1H,s), 7.30–7.40(2H,m), 7.48–7.563H,m), 8.32(1H,s), 9.52(1H,s)
Elemental Analysis for C$_{19}$H$_{17}$NO$_2$:
  Calcd.: C, 78,33; H, 5.88; N, 4.81
  Found: C, 78.46; H, 5.90; N, 4.67

Step 2

A mixture of ethyl diethyl phoshonoacetate (1.66 g), sodium hydride (60% oil) (330 mg) and DMF (50 ml) was stirred for 30 minutes at room temperature. This mixture was cooled to 0° C., to which was added the compound (2.05 g) obtained in Step 1. The mixture was stirred for 20 minutes at room temperature. The reaction mixture was poured into dilute hydrochloric acid, which was extracted with ethyl acetate. The extract was washed with water, dried (MgSO$_4$) and the solvent was distilled off to leave (E)-3-(1,2-dihydro-2,6,7-trimethyl-1-oxo-4-phenylisoquinolin-3-yl)propenic acid ethyl ester as colorless crystals (1.84 g).
m.p.143°–145° C. (recrystallized from ethyl acetate-isopropyl ether)
NMR (200 MHz,CDCl$_3$) ppm: 1.23(3H,t,J=7.2 Hz), 2.24(3H,s), 2.39(3H,s), 3.66(3H,s), 4.13(2H,q,J=7.2 Hz), 5.71(1H,d,J=16 Hz), 6.86(1H,s), 7.15–7.24 (2H,m), 7.34(1H,d,J=16 Hz), 7.36–7.50(3H,m), 8.25(1H,s)
Elemental Analysis for C$_{23}$H$_{23}$NO$_3$:
  Calcd.: C, 76.43; H, 6.41; N, 3.88
  Found: C, 76.15; H, 6.43; N, 3.83

Step 3

A mixture of the compound (1.0 g) obtained in Step 2, 10% palladium-carbon (300 mg), THF (15 ml) and ethanol (15 ml) was stirred for 1.5 hours at room temperature under hydrogen atmosphere. The catalyst was filtered off. From the filtrate was distilled off the solvent. The residue was dissolved in ethyl acetate, which was washed with 2N-HCl, an aqueous solution of sodium hydrogencarbonate and water, successively, followed by drying (MgSO$_4$). The solvent was distilled off to leave 3-(1,2-dihydro-2,6,7 -trimethyl-1-oxo-4-phenylisoquinolin-3-yl)propionic acid ethyl ester as colorless crystals (0.85 g).
m.p.138°–139° C. (recrystallized from ethyl acetate isopropyl ether)
NMR (200 MHz,CDCl$_3$) ppm:1.20(3H,t,J=7.1 Hz), 2.21(3H,s), 2.37(3H,s), 2.43(2H,t like, J=8.2 Hz), 2.85(2H,t like, J=8.2 Hz), 3.70(3H,s), 4.07(2H,q,J=7.1 Hz), 6.65(1H, s), 7.15–7.30(2H,m), 7.40–7.55(3H,m), 8.21(1H,s)
Elemental Analysis for C$_{23}$H$_{25}$NO$_3$:
  Calcd.: C, 76.01; H, 6.93; N, 3.85
  Found: C, 76.28; H, 6.92; N, 3.87

Step 4

A mixture of the compound (825 mg) obtained in Step 3, THF (5 ml), ethanol (20 ml) and 1N-sodium hydroxide (5 ml) was stirred for 2 hours at room temperature. The reaction mixture was concentrated, to which was added water. The mixture was washed with ether. The aqueous layer was made acidic with 2N-HCl, which was extracted with ethyl acetate –THF. The extract solution was washed with an aqueous solution of sodium chloride, then dried (MgSO$_4$). The solvent was distilled off to give the title compound as colorless crystals (678 mg).
m.p.261°–162° C. (recrystallized from THF-isopropyl ether).
NMR (200 MHz, CDCl$_3$) ppm: 2.21(3H,s), 2.36(3H,s), 2.43(2H,t like,J=8.2 Hz), 2.84(2H,t like,J=8.2 Hz), 3.71(3H, s), 6.64(1H,s), 7.18–7.30(2H,m), 7.40–7.55(3H,m), 8.20(1H,s)
Elemental Analysis for C$_{21}$H$_{21}$NO$_3$:
  Calcd.: C, 75.20; H, 6.31; N, 4.18
  Found: C, 75.61; H, 6.38; N, 4.10

EXAMPLE 1

N-[(6-Chloro-1,2-dihydro-2-methyl-1-oxo-4 -phenylisoquinolin-3-yl)methyl]-N'-(3isopropoxyphenyl)urea Method A To a benzene (100 ml) solution of 3-isopropoxyphenylisocyanate [prepared by adding diphenylphosphorylazide (3.09 ml) and triethylamine (2.01 ml) to a suspension of 3-isopropoxybenzoic acid (2.16 g ) in benzene (100 ml), and the mixture was stirred for 20 minutes at room temperature, then stirred for 40 minutes by heating under reflux] was added 3-aminomethyl-6-chloro-1,2-dihydro-2-methyl-1-oxo-4-phenylisoquinoline (Reference Example 6 Step 2) (3.0 g). The mixture was heated for 1.5 hour under reflux. The solvent was distilled off. To the residue was added ethyl acetate. This mixture was washed with water, dilute hydrochloric acid, water, an aqueous solution of sodium carbonate and water, successively, which was then dried ($Na_2SO_4$), followed by distilling off the solvent to leave the title compound as colorless crystals (3.91 g),
m.p.257°–259° C. (recrystallized from THF).
NMR (200 MHz,$CDCl_3$)ppm: 1.32(6H,d,J=6 Hz), 3.70(3H, s), 3.75(1H,b), 4.27(2H,bs), 4.53(1H,quintet), 5.29(1H,b), 6.59–7.53(11H,m), 8.29(1H,d,J=8.6 Hz)
Elemental Analysis for $C_{27}H_{26}N_3O_3Cl$:
 Calcd.: C, 68.13; H, 5.51; N, 8.83
 Found : C, 67.90; H, 5.70; N, 8.71

Method B

To a mixture of 6-chloro-1,2-dihydro-2-methyl-1-oxo-4-phenyl-3-isoquinoline acetic acid (Reference Example 9 Step 2) (330 mg), diphenylphosphoryl azide (0.29 ml) and benzene (20 ml) was added dropwise triethylamine (0.14 ml) while stirring at room temperature. This mixture was stirred for one hour at room temperature, then for 30 minutes by heating under reflux {in the reaction mixture, (6-chloro-1,2-dihydro-2-methyl-1-oxo-4-phenylisoquinolin-3-yl)methyl isocyanate was produced}, to which was then added 3-isopropoxyaniline (180 mg). The mixture was heated for 30 minutes under reflux. The solvent was distilled off. To the residue was added ethyl acetate. This mixture was washed with water, dilute hydrochloric acid, water, an aqueous solution of sodium hydrogencarbonate and water, successively, which was dried ($Na_2SO_4$), followed by distilling off the solvent to give the title compound as colorless crystals (390 mg). The physico-chemical data of this product were in agreement with those of the compound obtained in Method A.

By substantially the same procedure as in Method A or Method B in Example 1, reactions were allowed to proceed using amines and isocyanates having respectively corresponding substituents afforded compounds of Examples 2 to 16. Production examples in accordance with Method B were described as (B) after the respective compounds. Examples which do not bear (B) after the compounds are those in accordance with Method A.

EXAMPLE 2

N-[(1,2-Dihydro-2,6,7-trimethyl-1-oxo-4-phenylisoquinolin-3-yl)methyl]-N'-(3-methylphenyl)urea
m.p.262°–264° C. (recrystallized from ethanol).
NMR (200 MHz,$CDCl_3$) ppm:2.09(3H,s), 2.24(3H,s), 2.30(3H,s), 3.62(3H,s), 4.18(2H,d,J=4.4 Hz), 5.85(1H,b), 6.45(1H,s), 6.81(9H,m), 7.67(1H,s), 8.06(1H,s)

EXAMPLE 3

N-[(1,2-Dihydro-2-methyl-1-oxo-4-phenylisoquinolin-3yl)methyl]-N'-(3-methylphenyl)urea
m.p. 240°–242° C. (recrystallized from chloroform-isopropyl ether)
NMR (200 MHz,$CDCl_3$) ppm:2.30(3H,s), 3.68(3H,s), 4.26(2H,d,J=5 Hz), 5.54(1H,b), 6.77–7.49(13,m), 8.33–8.40(1H,m)

EXAMPLE 4

N-[(6-Chloro-1,2-dihydro-2-methyl-1-oxo-4-phenylisoquinolin-3-yl)methyl]-N'-(3-methylphenyl)urea
m.p. 257°–259° C. (recrystallized from ethanol)
NMR (200 MHz,$CDCl_3$) ppm: 2.30(3H,s), 3.66(3H,s), 4.24(2H,d,J=4.8 Hz), 5.54(1H,b), 6.77–7.49(12H,m), 8.23(1H,d,J=8.6 Hz)

Example 5

N-(2,4-Difluorophenyl)-N'-[(1,2-dihydro-2-methyl-1-oxo-4-phenylisoquinolin-3-yl)methyl]urea
m.p. 241°–243° C. (recrystallized from ethanol)
NMR (200 MHz,$CDCl_3$) ppm: 3.69(3H,s), 4.28(2H,d,J=4.6 Hz), 6.21(1H,b), 6.72–6.87(3H,m), 7.13–7.48(7H,m), 7.74(1H,b), 8.00–8.13(1H,m), 8.29–8.33(1H,m)

EXAMPLE 6

N-[(6-Chloro-1,2-dihydro-2-methyl-1-oxo-4-phenylisoquinolin-3-yl)methyl]-N'-(2,4-difluorophenyl)urea
m.p. 258°–260° C. (recrystallized from ethanol)
NMR(200 MHz,$CDCl_3$) ppm: 3.74(3H,s), 4.27(2H,d,J=5.4 Hz), 6.51(1H,b), 6.74–7.52(9H,m), 8.01(1H,b), 8.07–8.20(1H,m), 8.41(1H,d,J=8.8 Hz)

EXAMPLE 7

N-[(6-Chloro-1,2-dihydro-2-methyl-1-oxo-4-phenylisoquinolin-3-yl)methyl]-N'-(3-isoproposyphenyl)-N-methylurea
m.p. 177°–178° C. (recrystallized from acetone-isoprophyl ether)
NMR (200 MHz,$CDCl_3$) ppm: 1.32(6H,d,J=6 Hz), 2.76(3H, s), 3.65(3H,s), 4.53(1H,quintet), 4.65(2H,s), 6.31(1H,b), 6.57–7.53(11H,m), 8.44(1H,d,J=8.6 Hz)

EXAMPLE 8

N-[(6-Chloro-1,2-dihydro-2-methyl-1-oxo-4-phenyl-lisoquinolin-3-yl)methyl]-N'-(3-ethoxycarbonylphenyl)urea (B)
m.p. 223°–226° C. (recrystallized from ethyl acetate isopropyl ether) 4.29(2H,d,j=3.0 Hz), 4.34(2H,q,j=7.0 Hz), 5.7(1H,b),
NMR (200 MHz,$CDCl_3$) ppm: 1.36(3H,t,J=7.0 Hz), 3.70(3H,s), 6.81(1H,d,j=1.8 Hz), 7.1–7.2(2H,m), 7.3–7.4(2H,m), 7.5(3H,m), 7.6–7.8(2H,m), 7.84(1H,s), 8.23(1H,d,J=8–6 Hz)

EXAMPLE 9

N-[(6-Chloro-1,2-dihydro-2-methyl-1-oxo-4-phenylisoquinolin-3-yl)methyl]-N'-(4-ethoxycarbonylphenyl)urea (B)
m.p. 232°–234° C. (recrystallized from ethyl acetate-isopropyl ether)
NMR (200 MHz,$CDCl_3$) ppm: 1.38(3H,t,J=7.0 Hz), 3.66(3H,s), 4.27(2H,m), 4–34(2H,q,J=7.0 Hz), 5.8(1H,b), 6.77(1H,d,J=2.0 Hz), 7.12(1H,m), 7.27(1H,m), 7.4–7.6(4H, m), 7.83(1H,s), 7–95(2H,d,J=8.8 Hz), 8.20(1H,d,J=8.6 Hz)

EXAMPLE 10

N-[(6-Chloro-1,2-dihydro-2-methyl-1-oxo-4-phenylisoquinolin-3-yl)methyl]-N'-(2-ethoxycarbonylphenyl)urea (B)
m.p. 245°–247° C. (recrystallized from ethyl acetate isopropyl ether)

NMR (200 MHz,CDCl₃) ppm: 1.39(3H,t,J=7.2 Hz), 3.75(3H,s), 4.33(2H,q,J=7.2 Hz), 4.36(2H,d,J=7.0 Hz), 5.07(1H,b), 6.90(1H,d,J=1.8 Hz), 6.98(1H,t,J=8.2 Hz), 7.3–7.4(3H,m), 7.5–7.6(4H,m), 8.00(1H,dd,J=8.0 Hz,J=1.4 Hz), 8.35(1H,d,J=8.4 Hz), 8.45(1H,d,J=7.8 Hz)

EXAMPLE 11

N-[(6-Chloro-1,2-dihydro-2-methyl-1-oxo-4 -phenylisoquinolin-3-yl)methyl]-N'-(3-methoxycarbonylmethoxyphenyl) urea (B)

m.p. 198°–200° C. (recrystallized from ethyl acetate isopropyl ether)

NMR (200 MHz,CDCl₃) ppm: 3.68(3H,s), 3.78(3H,s), 4.28(2H,d,J=4.8 Hz), 4.61(2H,s), 5.43(1H,b), 6.58(1H,dd, J=8.4 Hz,J=2.2 Hz), 6.83(1H,d,J=2.0 Hz), 6.93(1H,d,J=8.8 Hz), 7.02(1H,s), 7.1–7.2(3H,m), 7.31(1H,dd,J=8.4 Hz,J=1.8 Hz), 7.4–7.6(3H,m), 8.27(1H,d,J=8.6 Hz)

EXAMPLE 12

N-[(6-Chloro-1,2-dihydro-2-methyl-1-oxo-4 -phenylisoquinolin-3-yl)methyl]-N'-(3-methoxycarbonylmethyl)urea (B)

m.p. 177°–180° C. (recrystallized from ethyl acetate isopropyl ether)

NMR (200 MHz,CDCl₃) ppm: 3.56(2H,s), 3.63(3H,s), 3.66(3H,s), 4.25(2H,d,J=5.0 Hz), 5.55(1H,b), 6.80(1H,d,J= 1.8 Hz), 6.90(1H,m), 7.1–7.3(7H,m), 7.4–7.5(2H,m), 8.23(1H,d,J=8.6 Hz)

EXAMPLE 13

N-[(6-Chloro-1,2-dihydro-2-methyl-1-oxo-4 -phenylisoquinolin-3-yl)methyl]-N'-(3 -isopropoxyphenyl) -N'-methoxycarbonylmethyl urea (B)

NMR (200 MHz,CDCl₃) ppm: 1.32(6H,d,J=6.2 Hz), 3.73(3H,s), 3.74(3H,s), 4.24(2H,m), 4.31(2H,s), 4.51(1H, m), 6.8–7.0(6H,m), 7.3–7.5(5H,m), 8.40(1H,d,J=8.4 Hz)

This product obtained as colorless crystals was converted into the compound of Example 22 without purification.

EXAMPLE 14

(1) N-[(6-Chloro-1,2-dihydro-2-methyl-1-oxo-4 -phenyl isoquinolin-3-yl)methyl]-N'-(3 -N,N-dimethylaminophenyl)urea (B)

m.p. 252°–254° C. (recrystallized from ethyl acetate isopropyl ether)

NMR (200 MHz,CDCl₃) ppm: 2.92(6H,s), 3.96(3H,s), 4.27(2H,d,j=5.0 Hz), 5.3(1H,b), 6.4–6.5(2H,m), 6.7–6.9(2H,m), 7.1–7.2(3H,m), 7.3–7.4(2H,m), 7.4–7.5(2H, m), 8.29(1H,d,J=8.6 Hz)

(2) N-[(6-Chloro-1,2-dihydro-2-methyl-1-oxo-4 -phenyl isoquinolin-3-yl)methyl]-N'-(3 -N,N-dimethylaminophenyl)urea hydrochloride In a mixture of methanol (5 ml) and ethyl acetate (5 ml) was dissolved the compound (180 mg) obtained in Example 14 (1). To the solution was added 4N HCl-ethyl acetate (3 ml). This mixture was concentrated, to which was added ethyl ether to give the title compound as a white powdery product (180 mg). NMR (200 MHz,DMSO-d₆) ppm: 3.02(6H,s), 3.63(3H,s), 4.14(2H,d,j=3.8 Hz), 6.84(1H,d,j= 2.2 Hz), 6.8–6.9(1H,m), 6.9–7.0(1H,b), 7,1–7.2(1H,m), 7.2–7.3(1H,m), 7.4–7.5(3H,m), 7.5–7.6(4H,m), 8.32(1H,d, J=8.4 Hz), 9.0(1H,b)

EXAMPLE 15

(1) N-[(6-Chloro-1,2-dihydro-2-methyl-1-oxo-4 -phenyl isoquinolin-3-yl)methyl]-N'-(3 -N,N-dimethylaminomethylphenyl)urea (B)

m.p. 204°–206° C. (recrystallized from ethyl acetate-isopropyl ether)

NMR (200 MHz,CDCl₃) ppm: 2.22(6H,s), 3.40(2H,s), 3.69(3H,s), 4.26(2H,d,J=5.0 Hz), 5.55(1H,b), 6.80(1H,d,J= 2.0 Hz), 6.9–7.1(2H,m), 7.1–7.2(2H,m), 7.2–7.4(4H,m), 7.4–7.5(2H,m), 8.25(1H,d,J=8.4 Hz)

(2) N-[(6-Chloro-1,2-dihydro-2-methyl-1-oxo-4-phenyl isoquinolin-3-yl)methyl]-N'-(3-N,N-dimethylaminomethylphenyl)urea hydrochloride Using the compound obtained in Example 15 (1), substantially the same procedure as in Example 14 (2) was followed to afford the title compound as a white powdery product.

NMR (200 MHz,DMSO-d₆) ppm: 2.68(6H,d,J=4.6 Hz), 3.63(3H,s), 4.1–4.2(2H,m), 6.84(1H,d,J=2.0 Hz), 6.99(1H, b), 7.07(1H,d,J=6.4 Hz), 7.31(1H,t,J=7.4 Hz), 7.4–7.5(3H, m), 7.5–7.6(5H,m), 8.33(1H,d,J=6.8 Hz), 9.0(1H,bs)

EXAMPLE 16

N-[(1,2-Dihydro-2-methyl-1-oxo-4-phenylisoquinolin-3yl) methyl]-N'-(3-isopropoxyphenyl)urea m.p. 205°–207° C. (recrystallized from ethyl acetate-methanol)

NMR (200 MHz,CDCl₃) ppm:1.31(6H,d,J=6.0 Hz), 3.68(3H,s), 4.26(2H,d,J=4.8 Hz), 4.53(1H,m), 5.53(1H,m), 6.58(1H,m), 6.7–6.9(2H,m), 7.0–7.1(3H,m), 7.15(1H,t,J= 8.0 Hz), 7.3–7.5(5H,m), 8.36(1H,m)

EXAMPLE 17

(1) N-(3-Carboxyphenyl)-N'-[(6-chloro-1,2-dihydro-2 -methyl-1-oxo-4-phenylisoquinolin-3-yl)methyl]urea To a mixture of a solution of the compound (0.88 g) obtained in Example 8 in ethanol (20 ml) and THF (40 ml) was added an aqueous solution of sodium hydroxide (1.0 g/30 ml). The mixture was stirred for 10 hours at room temperature. The solvent was distilled off. To the residue was added 2N-HCl to make it acidic, which was subjected to extraction with ethyl acetate. The extract was washed with water, and dried MgSO₄, followed by distilling off the solvent to leave the title compound as colorless crystals (0.74 g).

m.p. 236°–239° C. (recrystallized from ethyl acetate isopropyl ether)

NMR (200 MHz,DMSO-d₆) ppm: 3.63(3H,s), 4.16(2H,d,J= 5.0 Hz), 6.6(1H,b), 6.85(1H,d,J=2.0 Hz), 7.3–7.4(3H,m), 7.4–7.6(6H,m), 8.03(1H,s), 8.33(1H,d,J=8.6 Hz), 8.67(1H, bs)

(2) N-(3-Carboxyphenyl)-N'-[(6-chloro-1,2-dihydro-2 -methyl-1-oxo-4-phenylisoquinolin-3-yl)methyl]urea sodium salt To the compound (0.74 g) of Example 17 were added 1N-NaOH (1.6 ml) and water (30 ml) to make a homogeneous solution, which was then subjected to filtration. The filtrate was lyophilized to give a white powdery product.

NMR (200 MHz,DMSO-d₆) ppm: 3.64(3H,s), 4.14(2H,d,J= 5.0 Hz), 6.86(1H,d,J=2,2 Hz), 7.00(1H,t,J=7.8 Hz), 7.25(1H,d,J=7.4 Hz), 7.4–7.6(6H,m), 7.72(1H,s), 7.81(1H, d,J=8.0 Hz), 8.33(1H,d,8.8 Hz), 8.8(1H,b)

In substantially the same manner as in Example 17, compounds having a caroxylic acid ester group were subjected to alkali hydrolysis, followed by work-up to give compounds of Examples 18 to 22.

EXAMPLE 18

(1) N-(4-Carboxyphenyl)-N'-[(6-chloro-1,2-dihydro-2-methyl-1-oxo-4-phenylisoquinolin-3-yl)methyl]urea
m.p. 225°–228° C. (recrystallized from ethyl acetate isopropyl ether)

(2) N-(4-Carboxyphenyl)-N'-[(6-chloro-1,2-dihydro-2-methyl-1-oxo-4-phenylisoquinolin-3-yl)methyl]urea sodium salt A white powdery product
NMR (200 MHz,DMSO-$d_6$): 3.62(3H,s), 4.13(2H,m), 6.85(1H,d,J=1.8 Hz), 7.31(2H,d,J=8.6 Hz), 7.3–7.6(6H,m), 7.68(2H,d,J=8.6 Hz), 8.33(1H,d,J=8.4 Hz), 9.6(1H,b)

EXAMPLE 19

(1) N-(2-Carboxyphenyl)-N'-[(6-chloro-1,2-dihydro-2-methyl-1-oxo-4-phenylisoquinolin-3-yl)methyl]urea
m.p. 240°–242° C. (recrystallized from ethyl acetate isopropyl ether)

(2) N-(2-Carboxyphenyl)-N'-[(6-chloro-1,2-dihydro-2-methyl-1-oxo-4-phenylisoquinolin-3-yl)methyl]urea sodium salt A white powdery product
NMR (200 MHz,DMSO-$d_6$) ppm:3.53(2H,d,J=8.0 Hz), 3.69(3H,s), 6.64(1H,s), 7.0–7.2(4H,m), 7.2–7.3(3H,m), 7.5–7.8(3H,m), 8.28(1H,d,J=8.4 Hz)

EXAMPLE 20

(1) N-(3-Carboxymethoxyphenyl)-N'-[(6-chloro-1,2-dihydro-2-methyl-1-oxo-4-phenylisoquinolin-3yl)methyl]urea
m.p. 223°–225° C. (recrystallized from ethyl acetate methanol)

(2) N-(3-Carboxymethoxyphenyl)-N'-[(6-chloro-1,2-dihydro-2-methyl-1-oxo-4-phenylisoquinolin-3-yl)methyl]urea sodium salt A white powdery product
NMR (200 MHz,DMSO-$d_6$) ppm: 3.59(3H,s), 4.09(4H,m), 6.32(1H,d,J=8.4 Hz), 6.76(1H,s), 6.82(1H,d,J=1.6 Hz), 6.98(1H,t,J=8.4 Hz), 7.16(1H,d,J=8.6 Hz), 7.4–7.6(6H,m), 7.7(1H,b), 8.31(1H,d,J=8.4 Hz), 9.77(1H,b)

EXAMPLE 21

N-(3-Carboxymethylphenyl)-N'-[(6-chloro-1,2-dihydro-2-methyl-1-oxo-4-phenylisoquinolin-3-yl)methyl]urea sodium salt A white powdery product
NMR (200 MHz, DMSO-$d_6$) ppm: 3.10(2H,s), 3.58(3H,s), 4.05(2H,d,J=4.0 Hz), 6.56(1H,d,J=6.6 Hz), 6.85(1H,d,J=2.2 Hz), 6.95(1H,t,J=7.4 Hz), 7.4–7.6(7H,m), 7.73 (1H,d,J=6.0 Hz ), 8.32(1H,d,J=8.4 Hz), 9.05(1H,b)

EXAMPLE 22

N-Carboxymethyl-N'-[(6-chloro-1,2-dihydro-2-methyl-1-oxo-4-phenylisoquinolin-3-yl)methyl]-N-(3isopropoxyphenyl)urea sodium salt A while powdery product
NMR (200 MHz,DMSO-$d_6$) ppm: 1.23(6H,d,J=6.0 Hz), 3.64(3H,s), 3.78(3H,s), 4.05(2H,d,J=4.4 Hz), 4.50(1H,m), 6.60(1H,m), 6.83(1H,d,J=2.0 Hz), 6.9–7.0(2H,m), 7.13(1H,t,J=8.2 Hz), 7.3–7.4(2H,m), 7.5–7.6(4H,m), 8.32(1H,d,J=8.8 Hz), 8.32(1H,b)

EXAMPLE 23

N-[(6-Chloro-1,2-dihydro-2-methyl-1-oxo-4-phenylisoquinolin-3-yl)methyl]-N'-(3-isopropoxyphenyl)-N'-methylurea To a solution of the compound (0.30 g) obtained in Example 1 in DMF (4 ml) was added, while stirring, sodium hydride (60% oil) (33 mg). To the mixture was added methyl iodide (0.055 ml). This mixture was stirred for 30 minutes, which was added to dilute hydrochloric acid, followed by extraction with ethyl acetate. The extract was washed with water, dried ($Na_2SO_4$), followed by distilling off the solvent. The residue was subjected to a chromatography using silica gel (hexane→hexane:ethyl acetate=3:2→3:1) to separate and purify. From the initial fractions, the compound (N-methyl compound) obtained in Example 7 (10 mg) was obtained. From the next fractions, N,N'-dimethyl compound (compound of Example 24) (65 mg), and from the third fractions, N'-methyl compound (title compound) (115 mg) were obtained respectively as colorless crystals.
m.p.185°–186° C. (recrystallized from ethyl acetate-isopropyl ether)
NMR (200 MHz,$CDCl_3$) ppm: 1.33(6H,d,J=6.2 Hz), 3.22(3H,s), 3.74(3H,s), 4.21(2H,d,J=5.8 Hz), 4.32(1H,b), 4.52(1H,m), 6.65–7.43(11H,m),,8.38(1H,d,J=8.2 Hz)
Elemental Analysis for $C_{28}H_{28}N_3O_3Cl$:
  Calcd.: C, 68.63; H, 5.76; N, 8.58
  Found: C, 68.44; H, 5.89; N, 8.44

EXAMPLE 24

N-[(6-Chloro-1,2-dihydro-2-methyl-1-oxo-4-phenylisoquinolin-3-yl)methyl]-N'-(3-isopropoxyphenyl)-N,N'-dimethylurea The title compound was produced in substantially the same manner as in Example 23.
m.p. 143°–144° C. (recrystallized from acetone-isopropyl ether)
NMR (200 MHz,$CDCl_3$) ppm: 1.27(6H,d,J=6.2 Hz), 2.33(3H,s), 3.17(3H,s), 3.67(3H,s), 4.41(2H,s), 4.45(1H,m), 6.49–7.46(11H,m), 8.40(1H,d,J=8.8 Hz)
Elemental Analysis for $C_{29}H_{30}N_3O_3Cl$:
  Calcd.: C, 69.11; H, 6.00; N, 8.34
  Found: C, 68.70; H, 6.05; N, 8.33

EXAMPLE 25

N-[(6-Chloro-1,2-dihydro-2-methyl-1-oxo-4-phenylisoquinolin-3-yl)methyl]-2-indolecarboxamide To a solution of indole-2-carboxylic acid (161 mg) in THF (5 ml) and DMF (one drop) was added oxalyl chloride (0.10 ml). The mixture was stirred for one hour at room temperature. The solvent was distilled off, and the residue was dissolved in dichloromethane (5 ml). This solution was added to a mixture of 3-aminomethyl-6-chloro-1,2-dihydro-2-methyl-4-phenylisoquinoline (Reference Example 6, Step 2) (309 mg), trimethylamine (0.154 ml) and dichloromethane (10 ml) while stirring at 0° C. This mixture was stirred for 3 hours at room temperature, then the solvent was distilled off. To the residue was added water. Resulting crystalline precipitate was collected by filtration, which was washed with water and acetone successively to afford the title compound as colorless crystals (277 mg).
m.p. >305° C. (recrystallized from THF-ethanol) NMR (200 MHz,DMSO-$d_6$) ppm: 3.62(3H,s), 4.33(2H,d,J=3.4 Hz), 6.90(1H,d,J=1.8 Hz), 7.03(1H,t,J=7.3 Hz), 7.18–7.60(10H, m), 8.37(1H,d,J=8.6 Hz), 8.74(1H,b), 11.59(1H,b)

EXAMPLE 26

N-[(1,2-Dihydro-2,6,7-trimethyl-1-oxo-4-phenylisoquinolin-3-yl)methyl]-2-indolecarboxamide By substantially the same procedure as in Example 25, the compound of Reference Example 4 was allowed to react with indole-2-carboxylic acid, and the reaction mixture was worked-up conventionally to obtain the title compound.
m.p. 303°–305° C. (recrystallized from ethyl acetate)
NMR (200 MHz,CDCl$_3$) ppm: 2.06(3H,s), 2.14(3H,s), 3.70(3H,s), 4.46(2H,d,J=4.4 Hz), 6.50(1H,s), 7.08–7.68(10H,m), 7.96(1H,b), 7.98(1H,s), 9.96(1H,b)

In substantially the same procedure as in Example 25, corresponding amines were allowed to react with acid chlorides, and the reaction mixtures were worked-up conventionally to afford compounds of Examples 27 to 28.

EXAMPLE 27

N-(6-Chloro-1,2-dihydro-2-methyl-1-oxo-4 -phenylisoquinolin-3-yl)methyl-α-(3-isopropoxyphenyl)acetamide
m.p. 158°–161° C. (recrystallized from ethyl acetate isopropyl ether)
NMR (200 MHz,CDCl$_3$) ppm: 1.31(6H,d,J=6.0 Hz), 3.52(2H,s), 3.63(3H,s), 4.23(2H,d,J=5.4 Hz), 4.54(1H,m,J= 6.0 Hz), 5.45(1H,b), 6.7–6.8(2H,m), 6.85(2H,m), 7.0(2H, m), 7.28(1H,t,J=7.4 Hz), 7.4–7.5(4H,m), 8.37(1H,d,J=8.4 Hz)

EXAMPLE 28

(1) N-(6-Chloro-1,2-dihydro-2-methyl-1-oxo-4 -phenylisoquinolin-3-yl)methyl-α-(3methoxycarbonylphenyl)acetamide
m.p. 135°–136° C. (recrystallized from ethyl acetate-isopropyl ether)
NMR (200 MHz,CDCl$_3$) ppm: 3.61(3H,s), 3.64(2H,s), 3.92(3H,s), 4.26(2H,d,J=5.2 Hz), 5.79(1H,b), 6.83(1H,d,J= 2.2 Hz), 7.0–7.1(2H,m), 7.32(1H,dd,J=8.6,2.0 Hz), 7.4–7.5(5H,m), 7.95(1H,s), 8.0(1H,m), 8.30(1H,d,J=8.6 Hz)

(2) N-(6-Chloro-1,2-dihydro-2-methyl-1-oxo-4 -phenylisoquinolin-3-yl)methyl-α-(3-carboxyphenyl)acetamide carboxylic acid:
m.p.242°–246° C. (recrystallized from ethyl acetate isopropyl ether)

(3) N-(6-Chloro-1,2-dihydro-2-methyl-1-oxo-4 -phenylisoquinolin-3-yl)methyl-α-(3-carboxyphenyl)acetamide sodium salt White powdery product
NMR (200 MHz,DMSO-d$_6$) ppm: 3.40(2H,s), 3.48(3H,s), 4.03(2H,d,J=3.0 Hz), 6.85(1H,d,J=2.0 Hz), 7.16(2H,m), 7.35(2H,m), 7.4–7.6(3H,m), 7.71(1H,m), 7.78(1H,m), 8.33(1H,d,J=8.4 Hz), 8.5(1H,b)

EXAMPLE 29

3-Isopropoxyphenyl N-[(6-chloro-1,2-dihydro-2-methyl-1 -oxo-4-phenylisoquinolin-3-yl)methyl]carbamate
A mixture of the compound (211 mg) obtained in Step 2 of Reference Example 9, benzene (20 ml), triethylamine (0.108 ml) and diphenylphosphoryl azide (0.195 ml) was stirred for one hour at room temperature and for further one hour by heating under reflux. To this mixture was added 3-isopropoxyphenol (150 mg), which was heated for one hour under reflux. The solvent was distilled off. To the residue was added water, which was extracted with ethyl acetate. The extract was washed with water and dried (MgSO$_4$), then the solvent was distilled off. The residue was purified by subjecting to a silica gel column chromatography (hexane: ethyl acetate=3:1) to give the title compound as colorless crystals (134 mg).
m.p. 158°–160° C. (recrystallized from ethyl acetate-isopropyl ether)
NMR (200 MHz,CDCl$_3$) ppm:1.32(6H,d,J=6.2 Hz), 3.76(3H,s), 4.35(2H,d,J=5.2 Hz), 4.50(1H,m), 5.1(1H,m), 6.6–6.8(3H,m), 6.94(1H,s), 7.2–7.3(3H,m), 7.40(1H,d,J=8.0 Hz), 7.54(3H,m), 8.40(1H,d,J=8.4 Hz)

EXAMPLE 30

Benzyl N-[2-(1,2-dihydro-2,6,7-trimethyl-1-oxo-4 -phenylisoquinolin-3-yl)ethyl]carbamate
To a mixture of 3-(1,2-dihydro-2,6,7-trimethyl-1 -oxo-4-phenylisoquinolin-3-yl)propionic acid (Reference Example 10) (650 mg), triethylamine (0.30 ml) and benzene (20 ml) was added, while stirring at room temperature, diphenyl phosphoryl azide (0.30 ml). This mixture was stirred for 30 minutes at room temperature, then for one hour by heating under reflux. To the reaction mixture was added ethyl acetate, which was washed with water, dilute hydrochloric acid, an aqueous solution of sodium hydrogencarbonate and water, successively, followed by drying (MgSO$_4$). The solvent was distilled off to afford the title compound as a colorless crystals (623 mg).
m.p. 227°–228° C. (recrystallized from ethyl acetate isopropyl ether)
NMR (200 MHz,CDCl$_3$) ppm: 2.20(3H,s), 2.36(3H,s), 2.76(2H,t,J=7.5 Hz), 3.28(2H,bdt), 3.79(3H,s), 4.77(1H,bt), 5.04(2H,s), 6.62(1H,s), 7.18–7.50(10H,m), 8.21(1H,s)
Elemental Analysis for C$_{28}$H$_{28}$N$_2$O$_3$:
Calcd.: C, 76.34; H, 6.41; N, 6.36
Found: C, 76.01; H, 6.49; N, 6.33

EXAMPLE 31

(6-Chloro-1,2-dihydro-2-methyl-1-oxo-4 -phenylisoquinolin-3-yl)methyl N-(3-isopropoxyphenyl)carbamate
To a solution of 3-isopropoxyphenylisocyanate in benzene (25 ml) [prepared from 3-isopropoxybenzoic acid (405 mg) in substantially the same manner as described in Method A of Example 1] was added 6-chloro-1,2 -dihydro-3-hydroxymethyl-2-methyl-1-oxo-4-phenylisoquinoline (Reference Example 3) (300 mg), and the mixture was heated for 1.5 hours under reflux. The solvent was distilled off. To the residue was added ethyl acetate. This mixture was washed with water, dilute hydrochloric acid, water, an aqueous solution of sodium carbonate and water, successively, followed by drying (Na$_2$SO$_4$). The solvent was distilled off to leave the title compound as colorless crystals (435 mg).
m.p. 205°–207° C. (recrystallized from acetone-ethyl ether)
NMR (200 MHz,CDCl$_3$) ppm: 1.32(6H,d,J=6.0 Hz), 3.72(3H,s), 4.52(1H,quintet), 4.96(2H,s), 6.59–7.49(12H, m), 8.44(1H,d,J=8.4 Hz)
Elemental Analysis for C$_2$H$_{25}$N$_2$O$_4$Cl:
Calcd.: C, 67.99; H, 5.28; N, 5.87
Found: C, 67.72; H. 5.36; N. 5.82

EXAMPLE 32

(6-Chloro-1,2-dihydro-2-methyl-1-oxo-4 -phenylisoquinolin-3-yl)methyl α-(3-isopropoxyphenyl)acetate
To a solution of α-(3-isopropoxyphenyl)acetic acid (297 mg) in THF (25 ml) were added DMF (one drop) and oxalyl chloride (0.184 ml) at room temperature, and the mixture was stirred for 30 minutes. The solvent was distilled off, and the residue was dissolved in THF (20 ml). To this solution was added, at room temperature, a solution of the compound obtained in Reference Example (370 mg) and triethylamine (0.215 ml) in THF (20 ml), and the mixture was stirred for one hour. The solvent was distilled off. To the residue was added water, which was extracted with ethyl acetate. The extract was washed with 1N-HCl, an aqueous solution of hydrogencarbonate and water, successively, followed by drying (MgSO$_4$), then the solvent was distilled off. The residue was purified by means of a silica gel column chromatography (hexane:ethyl acetate=3:1→2:1) to give the title compound as colorless crystals (127 mg).
m.p. 130°–132° C. (recrystallized from ethyl acetate isopropyl ether)
NMR (200 MHz,CDCl$_3$)ppm:1.30(6H,d,J=6.2 Hz), 3.56(3H,s), 3.60(2H,s), 4.53(1H,m), 4.85(2H,s), 6.8–6.9(3H,m), 7.04(1H,d,j=1.2 Hz), 7.1–7.3(3H,m), 7.4–7.5(4H,m), 8.44(1H,d,J=8.4 Hz) Compounds of Examples 33 to 35 were produced by substantially the same procedure as in Examples 25 and 26.

EXAMPLE 33

3,5-Bis(trifluoromethyl)-N-[(1,2-dihydro-2,6,7 -trimethyl-1-oxo-4-phenylisoquinolin-3 -yl)methyl]benzamide
m.p. 235°–237° C. (recrystallized from ethyl acetate isopropyl ether)
NMR (200 MHz,CDCl$_3$) ppm:2.02(3H,s), 2.09(3H,s), 3.63(3H,s), 4.46(2H,d,J=3.4 Hz), 6.44(1H,s), 7.35–7.56(5H, m), 7.85(1H,s), 8.02(1H,s), 8.60(1H,bs), 8.80(2H,s)

EXAMPLE 34

3,5-Bis(trifluoromethyl)-N-[(1,2-dihydro-2-methyl-1 -oxo-4-phenylisoquinolin-3-yl)methyl]benzamide
m.p. 228°–230° C. (recrystallized from ethyl acetate isopropyl ether)
NMR (200 MHz,CDCl$_3$) ppm:3.70(3H,s), 4.52(2H,d,J=4.2 Hz), 6.72(1H,s), 7.12–7.21(2H,m), 7.32–7.41(2H,m), 7.45–7.56(3H,m), 8.02(1H,s), 8.17(1H,m), 8.35(1H,bs), 8.73(2H,s)

EXAMPLE 35

3,5-Bis(trifluromethyl)-N-[(6-chloro-1,2-dihydro-2 -methyl-1-oxo-4-phenylisoquinolin-3-yl)methyl]benzamide
m.p. 238°–239° C. (recrystallized from ethyl acetate isopropyl ether)
NMR (200 MHz,CDCl$_3$) ppm:3.64(3H,s), 4.49(2H,d,J=3.8 Hz), 6.75(1H,d,J=1.8 Hz), 7.11(1H,dd,J=8.6,1.8 Hz), 7.33–7.41(2H,m), 7.50–7.60(3H,m), 8.03(1H,s), 8.07(1H,d, J=8.6 Hz), 8.22(1H,bs), 8.70(2H,s)

EXAMPLE 36

3,5-Bis(trifluoromethyl)-N-[(1,2-dihydro-2,6,7 -trimethyl-1-oxo-4-phenylisoquinolin-3-yl)methyl]-N-methylbenzamide
To a solution of the compound (250 mg) obtained in Example 33 in DMF (5 ml) was added sodium hydride (60% oil) (26 mg). The mixture was stirred for 30 minutes at room temperature, to which was added methyl iodide (0.5 ml), followed by stirring for 30 minutes at room temperature. The reaction mixture was poured into water, which was extracted with ethyl acetate. The extract was washed with water and dried (MgSO$_4$). The solvent was distilled off to leave the title compound as colorless crystals (144 mg).
m.p. 223°–224° C. (recrystallized from ethyl acetate isopropyl ether)
NMR (200 MHz,CDCl$_3$) ppm: 2.25(3H,s), 2.41(3H,s), 2.69(3H,s), 3.71(3H,s), 4.83(2H,s), 6.75(1H,s), 7.22–7.29(2H,m), 7.47–7.56(3H,m), 7.78(2H,s), 7.94(1H,s), 8.28(1H,s)

EXAMPLE 37

3,5-Bis(trifluoromethyl)-N-[(1,2-dihydro-2-methyl-1 -oxo-4-phenylisoquinolin-3-yl)methyl]-N-methyl benzamide
The compound obtained in Example 34 was subjected to methylation and worked-up in substantially the same manner as in Example 36 to give the title compound.
m.p. 229°–230° C. (recrystallized from ethyl acetate-isopropyl ether)
NMR (200 MHz,CDCl$_3$) ppm:2.72(3H,s), 3.73(3H,s), 4.87(2H,s), 7.03(1H,m), 7.24–7.32(2H,m), 7.46–7.59(5H, m), 7.79(2H,s), 7.94(1H,s), 8.54(1H,m)

EXAMPLE 38

3,5-Bis(trifluoromethyl)-N-[(6-chloro-1,2-dihydro-2 -methyl-1-oxo-4-phenylisoquinolin-3-yl)methyl]-N-methylbenzamide
The compound obtained in Example 35 was subjected to methylation and worked-up in substantially the same manner as in Example 36 to give the title compound.
m.p. 196°–197° C. (recrystallized from ethyl acetate-isopropyl ether)
NMR (200 MHz ,CDCl$_3$) ppm:2.71(3H,s), 3.71(3H,s), 4.85(2H,s), 6.97 (1H,d,J=1.8 Hz), 7.22–7.31(2H,m), 7.47 (1H,dd,J=8.8 ,1.8 Hz), 7.48–7.59(3H,m), 7.79(2H,s), 7.95(1H,s), 8.46 (1H,d,J=8.8 Hz)

Effects of the Invention

The present invention provides novel heterocyclic compounds and their salts having an excellent action of inhibiting release of calcium from endoplasmic reticulum of neuronal cells for use as therapeutic and prophylactic drugs of cerebral vascular disorders and neuronal disorders such as cerebral ischemic disorders and cerebral edema, and potent tachykinin receptor antagonizing activity, especially having antagonistic activity against substance P-receptor.

Using 6-chloro-1,2-dihydro-2-methyl-1-oxo-4 -phenyl-3-isoquinoline acetic acid, diphenylphosphoryl azide and amines having substituents corresponding to those of Example compounds, reactions were carried out by substantially the same procedure as in Method B of Example 1 to give compounds of Examples 39 to 47. The hydrochlorides of the title compounds were isolated by the procedure described in Example 14(2).

EXAMPLES 39

N-[(6-Chloro-1,2-dihydro-2-methyl-1-oxo-4 -phenylisoquinolin-3-yl)methyl]-N'-[3-(diethylaminomethyl)phenyl] urea
(1) free form
m.p. 196°–198° C. (recrystallized from ethyl acetate-isopropyl ether)
(2) hydrochloride A white powdery produce
NMR(200 MHz,DMSO-d$_6$)ppm: 1.22(6H,t,J=7.4 Hz), 3.03(4H,m), 3.63(3H,s), 4.21(2H,d,J=4.4 Hz), 6-84(1H,d, J=1.8 Hz), 7.04(1H,b), 7.13(1H,m), 7.30(1H,t,J=7.4 Hz), 7.42(3H,m), 7.5–7.6(5H,m), 8.32(1H,d,J=8–6 Hz), 9.06(1H, bs) .

EXAMPLE 40

N-[(6-Chloro-1,2-dihydro-2-methyl-1-oxo-4-phenylisoquinolin-3-yl)methyl]-N'-[3-(1-pyrrolidinomethyl)phenyl]urea (1) free form
m.p. 168°–170° C. (recrystallized from ethyl acetate-isopropyl ether)

(2) hydrochloride A white powdery product NMR (200 MHz,DMSO-$d_6$) ppm: 1.8–2.1(4H,m), 3.0(2H,m), 3.3(2H,m), 3.63(3H,s), 4.14(2H,d,J=4.4 Hz), 4.26(2H,d,J=5.4 Hz), 6.85(1H,d,J=2.0 Hz), 7.04(1H,b), 7.1–7.5(5H,m), 7.5–7.6(5H,m), 8.32(1H,d,J=8.4 Hz), 9.06(1H,bs)

EXAMPLE 41

N-[(6-Chloro-1,2-dihydro-2-methyl-1-oxo-4-phenylisoquinolin-3-yl)methyl]-N'-{3-[2-(diethylamino)ethyl]phenyl}urea (1) free form
m.p. 202°–204° C. (recrystallized from ethyl acetate-isopropyl ether)

(2) hydrochloride A white powdery product NMR (200 MHz,DMSO-$d_6$) ppm: 2.78(3H,s), 2.80(3H,s), 2.90(2H,m), 3.20(2H,m), 3.62(3H,s), 4.13(2H,d,J=4.6 Hz), 6.94(1H,b), 6.95(1H,m), 7.2–7.3(2H,m), 7.3–7.5(3H,m), 7.5–7.6(5H,m), 8.32(1H,d,j=8.6 Hz), 8.94(1H,bs)

EXAMPLE 42

N[(6-Chloro-1,2-dihydro-2-methyl-1-oxo-4-phenylisoquinolin-3-yl)methyl]-N'-[2-(dimethylaminomethyl)phenyl]urea (1) free form
m.p.221°–223° C. (recrystallized from ethyl acetate-isopropyl ether)

(2) hydrochloride A white powdery product NMR (200 MHz,DMSO-$d_6$) ppm: 2.71(3H,s), 2.77(3H,s), 3.65(3H,s), 4.16(2H,d,J=4.0 Hz) 4.45(2H,d,J=4.8 Hz), 6.84 (1H,d,J=2.0 Hz ), 7.09(1H,t,J=7–6 Hz), 7.3–7.6(8H,m), 7.71(1H,b), 7.87(1H,d,J=8.0 Hz), 8.32 (1H,d,J=8.4 Hz ), 9.04 (1H,bs)

EXAMPLE 43

N-[(6-Chloro-1,2-dihydro-2-methyl-1-oxo-4-phenylisoquinolin-3-yl)methyl]-N'-[4-(dimethylaminomethyl)phenyl]urea (1) free form
m.p. 199°–201° C. (recrystallized from ethyl acetate-isopropyl ether)

(2) hydrochloride A white powdery product NMR (200 MHz,DMSO-$d_6$) ppm: 2.64(3H,s), 2.66(3H,s), 3.63(3H,s), 4.14(4H,m), 6.84(1H,d,J=2.0 Hz), 7.03(1H,b), 7.3–7.5(5H,m), 7.5–7.6(5H,m), 8.32(1H,d,J=8.8 Hz), 9.20(1H,bs)

EXAMPLE 44

N-[(6-Chloro-1,2-dihydro-2-methyl-1-oxo-4-phenylisoquinolin-3-yl)methyl]-N'-{3-[3-(dimethylamino)propyl]phenyl}urea (1) free form A colorless oily product NMR (200 MHz, CDCl$_3$) ppm: 1.71(2H,m), 2.18(6H,s), 2.31(2H,m), 2.44(2H,m), 3.57(3H,s), 4.17(2H,s), 6.2(1H,b), 6.7–6.8(2H,m), 7.0–7.2(6H,m), 7.37(3H,m), 8.29(1H,d,J=S.8 Hz), 8.38(1H,b)

(2) hydrochloride A white powdery product NMR (200 MHz,DMSO-$d_6$) ppm: 1.91(2H,m), 2.71(3H,s), 2.73(3H,s), 3.00(2H,m), 3.53(2H,m), 3.63(3H,s), 4.12(2H,m), 6.7–6.8(2H,m), 6.59(1H,b), 7.1–7.3(4H,m), 7.4–7.5(2H,m), 7.5–7.6(3H,m), 8.32(1H,d,j=8.4 Hz), 8.92(1H,bs)

EXAMPLE 45

N-[(6-Chloro-1,2-dihydro-2-methyl-1-oxo-4-phenylisoquinolin-3-yl)methyl]-N'-{3-[2-(dimethylamino)ethoxy]phenyl}urea (1) free form A colorless oily product NMR (200 MHz, CDCl$_3$) ppm: 2.30(6H,s), 2.70(2H,t,J=5.6 Hz), 3.65(3H,s), 4.01(2H,t,J=5.6 Hz), 4.24(2H,d,J=4.4 Hz), 5.65(1H,b), 6.57(1H,m), 6.8–7.2(6H,m), 7.26(1H,m), 7.45(4H,m), 8.27(1H,d,J=8.8 Hz)

(2) hydrochloride A white powdery product NMR (200 MHz,DMSO-$d_6$) ppm: 2.84(3H,s), 2.85(3H,s), 3.50(2H,m), 3.63(3H,s), 4.14(2H,m), 4.27(2H,m), 6.51(1H,m), 6.85(3H,m), 7.1–7.3(3H,m), 7.41(2H,m), 7.4–7.6(3H,m), 8.34(1H,d,J=8.8 Hz), 8.89(1H,bs)

EXAMPLE 46

N-[(6-Chloro-1,2-dihydro-2-methyl-1-oxo-4-phenylisoquinolin-3-yl)methyl]-N'-[3-(dimethylaminomethyl)benzyl]urea (1) free form
m.p. 185°–187° C. (recrystallized from ethyl acetate-isopropyl ether)

(2) hydrochloride A white powdery product NMR (200 MHz,DMSO-$d_6$) ppm: 2.66(3H,s), 2.68(3H,s), 3.58(3H,s), 4.07(2H,m), 4.24(4H,m), 6.6(1H,b), 6.82(1H,s), 7.17(1H,b), 7.3–7.5(5H,m), 7.5–7.6(5H,m), 8.31(1H,d,J=8.8 Hz)

EXAMPLE 47

N-[(6-Chloro-1,2-dihydro-2-methyl-1-oxo-4-phenylisoquinolin-3-yl)methyl]-N'-[3-(1-imidazolyl)propyl]urea (1) free form
m.p. 190°–192° C. (recrystallized from ethyl acetate-isopropyl ether)

(2) hydrochloride A white powdery product NMR (200 MHz,DMSO-$d_6$) ppm: 1.89(2H,m), 2.98(2H,m), 3.58(3H,s), 4.04(2H,s), 4.19(2H,m), 6.63(1H,b), 6.81(1H,s), 7.17(1H,d, J=7.2 Hz), 7.3–7.4(2H,m), 7.5–7.6(4H,m), 7.68(1H,s), 7.82(1H,s), 8.30(1H,d,J=8.8 Hz), 9.21(1H,bs)

EXAMPLE 48

N-[(6-Chloro-1,2-dihydro-2-methyl-1-oxo-4-phenylisoquinolin-3-yl)methyl]-N'-[3-(methylamino)methylphenyl]urea hydrochloride Using 6-chloro-1,2-dihydro-2-methyl-1-oxo-4-phenyl-3-isoquinoline acetic acid, diphenylphosphoryl azide and 3-(N-t-butoxycarbonyl-N-methylaminomethyl)aniline, the reaction was carried out by substantially the same procedure as in Method B of Example 1 to give N-{3-[(N-t-butoxycarbonyl-N-methylamino)methyl]phenyl}-N'[(6-chloro-1,2-dihydro-2-methyl-1-oxo-4-phenylisoquinolin-3-yl)methyl]urea as a colorless oily product. NMR (200 MHz, CDCl$_3$) ppm: 1.38(9H,s), 2.78(3H,s), 3.71(3H,s), 4.29–4.35(4H,m), 5.8(1H,b), 6.60(1H,b), 6.86(1H,d,J=1.8 Hz), 7.1–7.3(5H,m), 7.3–7.6(5H,m), 8.25(1H,d,J=8.8 Hz). The product was reacted with excess hydrochloride in ethyl acetate at room temperature to give the title compound as a white powdery product. NMR (200 MHz,DMSO-$d_6$) ppm: 2.52(3H,m), 3.63(3H,s), 4.03(2H,m), 4.14(2H,d,J=4.6 Hz), 6.84(1H,d,J=2.0 Hz), 7.05(1H,d,J=11.8 Hz), 7.13(1H,b), 7.31(1H,t,J=13.4 Hz), 7.4–7.5(3H,m), 7.54(5H,m), 8.32(1H,d,J=8.6 Hz), 9.01(1H,b), 9.18(1H,bs)

EXAMPLE 49

N-[(6-Chloro-1,2-dihydro-2-methyl-1-oxo-4-phenylisoquinolin-3-yl)methyl]-N'-[3-(ethylaminomethyl)phenyl]urea hydrochloride Using 6-chloro-1,2-dihydro-2-methyl-1-oxo-4-phenyl-3-isoquinoline acetic acid, diphenylphosphoryl azide and 3-(N-t-butoxycarbonyl-N-ethylamino)methylaniline, the reaction was carried out by substantially the same procedure as in Method B of Example 1 to give N-[3-(N-t-butoxycarbonyl-N-ethylamino)methylphenyl]-N'-[(6-chloro-1,2-dihydro-2-methyl-1-oxo-4-phenylisoquinolin-3-yl)methyl]urea as a colorless oily product. NMR (200 MHz,CDCl$_3$) ppm: 1.02(3H,t,J=7.0 Hz), 1.38(9H,s), 3.17(2H,m), 3.72(3H,s), 4.34(4H,m), 5.70(1H,b), 6.8–6.9(2H,m), 6.99(1H,b), 7.1–7.3(4H,m), 7.4–7.5(5H,m), 8.27(1H,d,J=8.6 Hz) The product was reacted with excess hydrochloride in ethyl acetate at room temperature to give the title compound as a a white powdery product. NMR (200 MHz,DMSO-d$_6$) ppm: 1.20(3H,t,J=7.2 Hz), 2.94(2H,m), 3.63(3H,s), 4.04(2H,m), 4.15(2H,d,J=4.8 Hz), 6.84(1H,d,J=2.0 Hz), 7.0–7.1(2H,m), 7.3–7.5(3H,m), 7.5–7.6(6H,m), 8.33(1H,d,J=8.6 Hz), 8.90(1H,b), 9.02(1H,bs)

EXAMPLE 50

N-(1-Aminoindan-5-yl)-N'-[(6-chloro-1,2-dihydro-2-methyl-1-oxo-4-phenylisoquinolin-3-yl)methyl]urea hydrochloride Using 6-chloro-1,2-dihydro-2-methyl-1-oxo-4-phenyl-3-isoquinoline acetic acid, diphenylphosphoryl azide and 1-(t-butoxycarbonylamino)-5-aminoindan, the reaction was carried out by substantially the same procedure as in Method B of Example 1 to give N-[1-(t-butoxycarbonylamino)indan-5-yl]-N'-[(6-chloro-1,2-dihydro-2-methyl-1-oxo-4-phenyl-isoquinolin-3-yl)methyl]urea as a colorless oily product.
m.p. 225°–227° C. (recrystallized from ethyl acetate-isopropyl ether) The product was reacted with excess hydrochloride in ethyl acetate at room temperature to give the title compound as a white powdery product. NMR (200 MHz, DMSO-d$_6$) ppm: 1.98(1H,m), 2.44(1H,m), 2.80(1H,m), 2.93(1H,m), 3.63(3H,s), 4.14(2H,d,J=4.0 Hz), 4.62(1H,m), 6.84(1H,d,J=1.8 Hz), 7.11(1H,b), 7.15(1H,d,J=8.4 Hz), 7.30(1H,d,J=7.4 Hz), 7.4–7.5(2H,m), 7.5–7.6(4H,m), 7.68(1H,s), 8.22(1H,d,J=8.4 Hz), 9.18(1H,bs)

EXAMPLE 51

N-[3-(Aminomethyl)phenyl]-N'-[(6-chloro-1,2-dihydro-2-methyl-1-oxo-4-phenylisoquinolin-3-yl)methyl]urea hydrochloride Using 6-chloro-1,2-dihydro-2-methyl-1-oxo-4-phenyl-3-isoquinoline acetic acid, diphenylphosphoryl azide and 3-(1-phthalimidemethyl)aniline, the reaction was carried out by substantially the same procedure as in Method B of Example 1, followed by treatment of the product with hydrazine to give the free base of the title compound as colorless crystals. NMR (200 MHz, CDCl$_3$) ppm: 3.67(3H,s), 3.81(2H,s), 4.26(2H,d,J=5.0 Hz), 5.55(1H,b), 6.80(1H,d,J=2.0 Hz), 6.98(1H,m), 7.1–7.3(7H,m), 7.4–7.6(3H,m), 8.24(1H,d,J=8.8 Hz) The product was converted to the title compound by treatment with hydrochloride in ethyl acetate. A white powdery product. NMR (200 MHz,DMSO-d$_6$) ppm: 3.63(3H,s), 3.93(2H,m), 4.14(2H,d,J=5.2 Hz), 6.84(1H,d,J=2.2 Hz), 7.01(1H,d,J=7.4 Hz), 7.09(1H,b), 7.2–7.5(3H,m), 7.5–7.6(6H,m), 8.3(2H,b), 8.32(1H,d,J=8.4 Hz), 8.99(1H,bs)

EXAMPLE 52

N-[(1,2-Dihydro-2-methyl-1-oxo-4-phenylisoquinolin-3-yl)methyl]-N'-[3-(dimethylaminomethyl)phenyl]urea hydrochloride Using 1,2-dihydro-2-methyl-1-oxo-4-phenyl-3-isoquinoline acetic acid, diphenylphosphoryl azide and 3-(dimethylaminomethyl)aniline, the reaction was carried out by substantially the same procedure as in Method B of Example 1, followed by treatment of the product with hydrogen chloride in ethyl acetate to give the title compound as a white powdery product. NMR (200 MHz,DMSO-d$_6$) ppm: 2.67(3H,s), 2.69(3H,s), 3.64(3H,s), 4.17(4H,m), 6.9–7.2(4H,m), 7.3–7.7(9H,m), 8.32(1H,m), 9.09(1H,bs)

EXAMPLE 53

N-{[4-(4-Fluorophenyl)-1,2-dihydro-2-methyl-1-oxoisoquinolin-3-yl]methyl}-N'-[3-(dimethylaminomethyl)phenyl]urea hydrochloride Using 4-(4-fluorophenyl)-1,2-dihydro-2-methyl-1-oxo-3-isoquinoline acetic acid which is prepared from 4-(4-fluorophenyl)-2-methyl-1(2H)-isoquinolinone-3carboxylic acid by a carbon elongation reaction similar to the method described in Reference Example 7, diphenylphosphoryl azide and 3(dimethylamino)methylaniline, the reaction was carried out by substantially the same procedure as in Method B of Example 1 to give the free base of the title compound as colorless crystals.
m.p. 154°–156° C. (recrystallized from ethyl acetate-isopropyl ether), which was converted to the title compound by treatment with hydrogen chloride in ethyl acetate. A white powdery product. NMR (200 MHz,DMSO-d$_6$) ppm: 2.67(3H,s), 2.70(3H,s), 3.64(3H,s), 4.20(4H,m), 6.9–7.2(4H,m), 7.3–7.5(6H,m), 7.5–7.7(2H,m), 8.32(1H,d, J=8.2 Hz), 9.01(1H,bs)

What is claimed is:

1. A compound represented by the formula:

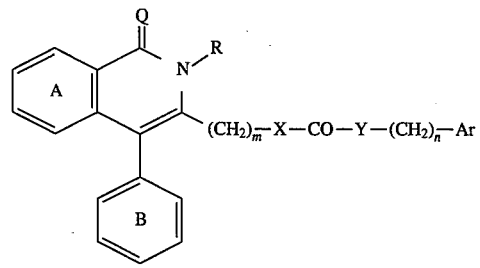

wherein the ring A and the ring B each are a benzene ring which may be substituted with one to four substituents selected from the group consisting of a halogen atom, optionally halogenated alkyl, optionally halogenated alkoxy, optionally halogenated alkylthio, $C_{1-7}$ acylamino, $C_{1-3}$ acyloxy, hydroxyl, nitro, amino, mono- or di-$C_{1-4}$ alkylamino, cyclic amino, $C_{1-4}$ alkyl-carbonylamino, $C_{1-4}$ alkylsulfonylamino, $C_{1-4}$ alkoxy-carbonyl, carboxyl, $C_{1-6}$ alkyl-carbonyl, carbamoyl, imono- or di-$C_{1-4}$ alkylcarbamoyl, and $C_{1-6}$ alkylsulfonyl at any substitutable ring position(s); Ar is (I) an aryl group which may be substituted with the same or different 1 to 5 substituents selected from the group consisting of (a) a halogen atom, (b) a nitro group, (c) a cyano group, (d) a hydroxyl group, (e) an optionally halogenated $C_{1-4}$alkoxy group, (f) a $C_{1-4}$ alkoxy group which may be substituted with a carboxyl group, (g) a $C_{1-4}$ alkoxy group which may be substituted with a $C_{1-4}$ alkoxy-carbonyl group, (h) an optionally halogenated $C_{1-4}$ alkylthio group, (i) an amino group, (j) a mono- or di-$C_{1-4}$ alkylamino group, (k) a cyclic amino group which may be substituted with a $C_{1-4}$ alkyl group, (1) a $C_{1-4}$ alkyl-carbonylamino group, (m) an amino carbonyloxy group, (n) a mono- or di-$C_{1-4}$ alkylaminocarbonyloxy group, (o) a $C_{1-4}$ alkylsulfonylamino group, (p) a $C_{1-4}$ alkoxy-carbonyl group, (g) a benzyloxycarbonyl group, (r) a carboxyl group, (s) a $C_{1-4}$ alkylcarbonyl group, (t) a $C_{3-6}$ cycloalkyl-carbonyl group, (u) a carbamoyl group, (v) a mono- or di-$C_{1-4}$ alkylcarbamoyl group, (w) a $C_{1-6}$ alkylsulfonyl group, and (x) a hydrocarbon group which may be substituted with 1 to 5 substituents selected from the group consisting of (1) a halogen atom, (2) nitro, (3) cyano, (4) hydroxyl, (5) a $C_{1-4}$ alkoxy group, (6) a $C_{1-4}$ alkylthio group, (7) amino, (8) a mono- or di-$C_{1-4}$ alkylamino, (9) a cyclic amino group which may be substituted with a $C_{1-4}$ alkyl group, (10) a $C_{1-4}$ alkyl-carbonylamino group, (11) a $C_{1-4}$ alkylsulfonylamino group, (12) a $C_{1-4}$ alkoxy-carbonyl group, (13) carboxyl, (14) a $C_{1-6}$ alkyl-carbonyl group, (15) carbamoyl, (16) a mono- or di-$C_{1-4}$ alkylcarbamoyl group, (17) a $C_{1-6}$ alkylsulfonyl group, and (18) a phenyl group which may be substituted with a $C_{1-3}$ alkoxy group, at any substitutable position(s) thereof, or (II) a heterocyclic group which may be substituted with the same or different 1 to 5 substituents selected from the group consisting of (a) a halogen atom, (b) a nitro group, (c) cyano, (d) hydroxyl, (e) an optionally halogenated $C_{1-4}$ alkoxy group, (f) a $C_{1-4}$ alkoxy group which may be substituted with a carboxyl group, (g) a $C_{1-4}$ alkoxy group which may be substituted with a $C_{1-4}$ alkoxy-carbonyl group, (h) an optionally halogenated $C_{1-4}$ alkylthio group, (i) an amino group, (j) a mono- or di-$C_{1-4}$ alkylamino group, (k) a cyclic amino group which may be substituted with a $C_{1-4}$ alkyl group, (l) a $C_{1-4}$ alkyl-carbonylamino group, (m) an aminocarbonyloxy group, (o) a $C_{1-4}$ alkylsulfonylamino group, (p) a $C_{1-4}$ alkoxy-carbonyl group, (g) a benzyloxycarbonyl group, (r) a carboxyl group, (s) a $C_{1-4}$ alkylcarbonyl group, (t) a $C_{3-6}$ cycloalkyl-carbonyl group, (u) a carbamoyl group, (v) a mono- or di-$C_{1-4}$ alkylcarbamoyl group, (w) a $C_{1-6}$ alkylsulfonyl group, and (x) a hydrocarbon group which may be substituted with 1 to 5 substituents selected from the group consisting of (1) a halogen atom, (2) nitro, (3) cyano, (4) hydroxyl, (5) a $C_{1-4}$ alkoxy group, (6) a $C_{1-4}$ alkylthio group, amino, (8) a mono- or di-$C_{1-4}$ alkylamino, (9) a cyclic amino group which may be substituted with a $C_{1-4}$ group, (10) a $C_{1-4}$ alkyl-carbonylamino group, (11) a $C_{1-4}$ alkylsulfonylamino group, (12) a $C_{1-4}$ alkoxy-carbonyl group, (13) carboxyl, (14) a $C_{1-6}$ alkyl-carbonyl group, (15) carbamoyl, (16) a mono- or di-$C_{1-4}$ alkylcarbamoyl group, (17) a $C_{1-6}$ alkylsulfonyl group, and (18) a phenyl group which may be substituted with a $C_{1-3}$ alkoxy group, at any substitutable position(s) of the ring; Q is an oxygen atom or a sulfur atom; R is (I) a hydrogen atom, (II) a hydrocarbon group which may be substituted with 1 to 5 substituents selected from the group consisting of (a) a halogen atom, (b) a nitro group, (c) cyano, (d) hydroxyl, (e) an $C_{1-4}$ alkoxy group, (f) a $C_{1-4}$ alkylthio group, (g) amino, (h) a mono- or di-$C_{1-4}$ alkylamino group, (i) a cyclic amino group which may be substituted with a $C_{1-4}$ alkyl group, (j) a $C_{1-4}$ alkyl-carbonylamino group, (k) a $C_{1-4}$ alkylsulfonylamino group, (l) a $C_{1-4}$ alkoxy-carbonyl group, (m) carboxyl, (n) a $C_{1-6}$ alkyl-carbonyl group, (o) carbamoyl, (p) a mono- or di-$C_{1-4}$ alkylcarbamoyl group, (g) a $C_{1-6}$ alkylsulfonyl group, (r) a phenyl group which may be substituted with a $C_{1-3}$ alkoxy group, (III) a hydroxyl group which may be substituted with 1 or 2 substituents selected from the group consisting of (a) a halogen atom, (b) nitro, (c) cyano, (d) hydroxy, (e) a $C_{1-4}$ alkoxy group, (f) a $C_{1-4}$ alkylthio group, (g) amino group, (h) a mono- or di-$C_{1-4}$ alkylamino group, (i) a cyclic amino group which may be substituted with a $C_{1-4}$ alkyl group, (j) a $C_{1-4}$ alkyl-carbonylamino group, (k) a $C_{1-4}$ alkylsulfonylamino group, (1) a $C_{1-4}$ alkoxy-carbonyl group, (o) a carbamoyl group, (p) a mono- or di-$C_{1-4}$ alkylcarbamoyl group, (q) a $C_{1-6}$ alkylsulfonyl group, and (r) a phenyl group which may be substituted with a $C_{1-5}$ alkoxy group, or (IV) an amino group which may be substituted with 1 or 2 substituents selected from the group consisting of (i) a $C_{1-4}$ alkyl group, (ii) a $C_{1-4}$ alkylcarbonyl group, (iii) a $C_{1-4}$ alkoxy-carbonyl group, or (iv) a phenyl group which may be substituted with halogen, a $C_{1-4}$ alkyl group, or a $C_{1-4}$ alkoxy group,;

X is —O— or —$NR^1$— wherein $R^1$ is a hydrogen atom or a hydrocarbon group which may be substituted with 1 to 5 substituents selected from the group consisting of (a) a halogen atom, (b) nitro, (c) cyano, (d) hydroxyl, (e) a $C_{1-4}$ alkoxy group, (f) a $C_{1-4}$ alkylthio group, (g) amino, (h) a mono- or di-$C_{1-4}$ alkylamino, (i) a cyclic amino group which may be substituted with a $C_{1-4}$ alkyl group, (j) a $C_{1-4}$ alkyl-carbonylamino group, (k) a $C_{1-4}$ alkylsulfonylamino group, (l) a $C_{1-4}$ alkoxy-carbonyl group, (m) carboxyl, (n) a $C_{1-6}$ alkyl-carbonyl group, (o) carbamoyl, (p) a mono- or di-$C_{1-4}$ alkylcarbamoyl group, (q) a $C_{1-6}$ alkylsulfonyl group, and (r) a phenyl group which may be substituted with a $C_{1-3}$ alkoxy group; Y is (I) —O—, (II) —$NR^2$— wherein $R^2$ is a hydrogen atom or hydrocarbon group which may be substituted with 1 to 5 substituents selected from the group consisting of (a) a halogen atom, (b) a nitro group, (c) cyano, (d) hydroxyl, (e) an $C_{1-4}$ alkoxy group, (f) a $C_{1-4}$ alkylthio group, (g) amino, (h) a mono- or di-$C_{1-4}$ alkylamino group, (i) a cyclic amino group which may be substituted with a $C_{1-4}$ alkyl group, (j) a $C_{1-4}$ alkyl-carbonylamino group, (k) a $C_{1-4}$ alkylsulfonylamino group, (l) a $C_{1-4}$ alkoxy-carbonyl group, (m) carboxyl, (n) a $C_{1-6}$ alkyl-carbonyl group, (o) carbamoyl, (p) a mono- or di-$C_{1-4}$ alkylcarbamoyl group, (g) a $C_{1-6}$ alkylsulfonyl group, and (r) a phenyl group which may be substituted with a $C_{1-3}$ alkoxy group, or (III) a bond; m denotes 1, 2 or 3, and n denotes 0, 1 or 2, or a salt thereof.

2. A compound as claimed in claim 1, wherein the ring A and the ring B each are a benzene ring which may be substituted with 1 to 4 substituents selected from the group consisting of a halogen atom, optionally halogenated $C_{1-6}$ alkyl group, optionally halogenated $C_{1-6}$ alkoxy group, optionally halogenated $C_{1-6}$ alkylthio group, $C_{1-7}$ acylamino group, $C_{1-7}$ acyloxy group, hydroxyl group, nitro group, cyano group, amino group, mono- or di-$C_{1-4}$ alkylamino group, pyrrolidino group, piperidino group, morpholino group, $C_{1-4}$ alkyl-carbonyl group, $C_{1-4}$ alkylsulfonylamino group, carboxyl group, $C_{1-6}$ alkyl-carbonyl group, $C_{1-4}$ alkoxy-carbonyl group, carbamoyl group, mono- or di-$C_{1-4}$ alkylcarbamoyl group and $C_{1-6}$ alkylsulfonyl group.

3. A compound as claimed in claim 1, wherein the ring A and the ring B each are a benzene ring which may be substituted with 1 to 3 substituents selected from the group consisting of a halogen atom, optionally halogenated $C_{1-4}$ alkyl group, optionally halogenated $C_{1-4}$ alkoxy group, optionally halogenated $C_{1-4}$ alkylthio group, hydroxyl group, amino group, mono- or di-$C_{1-4}$ alkylamino group, carboxyl group and $C_{1-4}$ alkoxy-carbonyl group.

4. A compound as claimed in claim 1, wherein the ring A and the ring B each are a benzene ring which may be substituted with 1 or 2 substituents selected from the group consisting of a halogen atom, optionally halogenated $C_{1-4}$ alkyl group and optionally halogenated $C_{1-4}$ alkoxy group.

5. A compound as claimed in claim 1, wherein the ring B is an unsubstituted benzene ring.

6. A compound as claimed in claim 1, wherein the ring A is a benzene ring which may be substituted with 1 or 2 substituents selected from the group consisting of a halogen atom and optionally halogenated $C_{1-4}$ alkyl group; and the ring B is an unsubstituted benzene ring.

7. A compound as claimed in claim 1, wherein R is a hydrogen atom.

8. A compound as claimed in claim 1, wherein R is a $C_{1-6}$ alkyl group.

9. A compound as claimed in claim 1, wherein Q is an oxygen atom.

10. A compound as claimed in claim 1, wherein X is —O—.

11. A compound as claimed in claim 1, wherein X is —NH—.

12. A compound as claimed in claim 1, wherein $R^2$ is (i) a hydrogen atom or (ii) a $C_{1-4}$ alkyl group which may be substituted with a $C_{1-4}$ alkoxy-carbonyl group or a carboxyl group.

13. A compound as claimed in claim 1, wherein $R^2$ is a hydrogen atom or a $C_{1-4}$ alkyl group.

14. A compound as claimed in claim 1, wherein Y is —NH—.

15. A compound as claimed in claim 1, wherein Y is a bond.

16. A compound as claimed in claim 1, wherein m is 1.

17. A compound as claimed in claim 1, wherein m is 2.

18. A compound as claimed in claim 1, wherein n is 0.

19. A compound as claimed in claim 1, wherein n is 1.

20. A compound as claimed in claim 1, wherein Ar is a phenyl group which may be substituted with 1 or 2 substituents selected from the group consisting of (i) an optionally halogenated $C_{1-4}$ alkyl group, (ii) a mono- or di-$C_{1-4}$ alkylamino-$C_{1-4}$ alkyl group, (iii) a carboxy-$C_{1-4}$ alkyl group, (iv) a $C_{1-4}$ alkoxy-carbonyl-$C_{1-4}$ alkyl group, (v) an optionally halogenated $C_{1-4}$ alkoxy group, (vi) a carboxy-$C_{1-4}$ alkoxy group, (vii) a $C_{1-4}$ alkoxy-carbonyl-$C_{1-4}$ alkoxy group, (viii) a halogen atom, (ix) a mono- or di-$C_{1-4}$ alkylamino group, (x) a $C_{1-4}$ alkoxy-carbonyl group and (xi) a carboxyl group.

21. A compound as claimed in claim 1, wherein Ar is a phenyl group which may be substituted with (i) an optionally halogenated $C_{1-4}$ alkoxy group, (ii) a carboxyl group, (iii) a carboxy-$C_{1-4}$ alkyl group, (iv) a mono- or di-$C_{1-4}$ alkylamino-$C_{1-4}$ alkyl group, (v) a mono- or di-$C_{1-4}$ alkylamino group or (vi) a carboxy-$C_{1-4}$ alkoxy group.

22. A compound as claimed in claim 1, wherein Ar is a phenyl group which may be substituted with one or two of a $C_{1-6}$ alkyl group optionally substituted with (i) an amino, (ii) a mono- or di-$C_{1-4}$ alkylamino or (iii) 5- to 9-membered cyclic amino optionally substituted with a $C_{1-4}$ alkyl.

23. A compound as claimed in claim 1, wherein Ar is a phenyl group which may be substituted with (i) an optionally halogenated $C_{1-4}$ alkoxy group or (ii) a mono- or di-$C_{1-4}$ alkylamino-$C_{1-4}$ alkyl group.

24. A compound as claimed in claim 1, wherein Ar is a phenyl group which may be substituted with an optionally halogenated $C_{1-4}$ alkoxy group.

25. A compound as claimed in claim 1, wherein Ar is a furyl, thienyl, pyrrolyl, oxazolyl, isoxazolyl, imidazolyl, pyrazolyl, pyridyl, pyridazinyl, quinolyl, isoquinolyl, indolyl, thiazolyl or thiadiazolyl group.

26. A compound as claimed in claim 1, wherein Ar is an indolyl group.

27. A compound as claimed in claim 1, wherein Q is an oxygen atom; R is a $C_{1-4}$ alkyl group; X is —NH—; and Y is —NH— or a bond.

28. A compound represented by the formula:

wherein the ring A' and the ring B' each are a benzene ring which may be substituted with 1 or 2 substituents selected from the group consisting of a halogen atom, optionally halogenated $C_{1-4}$ alkyl and optionally halogenated $C_{1-4}$ alkoxy;

Ar' is a phenyl group which may be substituted with 1 or 2 substituents selected from the group consisting of (i) an optionally halogenated $C_{1-4}$ alkyl, (ii) a mono- or di-$C_{1-4}$ alkylamino-$C_{1-4}$ alkyl, (iii) a carboxy-$C_{1-4}$ alkyl, (iv) a $C_{1-4}$ alkoxy-carbonyl-$C_{1-4}$ alkyl, (v) an optionally halogenated $C_{1-4}$ alkoxy, (vi) a carboxy-$C_{1-4}$ alkoxy, (vii) a $C_{1-4}$ alkoxy-carbonyl-$C_{1-4}$ alkoxy, (viii) a halogen atom, (ix) a mono- or di-$C_{1-4}$ alkylamino, (x) a $C_{1-4}$ alkoxy-carbonyl and (xi) a carboxyl;

R' is a $C_{1-4}$ alkyl group;

Q is an oxygen atom or a sulfur atom;

$X^a$ is —O— or —$NR^{1a}$—, wherein $R^{1a}$ is a hydrogen atom or a $C_{1-4}$ alkyl group;

$Y^a$ is —O—, —$NR^{2b}$ wherein $R^{2b}$ is a hydrogen atom or a $C_{1-4}$ alkyl group, or a bond; and n is 0, 1 or 2, or a pharmaceutically acceptable salt.

29. A compound as claimed in claim 28, wherein $X^a$ and $y^a$ are —NH—; and n is 0.

30. A compound as claimed in claim 28, wherein $X^a$ is —NH—, $Y^a$ is a bond; and n is 1.

31. A compound as claimed in claim 1, which is (i) N-[(6-chloro-1,2-dihydro-2-methyl-1-oxo-4 -phenylisoquinolin-3-yl)methyl]-N'-(3-isopropoxyphenyl)urea, (ii) N-[(6-chloro-1,2-dihydro-2 -methyl-1-oxo-4-phenylisoquinolin-3-yl)methyl]-N'-(3 -N,N-dimethylaminomethylphenyl)urea, (iii) N-(6 -chloro-1,2-dihydro-2-methyl-1-oxo-4-phenylisoquinolin-3 -yl)methyl-α-(3-isopropoxyphenyl)acetamide, (iv) N-(6 -chloro-1,2-dihydro-2-methyl-1-oxo-4-phenylisoquinolin- 3-yl)methyl-1-(3-methoxycarbonylphenyl)acetamide, (v) N-[(6-chloro-1,2-dihydro-2-methyl-1-oxo-4 -phenylisoquinolin-3-yl)methyl]-N'-{3-[2-(diethylamino)ethyl]phenyl}urea, (vi) N-[(6-chloro-1,2 -dihydro-2-methyl-1-oxo-4-phenylisoquinolin-3 -yl)methyl]-N'-{3-[2-(dimethylamino)ethoxy]phenyl}urea, (vii) N-[(6-chloro-1,2-dihydro-2-methyl-1-oxo-4 -phenylisoquinolin-3-yl)methyl]-N'-[3-(1-imidazolyl)propyl]urea, (viii) N-[(6-chloro-1,2 -dihydro-2-methyl-1-oxo-4-phenylisoquinolin-3-yl)methyl]-N'-[3-(methylamino)methylphenyl]urea, (ix) N-[(6-chloro-1,2-dihydro-2-methyl-1-oxo-4 -phenylisoquinolin-3-yl)methyl]-N'-[3-(ethylaminomethyl)phenyl]urea or (x) N-[3-(aminomethyl)phenyl]-N'-[(6-chloro-1,2-dihydro-2 -methyl-1-oxo-4-phenylisoquinolin-3-yl)methyl]urea, or a pharmaceutically acceptable salt thereof.

32. A pharmaceutical composition comprising a compound of the formula:

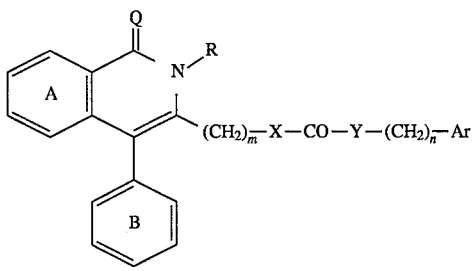

wherein the ring A and the ring B each are a benzene ring which may be substituted with one to four substituents selected from the group consisting of a halogen atom, optionally halogenated alkyl, optionally halogenated alkoxy, optionally halogenated alkylthio, $C_{1-7}$ acylamino, $C_{1-3}$ acyloxy, hydroxyl, nitro, amino, mono- or di-$C_{1-4}$ alkylamino, cyclic amino, $C_{1-4}$ alkyl-carbonylamino, $C_{1-4}$ alkylsulfonylamino, $C_{1-4}$ alkoxy-carbonyl, carboxyl, $C_{1-6}$ alkyl-carbonyl, carbamoyl, mono- or di-$C_{1-4}$ alkylcarbamoyl, and $C_{1-6}$ alkylsulfonyl at any substitutable ring position(s);

Ar is (I) an aryl group which may be substituted with the same or different 1 to 5 substituents selected from the group consisting of (a) a halogen atom, (b) a nitro group, (c) a cyano group, (d) a hydroxyl group, (e) an optionally halogenated $C_{1-4}$ alkoxy group, (f) a $C_{1-4}$ alkoxy group which may be substituted with a carboxyl group, (g) a $C_{1-4}$ alkoxy group which may be substituted with a $C_{1-4}$ alkoxy-carbonyl group, (h) an optionally halogenated $C_{1-4}$ alkylthio group, (i) an amino group, (j) a mono- or di-$C_{1-4}$ alkylamino group, (k) a cyclic amino group which may be substituted with a $C_{1-4}$ alkyl group, (l) a $C_{1-4}$ alkyl-carbonylamino group, (m) an aminocarbonyloxy group, (n) a mono- or di-$C_{1-4}$ alkylaminocarbonyloxy group, (o) a $C_{1-4}$ alkylsulfonylamino group, (p) a $C_{1-4}$ alkoxy-carbonyl group, (q) a benzyloxycarbonyl group; (r) a carboxyl group, (s) a $C_{1-4}$ alkyl-carbonyl group, (t) a $C_{3-6}$ cycloalkyl-carbonyl group, (u) a carbonyl group, (v) a mono- or di-$C_{1-4}$ alkylcarbamoyl group, (w) a alkylsulfonyl group, and (x) a hydrocarbon group which may be substituted with 1 to 5 substituents selected from the group consisting of (1) a halogen atom, (2) nitro, (3) cyano, (4) hydroxyl, (5) a $C_{1-4}$ alkoxy group, (6) a $C_{1-4}$ alkylthio group, (7) amino, (8) a mono- or di-$C_{1-4}$ alkylamino, (9) a cyclic amino group which may be substituted with a $c_{1-4}$ alkyl group, (10) a $C_{1-4}$ alkyl-carbonylamino group, (11) a $C_{1-4}$ alkylsulfonylamino group, (12) a $C_{1-4}$ alkoxy-carbonyl group, (13) carboxyl, (14) a $C_{1-6}$ alkyl-carbonyl group, (15) carbamoyl, (16) a mono- or di-$C_{1-4}$ alkylcarbamoyl group, (17) a $C_{1-6}$ alkylsulfonyl group, and (18) a phenyl group which may be substituted with a $C_{1-3}$ alkoxy group, at any substitutable position(s) thereof, or (II) a heterocyclic group which may be substituted with the same or different 1 to 5 substituents selected from the group consisting of (a) a halogen atom, (b) a nitro group, (c) cyano, (d) hydroxyl, (e) an optionally halogenated $C_{1-4}$ alkoxy group, (f) a $C_{1-4}$ alkoxy group which may be substituted with a carboxyl group, (g) a $C_{1-4}$ alkoxy group which may be substituted with a $C_{1-4}$ alkoxy-carbonyl group, (h) an optionally halogenated $C_{1-4}$ alkylthio group, (i) an amino group, (j) a mono- or di-$C_{1-4}$ alkylamino group, (k) a cyclic amino group which may be substituted with a $C_{1-4}$ alkyl group, (l) a $C_{1-4}$ alkyl-carbonylamino group, (m) an aminocarbonyloxy group, (n) a $C_{1-4}$ alkylsulfonylamino group, (p) a $C_{1-4}$ alkoxy-carbonyl group, (q) a benzyloxycarbonyl group, (r) a carboxyl group, (s) a $C_{1-4}$ alkyl-carbonyl group, (t) a $C_{3-6}$ cycloalkyl-carbonyl group, (u) a carbamoyl group, (v) a mono- or di-$C_{1-4}$ alkylcarbamoyl group, (w) a $C_{1-6}$ alkylsulfonyl group, and (x) a hydrocarbon group which may be substituted with 1 to 5 substituents selected from the group consisting of (1) a halogen atom, (2) nitro, (3) cyano, (4) hydroxyl, (5) a $C_{1-4}$ alkoxy group, (6) a $C_{1-4}$ alkylthio group, amino, (8) a mono- or di-$C_{1-4}$ alkylamino, (9) a cyclic amino group which may be substituted with a $C_{1-4}$ alkyl group, (10) a $C_{1-4}$ alkyl-carbonylamino group, (11) a $C_{1-4}$ alkylsulfonylamino group, (12) a $C_{1-4}$ alkoxy-carbonyl group, (13) carboxyl, (14) a $C_{1-6}$ alkyl-carbonyl group, (15) carbamoyl, (16) a mono- or di-$C_{1-4}$ alkylcarbamoyl group, (17) a $C_{1-6}$ alkylsulfonyl group, and (18) a phenyl group which may be substituted with a $C_{1-3}$ alkoxy group, at any substitutable position(s) of the ring;

Q is an oxygen atom or a sulfur atom;

is (I) a hydrogen atom, (II) a hydrocarbon group which may be substituted with 1 to 5 substituents selected from the group consisting of (a) a halogen atom, (b) a nitro group, (c) cyano, (d) hydroxyl, (e) an $C_{1-4}$ alkoxy group, (f) a $C_{1-4}$ alkylthio group, (g) amino, (h) a mono- or di-$C_{1-4}$ alkylamino group, (i) a cyclic amino group which may be substituted with a $C_{1-4}$ alkyl group, (j) a $C_{1-4}$ alkyl-carbonylamino group, (k) a $C_{1-4}$ alkylsulfonylamino group, (l) a $C_{1-4}$ alkoxy-carbonyl group, (m) carboxyl, (n) a $C_{1-6}$ alkyl-carbonyl group, (o) carbamoyl, (p) a mono- or di-$C_{1-4}$ alkylcarbamoyl group, (q) a $C_{1-6}$ alkylsulfonyl group, (r) a phenyl group which may be substituted with a $C_{1-3}$ alkoxy group, (III) a hydroxyl group which may be substituted with 1 or 2 substituents selected from the group consisting of (a) a halogen atom, (b) nitro, (c) cyano, (d) hydroxy, (e) a $C_{1-4}$ alkoxy group, (f) a $C_{1-4}$ alkylthio group, (g) amino group, (h) a mono- or di-$C_{1-4}$ alkylamino group, (i) a cyclic amino group which may be substituted with a $C_{1-4}$ alkyl group, (j) a $C_{1-4}$ alkyl-carbonylamino group, (k) a $C_{1-4}$ alkylsulfonylamino group, (l) a $C_{1-4}$ alkoxy-carbonyl group, (o) a carbamoyl group, (p) a mono- or di-$C_{1-4}$ alkylcarbamoyl group, (q) a $C_{1-6}$ alkylsulfonyl group, and (r) a phenyl group which may be substituted with a $C_{1-3}$ alkoxy group, or (IV) an amino group which may be substituted with 1 or 2 substituents selected from the group consisting of (i) a $C_{1-4}$ alkyl group, (ii) a $C_{1-4}$ alkyl-carbonyl group, (iii) a $C_{1-4}$ alkoxy-carbonyl group, or (iv) a phenyl group which may be substituted with halogen, a $C_{1-4}$ alkyl group, or a $C_{1-4}$ alkoxy group,;

X is —O— or —NR$^1$— wherein R$^1$ is a hydrogen atom or a hydrocarbon group which may be substituted with 1 to 5 substituents selected from the group consisting of (a) a halogen atom, (b) nitro, (c) cyano, (d) hydroxyl, (e) a $C_{1-4}$ alkoxy group, (f) a $C_{1-4}$ alkylthio group, (g) amino, (h) a mono- or di-$C_{1-4}$ alkyl amino, (i) a cyclic amino group which may be substituted with a $C_{1-4}$ alkyl group, (j) a $C_{1-4}$ alkyl-carbonylamino group, (k) a $C_{1-4}$ alkylsulfonylamino group, (l) a $C_{1-4}$ alkoxy-carbonyl group, (m) carboxyl, (n) a $C_{1-6}$ alkyl-carbonyl group, (o) carbamoyl, (p) a mono- or di-$C_{1-4}$ alkylcarbamoyl group, (q) a $C_{1-6}$ alkylsulfonyl group, and (r) a phenyl group which may be substituted with a $C_{1-3}$ alkoxy group;

Y is (I) —O—, (II) —NR$^2$— wherein R$^2$ is a hydrogen atom or hydrocarbon group which may be substituted with 1 to 5 substituents selected from the group consisting of (a) a halogen atom, (b) nitro, (c) cyano, (d) hydroxyl, (e) an $C_{1-4}$ alkoxy group; (f) a $C_{1-4}$ alkylthio group, (g) amino, (h) a mono- or di-$C_{1-4}$ alkylamino group, (i) a cyclic amino group which may be substituted with a $C_{1-4}$ alkyl group, (j) a $C_{1-4}$ alkyl-carbonyl amino group, (k) a $C_{1-4}$ alkylsulfonylamino group, (l) a $C_{1-4}$ alkoxy-carbonyl group, (m) carboxyl, (n) a $C_{1-6}$ alkyl-carbonyl group, (o) carbamoyl, (p) a mono- or di-$C_{1-4}$ alkylcarbamoyl group, (q) a $C_{1-6}$ alkylsulfonyl group, and (r) a phenyl group which may be substituted with a $C_{1-3}$ alkoxy group, or (III) a bond;

m denotes 1, 2 or 3, and n denotes 0, 1 or 2, or a pharmaceutically acceptable salt thereof with a pharmaceutically acceptable carrier or diluent.

33. A pharmaceutical composition as claimed in claim 32, which is a calcium antagonist.

34. A pharmaceutical composition as claimed in claim 32, which is a composition for treating a cerebralvascular disorder.

35. A pharmaceutical composition as claimed in claim 34, wherein the cerebralvascular disorder is neuronal damage or cerebralischemic damage.

36. A pharmaceutical composition in claim 32, which is a substance P receptor antagonist.

37. A method for treating a cerebralvascular disorder in mammals which comprises administering to a mammal in need thereof an effective amount of a compound of the formula:

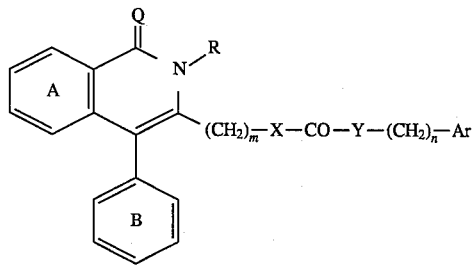

wherein the ring A and the ring B each are a benzene ring which may be substituted with one to four substituents selected from the group consisting of a halogen atom, optionally halogenated alkyl, optionally halogenated alkoxy, optionally halogenated alkylthio, $C_{1-7}$ acylamino, $C_{1-3}$ acyloxy, hydroxyl, nitro, amino, mono- or di-$C_{1-4}$ alkylamino, cyclic amino, $C_{1-4}$ alkyl-carbonylamino, $C_{1-4}$ alkylsulfonylamino, $C_{1-4}$ alkoxy-carbonyl, carboxyl, $C_{1-6}$ alkyl-carbonyl, carbamoyl, mono- or di-$C_{1-4}$ alkylcarbamoyl, and $C_{1-6}$ alkylsulfonyl at any substitutable ring position(s);

Ar is (I) an aryl group which may be substituted with the same or different 1 to 5 substituents selected from the group consisting of (a) a halogen atom, (b) a nitro group, (c) a cyano group, (d) a hydroxyl group, (e) an optionally halogenated $C_{1-4}$ alkoxy group, (f) a $C_{1-4}$ alkoxy group which may be substituted with a carboxyl group, (g) a $C_{1-4}$ alkoxy group which may be substituted with a $C_{1-4}$ alkoxy-carbonyl group, (h) an optionally halogenated $C_{1-4}$ alkylthio group, (i) an amino group, (j) a mono- or di-$C_{1-4}$ alkylamino group, (k) a cyclic amino group which may be substituted with a $C_{1-4}$ alkyl group, (l) a $C_{1-4}$ alkyl-carbonylamino group, (m) an aminocarbonyloxy group, (n) a mono- or di-$C_{1-4}$ alkylaminocarbonyloxy group, (o) a $C_{1-4}$ alkylsulfonylamino group, (p) a $C_{1-4}$ alkoxy-carbonyl group, (q) a benzyloxycarbonyl group, (r) a carboxyl group, (s) a $C_{1-4}$ alkyl-carbonyl group, (t) a $C_{3-6}$ cycloalkyl-carbonyl group, (u) a carbonyl group, (v) a mono- or di-$C_{1-4}$ alkylcarbamoyl group, (w) a $C_{1-6}$ alkylsulfonyl group, and (x) a hydrocarbon group which may be substituted with 1 to 5 substituents selected from the group consisting of (1) a halogen atom, (2) nitro, (3) cyano, (4) hydroxyl, (5) a $C_{1-4}$ alkoxy group, (6) a $C_{1-4}$ alkylthio group, (7) amino, (8) a mono- or di-$C_{1-4}$ alkylamino, (9) a cyclic amino group which may be substituted with a $C_{1-4}$ alkyl group, (10) a $C_{1-4}$ alkyl-carbonylamino group, (11) a $C_{1-4}$ alkylsulfonylamino group, (12) a $C_{1-4}$ alkoxy-carbonyl group, (13) carboxyl, (14) a $C_{1-6}$ alkyl-carbonyl group, (15) carbamoyl, (16) a mono- or di-$C_{1-4}$ alkyl-carbamoyl group, (17) a $C_{1-6}$ alkylsulfonyl group, and (18) a phenyl group which may be substituted with a $C_{1-3}$ alkoxy group, at any substitutable position(s) thereof, or (II) a heterocyclic group which may be substituted with the same or different 1 to 5 substituents selected from the group consisting of (a) a halogen atom, (b) a nitro group, (c) cyano, (d) hydroxyl, (e) an optionally halogenated $C_{1-4}$ alkoxy group, (f) a $C_{1-4}$ alkoxy group which may be substituted with a carboxyl group, (g) a $C_{1-4}$ alkoxy group which may be substituted With a $C_{1-4}$ alkoxy-carbonyl group, (h) an optionally halogenated $C_{1-4}$ alkylthio group, (i) an amino group, (j) a mono- or di-$C_{1-4}$ alkylamino group, (k) a cyclic amino group which may be substituted with a $C_{1-4}$ alkyl group, (l) a $C_{1-4}$ alkyl-carbonylamino group, (m) an aminocarbonyloxy group, (o) a $C_{1-4}$ alkylsulfonylamino group, (p) a $C_{1-4}$ alkoxy-carbonyl group, (q) a benzyloxycarbonyl group, (r) a carboxyl group, (s) a $C_{1-4}$ alkyl-carbonyl group, (t) a $C_{3-6}$ cycloalkyl-carbonyl group, (u) a carbamoyl group, (v) a mono- or di-$C_{1-4}$ alkylcarbamoyl group, (w) a $C_{1-6}$ alkylsulfonyl group, and (x) a hydrocarbon group which may be substituted with 1 to 5 substituents selected from the group consisting of (1) a halogen atom, (2) nitro, (3) cyano, (4) hydroxyl, (5) a $C_{1-4}$ alkoxy group, (6) a $C_{1-4}$ alkylthio group, (7) amino, (8) a mono- or di-$C_{1-4}$ alkylamino, (9) a cyclic amino group which may be substituted with a $C_{1-4}$ alkyl group, (10) a $C_{1-4}$ alkyl-carbonylamino group, (11) a $C_{1-4}$ alkylsulfonylamino group, (12) a $C_{1-4}$ alkoxy-carbonyl group, (13) carboxyl, (14) a $C_{1-6}$ alkyl-carbonyl group, (15) carbamoyl, (16) a mono- or di-$C_{1-4}$ alkylcarbamoyl group, (17) a $C_{1-6}$ alkylsulfonyl group, and (18) a phenyl group which may be substituted with a $C_{1-3}$ alkoxy group, at any substitutable position(s) of the ring;

Q is an oxygen atom or a sulfur atom;

R is (I) a hydrogen atom, (II) a hydrocarbon group which may be substituted with 1 to 5 substituents selected from the group consisting of (a) a halogen atom, (b) a nitro group, (c) cyano, (d) hydroxyl, (e) an alkoxy group, (f) a $C_{1-4}$ alkylthio group, (g) amino, (h) a mono- or di-$C_{1-4}$ alkylamino group, (i) a cyclic amino group which may be substituted with a $C_{1-4}$ alkyl group, (j) a $C_{1-4}$ alkyl-carbonylamino group, (k) a $C_{1-4}$ alkylsulfonylamino group, (l) a alkoxy-carbonyl group, (m) carboxyl, (n) a $C_{1-4}$ alkyl-carbonyl group, (o) carbamoyl, (p) a mono- or di-$C_{1-4}$ alkylcarbamoyl group, (q) a $C_{1-6}$ alkylsulfonyl group, (r) a phenyl group which may be substituted with a $C_{1-3}$ alkoxy group, (III) a hydroxyl group which may be substituted with 1 or 2 substituents selected from the group consisting of (a) a halogen atom, (b) nitro, (c) cyano, (d) hydroxy, (e) a $C_{1-4}$ alkoxy group, (f) a $C_{1-4}$ alkylthio group, (g) amino group, (h) a mono- or di-$C_{1-4}$ alkylamino group, (i) a cyclic amino group which may be substituted with a $C_{1-4}$ alkyl group, (j) a $C_{1-4}$ alkyl-carbonylamino group, (k) a $C_{1-4}$ alkylsulfonylamino group, (l) a $C_{1-4}$ alkoxy-carbonyl group, (o) a carbamoyl group, (p) a mono- or di-$C_{1-4}$ alkylcarbamoyl group, (q) a $C_{1-6}$ alkylsulfonyl group, and (r) a phenyl group which may be substituted with a $C_{1-3}$ alkoxy group, or (IV) an amino group which may be substituted with 1 or 2 substituents selected from the group consisting of (i) a $C_{1-4}$ alkyl group, (ii) a $C_{1-4}$ alkyl-carbonyl group, (iii) a $C_{1-4}$ alkoxy-carbonyl group, or (iv) a phenyl group which may be substituted with halogen, a $C_{1-4}$ alkyl group, or a $C_{1-4}$ alkoxy group,;

X is —O— or —$NR^1$— wherein $R^1$ is a hydrogen atom or a hydrocarbon group which may be substituted with 1 to 5 substituents selected from the group consisting of (a) a halogen atom, (b) nitro, (c) cyano, (d) hydroxyl, (e) a $C_{1-4}$ alkoxy group, (f) a $C_{1-4}$ alkylthio group, (g) amino, (h) a mono- or di-$C_{1-4}$ alkylamino, (i) a cyclic amino group which may be substituted with a $C_{1-4}$ alkyl group, (j) a $C_{1-4}$ alkyl-carbonylamino group, (k) a $C_{1-4}$ alkylsulfonylamino group, (l) a $C_{1-4}$ alkoxy-carbonyl group, (m) carboxyl, (n) a $C_{1-6}$ alkyl-carbonyl group, (o) carbamoyl, (p) a mono- or di-$C_{1-4}$ alkylcarbamoyl group, (q) a $C_{1-6}$ alkylsulfonyl group, and (r) a phenyl group which may be substituted with a $C_{1-3}$ alkoxy group;

Y is (I) —O—, (II) —NR$^2$— wherein R$^2$ is a hydrogen atom or hydrocarbon group which may be substituted with 1 to 5 substituents selected from the group consisting of (a) a halogen atom, (b) a nitro group, (c) cyano, (d) hydroxyl, (e) an $C_{1-4}$ alkoxy group, (f) a $C_{1-4}$ alkylthio group, (g) amino, (h) a mono- or di-$C_{1-4}$ alkylamino group, (i) a cyclic amino group which may be substituted with a $C_{1-4}$ alkyl group, (j) a $C_{1-4}$ alkyl-carbonylamino group, (k) a $C_{1-4}$ alkylsulfonylamino group, (l) a $C_{1-4}$ alkoxy-carbonyl group, (m) carboxyl, (n) a $C_{1-6}$ alkyl-carbonyl group, (o) carbamoyl, (p) a mono- or di-$C_{1-4}$ alkylcarbamoyl group, (q) a $C_{1-6}$ alkylsulfonyl group, and (r) a phenyl group which may be substituted with a $C_{1-3}$ alkoxy group, or (III) a bond;

m denotes 1, 2 or 3, and n denotes 0, 1 or 2, or a pharmaceutically acceptable salt thereof with a pharmaceutically acceptable carrier or diluent.

38. A method according to claim 37, wherein the cerebralvascular disorder is neuronal damage or cerebralischemic damage.

39. A compound selected from the group consisting of 1,2-dihydro-3-hydroxymethyl-2,6,7-trimethyl-1-oxo-4-phenylisoquinoline, 6-chloro-1,2-dihydro-3-hydroxymethyl-2-methyl-1-oxo-4-phenylisoquinoline, 3-aminoethyl-1,2-dihydro-2,6,7-trimethyl-1-oxo-4-phenylisoquinoline, 3-aminoethyl-1,2-dihydro-2-methyl-1-oxo-4-phenylisoquinoline, 3-aminoethyl-6-chloro-1,2-dihydro-2-methyl-1-oxo-4-phenylisoquinoline, and 6-chloro-1,2-dihydro-2-methyl-3-(N-methylamino)methyl-1-oxo-4 -phenylisoquinoline.

40. A compound represented by the formula:

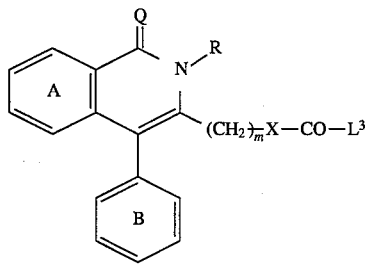

wherein L$^3$ is a leaving group;

ring A and ring B each are a benzene ring which may be substituted with one to four substituents selected from the group consisting of a halogen atom, optionally halogenated alkyl, optionally halogenated alkoxy, optionally halogenated alkylthio, $C_{1-7}$ acylamino, $C_{1-3}$ acyloxy, hydroxyl, nitro, amino, mono- or di-$C_{1-4}$ alkylamino, cyclic amino, $C_{1-4}$ alkyl-carbonylamino, $C_{1-4}$ alkylsulfonylamino, $C_{1-4}$ alkoxy-carbonyl, carboxyl, $C_{1-6}$ alkyl-carbonyl, carbamoyl, mono- or di-$C_{1-4}$ alkylcarbamoyl, and $C_{1-6}$ alkylsulfonyl at any substitutable ring position(s);

Q is an oxygen atom or a sulfur atom;

R is (I) a hydrogen atom, (II) a hydrocarbon group which may be substituted with 1 to 5 substituents selected from the group consisting of (a) a halogen atom, (b) a nitro group, (c) cyano, (d) hydroxyl, (e) an $C_{1-4}$ alkoxy group, (f) a $C_{1-4}$ alkylthio group, (g) amino, (h) a mono- or di-$C_{1-4}$ alkylamino group, (i) a cyclic amino group which may be substituted with a $C_{1-4}$ alkyl group, (j) a $C_{1-4}$ alkyl-carbonylamino group, (k) a $C_{1-4}$ alkylsulfonylamino group, (l) a $C_{1-4}$ alkoxy-carbonyl group, (m) carboxyl, (n) a $C_{1-4}$ alkyl-carbonyl group, (o) carbamoyl, (p) a mono- or di-$C_{1-4}$ alkylcarbamoyl group, (q) a $C_{1-6}$ alkylsulfonyl group, (r) a phenyl group which may be substituted with a $C_{1-3}$ alkoxy group, (III) a hydroxyl group which may be substituted with 1 or 2 substituents selected from the group consisting of (a) a halogen atom, (b) nitro, (c) cyano, (d) hydroxy, (e) a $C_{1-4}$ alkoxy group, (f) a $C_{1-4}$ alkylthio group, (g) amino group, (h) a mono- or di-$C_{1-4}$ alkylamino group, (i) a cyclic amino group which may be substituted with a $C_{1-4}$ alkyl group, (j) a $C_{1-4}$ alkyl-carbonylamino group, (k) a $C_{1-4}$ alkylsulfonylamino group, (l) a $C_{1-4}$ alkoxy-carbonyl group, (o) a carbamoyl group, (p) a mono- or di-$C_{1-4}$ alkylcarbamoyl group, (q) a $C_{1-6}$ alkylsulfonyl group, and (r) a phenyl group which may be substituted with a $C_{1-3}$ alkoxy group, or (IV) an amino group which may be substituted with 1 or 2 substituents selected from the group consisting of (i) a $C_{1-4}$ alkyl group, (ii) a $C_{1-4}$ alkyl-carbonyl group, (iii) a $C_{1-4}$ alkoxy-carbonyl group, or (iv) a phenyl group which may be substituted with halogen, a $C_{1-4}$ alkyl group, or a $C_{1-4}$ alkoxy group;

X is —O— or —NR$^1$— wherein R$^1$ is a hydrogen atom or a hydrocarbon group which may be substituted with 1 to 5 substituents selected from the group consisting of (a) a halogen atom, (b) nitro, (c) cyano, (d) hydroxyl, (e) a $C_{1-4}$ alkoxy group, (f) a $C_{1-4}$ alkylthio group, (g) amino, (h) a mono- or di-$C_{1-4}$ alkylamino, (i) a cyclic amino group which may be substituted with a $C_{1-4}$ alkyl group, (j) a $C_{1-4}$ alkyl-carbonylamino group, (k) a $C_{1-4}$ alkylsulfonylamino group, (l) a $C_{1-4}$ alkoxy-carbonyl group, (m) carboxyl, (n) a $C_{1-6}$ alkyl-carbonyl group, (o) carbamoyl, (p) a mono- or di-$C_{1-4}$ alkylcarbamoyl group, (q) a $C_{1-6}$ alkylsulfonyl group, and (r) a phenyl group which may be substituted with a $C_{1-3}$ alkoxy group; and m denotes 1, 2 or 3; or a salt thereof.

* * * * *

UNITED STATES PATENT AND TRADEMARK OFFICE
CERTIFICATE OF CORRECTION

PATENT NO. : 5,527,811
DATED : June 18, 1996
INVENTOR(S) : Hideaki NATSUGARI, et. al.

It is certified that error appears in the above-identified patent and that said Letters Patent is hereby corrected as shown below:

Column 50, Line 59, delete "imono-" and insert --mono--

Column 51, Line 5, delete "amino carbonyloxy" and insert --aminocarbonyloxy--

Column 51, Line 36, delete "(g)" and insert --(q)--

Column 51, Line 44, delete "group, amino," and insert --group, (7) amino--

Column 51, Line 46, delete "$C_{1-4}$ group" and insert --$C_{1-4}$ alkyl group--

Column 51, Line 63, delete "(g)" and insert --(q)--

Column 51, Line 65, delete "(III) a hydroxyl group" and insert --(III) a unsubstituted hydroxyl group or a substituted hydroxyl group, wherein the substituted hydroxyl group is a group selected from a $C_{1-4}$ alkoxy group, a $C_{6-10}$ aryloxy group, a $C_{1-4}$ alkyl-carbonyloxy group, or a $C_{6-10}$ aryl-carbonyloxy group, each of--

Column 52, Line 9, delete "$C_{1-5}$" and insert --$C_{1-3}$--

Column 52, Line 14, delete "$C_{1-4}$ alkoxy group,;" and insert --$C_{1-4}$ alkoxy group;--

UNITED STATES PATENT AND TRADEMARK OFFICE
CERTIFICATE OF CORRECTION

PATENT NO. : 5,527,811
DATED : June 18, 1996
INVENTOR(S) : Hideaki NATSUGARI, et al.

It is certified that error appears in the above-indentified patent and that said Letters Patent is hereby corrected as shown below:

Column 52, Line 38, delete "(g)" and insert --(q)--

Column 54, Line 52, delete "1-(3-methoxycarbonylphenyl)" and insert --a-(3-methoxycarbonylphenyl)--

Column 55, Line 37, delete "(g)" and insert --(q)--

Column 55, Line 67, delete "(g)" and insert --(q)--

Column 56, Line 8, delete "group, amino," and insert --group, (7) amino,--

Column 56, Line 18, delete "is (I)" and insert --R is (I)--

Column 56, Line 28, delete "(g)" and insert --(q)--

Column 56, Line 30, delete "(III) a hydroxy group" and insert --(III) a unsubstituted hydroxyl group or a substituted hydroxyl group, wherein the substituted hydroxyl group is a group selected from a $C_{1-4}$ alkoxy group, a $C_{6-10}$ aryloxy group, a $C_{1-4}$ alkyl-carbonyloxy group, a $C_{6-10}$ aryl-carbonyloxy group, each of--

Column 56, Line 39, delete "(g)" and insert --(q)--

Column 56, Line 46, delete "alkoxy group,;" and insert --alkoxy group;--

UNITED STATES PATENT AND TRADEMARK OFFICE
CERTIFICATE OF CORRECTION

PATENT NO. : 5,527,811
DATED : June 18, 1996
INVENTOR(S) : Hideaki NATSUGARI, et al.

It is certified that error appears in the above-indentified patent and that said Letters Patent is hereby corrected as shown below:

Column 56, Line 52, delete "alkyl amino" and insert --alkylamino--

Column 56, Line 57, delete "(g)" and insert --(q)--

Column 57, Line 1, delete "$C_{1-4}$," and insert --$C_{1-4}$--

Column 57, Line 3, delete "(g)" and insert --(q)--

Column 57, Line 58, delete "(g)" and insert --(q)--

Column 58, Line 14, delete "With" and insert --with--

Column 58, Line 20, delete "(g)" and insert --(q)--

Column 58, Line 41, delete "an alkoxy group" and insert --a $C_{1-4}$ alkoxy group--

Column 58, Line 45, delete "a alkoxy-carbonyl" and insert --a $C_{1-4}$ alkoxy-carbonyl--

Column 58, Line 46, delete "$C_{1-4}$" and insert --$C_{1-6}$--

UNITED STATES PATENT AND TRADEMARK OFFICE
CERTIFICATE OF CORRECTION

PATENT NO. : 5,527,811
DATED : June 18, 1996
INVENTOR(S) : Hideaki NATSUGARI, et al.

It is certified that error appears in the above-indentified patent and that said Letters Patent is hereby corrected as shown below:

Column 58, Lines 49-50, delete "(III) a hydroxyl group" and insert --(III) a unsubstituted hydroxyl group or a substituted hydroxyl group, wherein the substituted hydroxyl group is a group selected from a $C_{1-4}$ alkoxy group, a $C_{6-10}$ aryloxy group, a $C_{1-4}$ alkyl-carbonyloxy group, or a $C_{6-10}$ aryl-carbonyloxy group, each of--

Column 58, Line 65, delete "alkoxy group,;" and insert --alkoxy group;--

Column 59, Line 21, delete "(g)" and insert --(q)--

Column 60, Line 18, delete "$C_{1-4}$" (2nd occurrence) and insert --$C_{1-6}$--

UNITED STATES PATENT AND TRADEMARK OFFICE
CERTIFICATE OF CORRECTION

PATENT NO.   : 5,527,811
DATED        : June 18, 1996
INVENTOR(S)  : Hideaki NATSUGARI, et al It is certified that error appears in the above-indentified patent and that said Letters Patent is hereby corrected as shown below:

Column 60, Line 22, delete "(III) a hydroxyl group" and insert --(III) a unsubstituted hydroxyl group or a substituted hydroxyl group, wherein the substituted hydroxyl group is a group selected from a $C_{1-4}$ alkoxy group, a $C_{6-10}$ aryloxy group, a $C_{1-4}$ alkyl-carbonyloxy group, or a $C_{6-10}$ aryl-carbonyloxy group, each of--

Signed and Sealed this

Fifteenth Day of October, 1996

Attest:

BRUCE LEHMAN

*Attesting Officer*    *Commissioner of Patents and Trademarks*